United States Patent
Wood, Jr. et al.

(10) Patent No.: US 9,067,047 B2
(45) Date of Patent: Jun. 30, 2015

(54) INJECTABLE CONTROLLED RELEASE FLUID DELIVERY SYSTEM

(75) Inventors: Lowell L. Wood, Jr., Bellevue, WA (US); Clarence T. Tegreene, Bellevue, WA (US); William H. Gates, III, Redmond, WA (US); Roderick A. Hyde, Redmond, WA (US)

(73) Assignee: THE INVENTION SCIENCE FUND I, LLC, Bellevue, WA (US)

(*) Notice: Subject to any disclaimer, the term of this patent is extended or adjusted under 35 U.S.C. 154(b) by 944 days.

(21) Appl. No.: 11/975,726

(22) Filed: Oct. 19, 2007

(65) Prior Publication Data

US 2009/0227988 A1    Sep. 10, 2009

Related U.S. Application Data

(63) Continuation-in-part of application No. 11/807,200, filed on May 25, 2007, now abandoned, and a continuation-in-part of application No. 11/271,145, filed on Nov. 9, 2005, now Pat. No. 8,585,684, and a
(Continued)

(51) Int. Cl.
    *A61M 31/00*    (2006.01)
    *A61B 5/00*     (2006.01)
    (Continued)

(52) U.S. Cl.
    CPC .............. *A61M 31/00* (2013.01); *A61B 5/0031* (2013.01); *A61B 5/4839* (2013.01); *A61M 31/002* (2013.01); *A61M 37/0069* (2013.01); *G06F 19/3468* (2013.01)

(58) Field of Classification Search
    CPC ............ A61M 31/00; A61M 37/0069; A61M 31/002; G06F 19/3468; A61B 5/4839; A61B 5/0031
    USPC .................... 604/892.1, 93.01, 890.1, 65–67, 604/131–133
    See application file for complete search history.

(56) References Cited

U.S. PATENT DOCUMENTS

| 3,760,806 | A | 9/1973 | Leeper |
| 3,923,426 | A | 12/1975 | Theeuwes |

(Continued)

FOREIGN PATENT DOCUMENTS

| JP | 60118289 A | 6/1985 |
| WO | WO 00/66204 A1 | 11/2000 |

(Continued)

OTHER PUBLICATIONS

UK Intellectual Property Office Examination Report Under Section 18(3); App. No. GB0809510.1; bearing a date of Oct. 27, 2010; pp. 1-2.

(Continued)

*Primary Examiner* — Aarti B Berdichevsky
*Assistant Examiner* — Bradley Osinski
(74) *Attorney, Agent, or Firm* — Dorsey & Whitney LLP

(57) ABSTRACT

Embodiments of a material delivery device including a deformable reservoir and associated controllable output mechanism are described. Methods of use and control of the device are also disclosed. According to some embodiments, a material delivery device may be placed in an animal in order to controllably dispense at least one material into the animal. The material delivery device may include a programmable mechanism to control the release of the material into the animal. In selected embodiments, a remote controller may be used to program or to control the material delivery device. Some embodiments are described wherein a magnetic field, an electric field, or electromagnetic control signal may be used.

23 Claims, 26 Drawing Sheets

Related U.S. Application Data continuation-in-part of application No. 11/271,146, filed on Nov. 9, 2005, and a continuation-in-part of application No. 11/270,799, filed on Nov. 9, 2005, now Pat. No. 8,998,884, and a continuation-in-part of application No. 11/272,455, filed on Nov. 9, 2005, now Pat. No. 7,817,030, and a continuation-in-part of application No. 11/272,572, filed on Nov. 9, 2005, and a continuation-in-part of application No. 11/272,573, filed on Nov. 9, 2005, and a continuation-in-part of application No. 11/272,524, filed on Nov. 9, 2005, now Pat. No. 8,617,141, and a continuation-in-part of application No. 11/302,449, filed on Dec. 13, 2005, and a continuation-in-part of application No. 11/335,785, filed on Jan. 18, 2006, now Pat. No. 7,942,867, and a continuation-in-part of application No. 11/302,321, filed on Dec. 13, 2005, now Pat. No. 8,273,075, and a continuation-in-part of application No. 11/302,407, filed on Dec. 13, 2005, now Pat. No. 8,998,886, and a continuation-in-part of application No. 11/302,450, filed on Dec. 13, 2005, now Pat. No. 7,699,834, and a continuation-in-part of application No. 11/335,786, filed on Jan. 18, 2006, now Pat. No. 8,882,747, and a continuation-in-part of application No. 11/335,788, filed on Jan. 18, 2006, now abandoned, and a continuation-in-part of application No. 11/335,911, filed on Jan. 18, 2006, now abandoned, and a continuation-in-part of application No. 11/372,226, filed on Mar. 9, 2006, now Pat. No. 8,936,590, and a continuation-in-part of application No. 11/372,492, filed on Mar. 9, 2006, now Pat. No. 8,992,511.

(51) Int. Cl.
*A61M 37/00* (2006.01)
*G06F 19/00* (2011.01)

(56) References Cited

U.S. PATENT DOCUMENTS

| | | | |
|---|---|---|---|
| 4,263,910 A | 4/1981 | Pardekooper et al. | |
| 4,360,019 A | 11/1982 | Portner et al. | |
| 4,373,527 A | 2/1983 | Fischell | |
| 4,513,034 A * | 4/1985 | Sparer et al. | 428/1.6 |
| 4,579,837 A | 4/1986 | Busch et al. | |
| 4,692,147 A | 9/1987 | Duggan | |
| 4,714,462 A * | 12/1987 | DiDomenico | 604/67 |
| 4,753,636 A | 6/1988 | Free | |
| 4,787,888 A | 11/1988 | Fox | |
| 4,834,704 A | 5/1989 | Reinicke | |
| 4,861,484 A | 8/1989 | Lichtin et al. | |
| 4,883,666 A | 11/1989 | Sabel et al. | |
| 4,929,233 A | 5/1990 | Roth et al. | |
| 4,944,659 A | 7/1990 | Labbe et al. | |
| 5,045,082 A | 9/1991 | Ayer et al. | |
| 5,049,141 A | 9/1991 | Olive | |
| 5,207,666 A | 5/1993 | Idriss et al. | |
| 5,368,571 A | 11/1994 | Horres, Jr. | |
| 5,370,611 A * | 12/1994 | Niezink et al. | 604/62 |
| 5,370,672 A | 12/1994 | Fowler et al. | |
| 5,391,164 A | 2/1995 | Giampapa | |
| 5,484,403 A * | 1/1996 | Yoakum et al. | 604/59 |
| 5,523,746 A | 6/1996 | Gallagher | |
| 5,651,979 A | 7/1997 | Ron et al. | |
| 5,655,539 A | 8/1997 | Wang et al. | |
| 5,670,162 A | 9/1997 | Baile et al. | |
| 5,698,220 A | 12/1997 | Cardinal et al. | |
| 5,719,296 A | 2/1998 | Acton, III et al. | |
| 5,733,313 A * | 3/1998 | Barreras et al. | 607/33 |
| 5,766,242 A | 6/1998 | Wong et al. | |
| 5,770,222 A | 6/1998 | Unger et al. | |
| 5,797,898 A | 8/1998 | Santini, Jr. et al. | |
| 5,800,420 A | 9/1998 | Gross et al. | |
| 5,814,599 A | 9/1998 | Mitragotri et al. | |
| 5,827,186 A | 10/1998 | Chen et al. | |
| 5,869,078 A * | 2/1999 | Baudino | 424/423 |
| 5,879,329 A | 3/1999 | Ginsburg | |
| 5,945,762 A | 8/1999 | Chen et al. | |
| 6,048,328 A | 4/2000 | Haller et al. | |
| 6,077,837 A | 6/2000 | Kozak | |
| 6,086,582 A | 7/2000 | Altman et al. | |
| 6,146,103 A | 11/2000 | Lee et al. | |
| 6,198,950 B1 | 3/2001 | Kraus | |
| 6,198,963 B1 | 3/2001 | Haim et al. | |
| 6,206,914 B1 | 3/2001 | Soykan et al. | |
| 6,246,241 B1 | 6/2001 | Newland | |
| 6,283,949 B1 | 9/2001 | Roorda | |
| 6,339,897 B1 | 1/2002 | Hayes et al. | |
| 6,358,247 B1 | 3/2002 | Altman et al. | |
| 6,454,759 B2 | 9/2002 | Krulevitch et al. | |
| 6,458,118 B1 | 10/2002 | Lent et al. | |
| 6,464,687 B1 | 10/2002 | Ishikawa et al. | |
| 6,475,750 B1 | 11/2002 | Han et al. | |
| 6,491,684 B1 | 12/2002 | Joshi et al. | |
| 6,527,762 B1 | 3/2003 | Santini, Jr. et al. | |
| 6,537,256 B2 | 3/2003 | Santini, Jr. et al. | |
| 6,554,822 B1 | 4/2003 | Holschneider et al. | |
| 6,562,000 B2 | 5/2003 | Thompson et al. | |
| 6,589,205 B1 * | 7/2003 | Meadows | 604/67 |
| 6,590,267 B1 | 7/2003 | Goodwin-Johansson et al. | |
| 6,607,553 B1 | 8/2003 | Healy et al. | |
| 6,615,074 B2 | 9/2003 | Mickle et al. | |
| 6,628,989 B1 | 9/2003 | Penner et al. | |
| 6,655,035 B2 | 12/2003 | Ghandi et al. | |
| 6,663,821 B2 | 12/2003 | Seward | |
| 6,669,683 B2 | 12/2003 | Santini, Jr. et al. | |
| 6,719,449 B1 | 4/2004 | Laugharn, Jr. et al. | |
| 6,723,086 B2 | 4/2004 | Bassuk et al. | |
| 6,768,246 B2 | 7/2004 | Pelrine et al. | |
| 6,768,920 B2 | 7/2004 | Lange et al. | |
| 6,802,489 B2 | 10/2004 | Marr et al. | |
| 6,845,267 B2 | 1/2005 | Harrison et al. | |
| 6,849,463 B2 | 2/2005 | Santini, Jr. et al. | |
| 6,929,636 B1 | 8/2005 | von Alten | |
| 6,935,165 B2 | 8/2005 | Bashir et al. | |
| 6,948,843 B2 | 9/2005 | Laugharn, Jr. et al. | |
| 6,970,741 B1 | 11/2005 | Whitehurst et al. | |
| 6,974,445 B2 | 12/2005 | Stergiopulos | |
| 7,048,730 B2 | 5/2006 | Petrakis | |
| 7,059,348 B2 | 6/2006 | Nat | |
| 7,063,691 B2 | 6/2006 | Nelson et al. | |
| 7,083,593 B2 | 8/2006 | Stultz | |
| 7,104,988 B2 | 9/2006 | Altman et al. | |
| 7,118,531 B2 | 10/2006 | Krill | |
| 7,137,994 B2 | 11/2006 | de Juan, Jr. et al. | |
| 7,214,190 B1 | 5/2007 | Wilson | |
| 7,351,239 B2 | 4/2008 | Gill | |
| 7,424,330 B2 | 9/2008 | Duerr et al. | |
| 7,474,180 B2 | 1/2009 | Bintoro et al. | |
| 7,641,619 B2 | 1/2010 | Penner | |
| 7,699,834 B2 | 4/2010 | Hood et al. | |
| 7,811,279 B2 | 10/2010 | John | |
| 7,817,030 B2 | 10/2010 | Hood et al. | |
| 7,819,858 B2 | 10/2010 | Goodall et al. | |
| 7,896,867 B2 | 3/2011 | Gordon et al. | |
| 7,896,868 B2 | 3/2011 | Hood et al. | |
| 7,942,867 B2 | 5/2011 | Hood et al. | |
| 8,083,710 B2 | 12/2011 | Hood et al. | |
| 8,109,923 B2 | 2/2012 | Hood et al. | |
| 8,114,065 B2 | 2/2012 | Hood et al. | |
| 8,192,390 B2 | 6/2012 | Hood et al. | |
| 8,273,075 B2 | 9/2012 | Hood et al. | |
| 8,348,930 B2 | 1/2013 | Gordon et al. | |
| 8,349,261 B2 | 1/2013 | Hood et al. | |
| 8,367,003 B2 | 2/2013 | Hood et al. | |
| 8,512,241 B2 | 8/2013 | Bandy et al. | |
| 8,529,551 B2 | 9/2013 | Hood et al. | |
| 2001/0044620 A1 | 11/2001 | Krulevitch et al. | |
| 2002/0065509 A1 | 5/2002 | Lebel et al. | |
| 2002/0072784 A1 | 6/2002 | Sheppard, Jr. et al. | |

(56) References Cited

U.S. PATENT DOCUMENTS

| | | | |
|---|---|---|---|
| 2002/0077673 A1* | 6/2002 | Penner et al. | 607/60 |
| 2002/0107472 A1 | 8/2002 | Thompson et al. | |
| 2002/0111601 A1* | 8/2002 | Thompson | 604/514 |
| 2002/0173773 A1 | 11/2002 | Olsen | |
| 2003/0014091 A1 | 1/2003 | Rastegar et al. | |
| 2003/0015768 A1* | 1/2003 | Bosco et al. | 257/528 |
| 2003/0036746 A1 | 2/2003 | Penner et al. | |
| 2003/0069560 A1 | 4/2003 | Adamis et al. | |
| 2003/0104590 A1 | 6/2003 | Santini, Jr. et al. | |
| 2003/0147812 A1 | 8/2003 | Ueberle | |
| 2003/0163223 A1 | 8/2003 | Blomquist | |
| 2003/0165648 A1 | 9/2003 | Lobovsky et al. | |
| 2003/0171257 A1 | 9/2003 | Stirbl et al. | |
| 2003/0171738 A1 | 9/2003 | Konieczynski et al. | |
| 2003/0219470 A1 | 11/2003 | Zhang et al. | |
| 2004/0007051 A1 | 1/2004 | Bashir et al. | |
| 2004/0010219 A1 | 1/2004 | McCusker et al. | |
| 2004/0015154 A1 | 1/2004 | Harper et al. | |
| 2004/0032187 A1 | 2/2004 | Penner et al. | |
| 2004/0034332 A1 | 2/2004 | Uhland | |
| 2004/0055648 A1 | 3/2004 | Erickson | |
| 2004/0058101 A1 | 3/2004 | Klemm | |
| 2004/0076559 A1 | 4/2004 | Brucker et al. | |
| 2004/0082908 A1 | 4/2004 | Whitehurst et al. | |
| 2004/0106914 A1* | 6/2004 | Coppeta et al. | 604/892.1 |
| 2004/0115128 A1 | 6/2004 | Schnitzer | |
| 2004/0120827 A1 | 6/2004 | Kim et al. | |
| 2004/0121486 A1 | 6/2004 | Uhland et al. | |
| 2004/0127844 A1 | 7/2004 | Flaherty | |
| 2004/0133188 A1 | 7/2004 | Vardi et al. | |
| 2004/0147906 A1 | 7/2004 | Voyiazis et al. | |
| 2004/0166140 A1 | 8/2004 | Santini, Jr. et al. | |
| 2004/0182704 A1 | 9/2004 | Daunert et al. | |
| 2004/0186576 A1 | 9/2004 | Biscup et al. | |
| 2004/0193144 A1 | 9/2004 | Krumme | |
| 2004/0193166 A1 | 9/2004 | Biscup | |
| 2004/0204744 A1 | 10/2004 | Penner et al. | |
| 2004/0223985 A1 | 11/2004 | Dunfield et al. | |
| 2004/0230182 A1 | 11/2004 | Heruth et al. | |
| 2004/0256584 A1 | 12/2004 | Zimmerling et al. | |
| 2004/0264293 A1 | 12/2004 | Laugharn, Jr. et al. | |
| 2005/0055014 A1 | 3/2005 | Coppeta et al. | |
| 2005/0096587 A1 | 5/2005 | Santini, Jr. et al. | |
| 2005/0123563 A1 | 6/2005 | Doranz et al. | |
| 2005/0143802 A1 | 6/2005 | Soykan et al. | |
| 2005/0181366 A1 | 8/2005 | Ostermeier | |
| 2005/0187515 A1 | 8/2005 | Varrichio et al. | |
| 2005/0187677 A1* | 8/2005 | Walker | 701/16 |
| 2005/0191194 A1 | 9/2005 | Falk et al. | |
| 2005/0191708 A1 | 9/2005 | Saul et al. | |
| 2005/0192637 A1 | 9/2005 | Girouard et al. | |
| 2005/0208469 A1 | 9/2005 | Daunert et al. | |
| 2005/0234431 A1 | 10/2005 | Williams et al. | |
| 2005/0267440 A1 | 12/2005 | Herman et al. | |
| 2005/0277912 A1 | 12/2005 | John | |
| 2006/0004417 A1 | 1/2006 | Rossing et al. | |
| 2006/0089751 A1 | 4/2006 | Herbst | |
| 2006/0116641 A1 | 6/2006 | Gordon et al. | |
| 2006/0149321 A1 | 7/2006 | Merry et al. | |
| 2006/0201432 A1* | 9/2006 | Pratt | 119/51.02 |
| 2006/0224128 A1 | 10/2006 | Lurvey et al. | |
| 2006/0241747 A1 | 10/2006 | Shaoulian et al. | |
| 2006/0283465 A1 | 12/2006 | Nickel et al. | |
| 2007/0016171 A1 | 1/2007 | Podvin et al. | |
| 2007/0074722 A1 | 4/2007 | Giroux et al. | |
| 2007/0078445 A1 | 4/2007 | Malloy | |
| 2007/0104023 A1 | 5/2007 | Hood et al. | |
| 2007/0106269 A1 | 5/2007 | Hood et al. | |
| 2007/0106270 A1 | 5/2007 | Hood et al. | |
| 2007/0106271 A1 | 5/2007 | Hood et al. | |
| 2007/0106281 A1 | 5/2007 | Hood et al. | |
| 2007/0135797 A1 | 6/2007 | Hood et al. | |
| 2007/0135798 A1 | 6/2007 | Hood et al. | |
| 2007/0135799 A1 | 6/2007 | Hood et al. | |
| 2007/0135800 A1 | 6/2007 | Hood et al. | |
| 2007/0135801 A1 | 6/2007 | Hood et al. | |
| 2007/0147170 A1 | 6/2007 | Hood et al. | |
| 2007/0149954 A1 | 6/2007 | Hood et al. | |
| 2009/0018704 A1 | 1/2009 | Hood et al. | |
| 2009/0024114 A1 | 1/2009 | Hood et al. | |
| 2009/0227988 A1 | 9/2009 | Wood, Jr. et al. | |

FOREIGN PATENT DOCUMENTS

| | | |
|---|---|---|
| WO | WO 02/056790 A2 | 7/2002 |
| WO | WO 03/049592 A2 | 6/2003 |
| WO | WO 2005/084273 A3 | 9/2005 |

OTHER PUBLICATIONS

UK Intellectual Property Office Examination Report Under Section 18(3); App. No. GB0809489.8; bearing a date of Oct. 27, 2010; pp. 1-3.

UK Intellectual Property Office Examination Report Under Section 18(3); App. No. GB0809491.4; bearing a date of Oct. 27, 2010; pp. 1-2.

Beebe, D.J.; Moore, J.S.; Bauer, J.M.; Yu, Q.; Liu, R.H.; Devadoss, C.; Jo, B.; "Functional hydrogel structures for autonomous flow control inside microfluidic channels"; Nature; Apr. 6, 2000; pp. 588-590; vol. 404.

Bullis, Kevin; "Easy-to-Make Nanosensors: Tiny electronics-based detectors could provide simple tests for cancer or bioterror agents."; Technology Review; bearing a date of Jan. 31, 2007; printed on May 9, 2007; located at http://www.technologyreview.com/Nanotech/18127/.

Deo, Sapna; Eisenhardt, Patricia; Moschou, Elissavet; Peteu, Serban; Bachas, Leonidas; Madou, Marc; Daunert, Sylvia; "Responsive Drug Delivery Systems"; Analytical Chemistry; May 1, 2003; pp. 207A-213A; vol. 75, No. 9.

Erion et al.; "Liver-Targeted Drug Delivery Using HepDirect[1] Prodrugs"; Journal of Pharmacology and Experimental Therapeutics Fast Forward, JPET; 2005; pp. 554-560; vol. 312, No. 2; The American Society for Pharmacology and Experimental Therapeutics.

Gabriel, Jean-Christophe P.; "Large Scale Production of Carbon Nanotube Transistors: A Generic Platform for Chemical Sensors"; Mat. Res. Soc. Symp. Proc.; 2003; pp. Q.12.7.1-Q.12.7.7; vol. 776; Materials Research Society.

Gruner, G.; "Carbon Nanotube Transistors for Biosensing Applications"; Anal. Bioanal. Chem.; 2006; pp. 322-335; vol. 384.

Halperin, M.D., Scott A.; "The Control of Pertussis—2007 and Beyond"; New England Journal of Medicine; Jan. 11, 2007; pp. 110-113; vol. 356, No. 2.

Hilt, J. Zachary; Peppas, Nicholas A.; "Microfabricated drug delivery devices"; International Journal of Pharmaceutics; 2005; pp. 15-23; vol. 306; Elsevier B.V.

Krauβ et al.; "Fluid pumped by magnetic stress"; Jun. 22, 2006; pp. 1-3; located at: http://arxiv.org/PS_cache/physics/pdf/0405/0405025.pdf.

Low, L.; Seetharaman, S.; He, K.; Madou, M.J.; "Microactuators toward microvalves for responsive controlled drug delivery"; Sensors and Actuators B; 2000; pp. 149-160; vol. 67; Elsevier Science S.A.

Madou, M.; Florkey, J.; "From batch to continuous manufacturing of microbiomedical devices"; Chem. Rev.; 2000; pp. 2679-2692; vol. 100; American Chemical Society.

Madou, Dr. Marc J.; Bachas, Dr. Leonidas G.; "Responsive Drug Delivery Systems"; Sylvia Daunert's Research Group; printed on Feb. 15, 2007; pp. 1-7 (6 pages provided); located at http://www.chem.uky.edu/research/daunert/group/ResponsiveDrugDeliverySyst.html.

Neto, et al.; "Optical, Magnetic and Dielectric Properties of Non-Liquid Crystalline Elastomers Doped with Magnetic Colloids"; Brazilian Journal of Physics; Mar. 2005; pp. 184-189; vol. 35, No. 1.

Prescott, James H.; Lipka, Sara; Baldwin, Samuel; Sheppard, Jr., Norman F.; Maloney, John M.; Coppeta, Jonathan; Yomtov, Barry; Staples, Mark A.; Santini, Jr., John T.; "Chronic, programmed polypeptide delivery from an implanted, multireservoir microchip device"; Nature Biotechnology; Apr. 2006; pp. 437-438; vol. 24, No. 4.

(56) References Cited

OTHER PUBLICATIONS

Robinson et al.; "LEAPT: Lectin-directed enzyme-activated prodrug therapy"; PNAS; Oct. 5, 2004; pp. 14527-14532; vol. 101, No. 40; located at http://www.pnas.org/cgi/content/full/101/40/14527.

Staples, Mark; Daniel, Karen; Cima, Michael J.; Langer, Robert; "Application of Micro-and Nano-Electromechanical Devices to Drug Delivery"; Pharmaceutical Research; May 2006; pp. 847-863; vol. 23, No. 5; Springer Netherlands; located at http://www.springerlink.com/content/02560n1180942576/.

The University of Texas at Austin; "MEMS/NEMS-Based Drug Delivery Device"; 2002; printed on Feb. 15, 2007; pp. 1-5; located at http://www.otc.utexas.edu/ATdisplay.jsp?id=546&cat=10 and http://www.bme.utexas.edu/faculty/roy.cfm.

UK Intellectual Property Office Examination Report Under Section 18(3); App. No. GB0809487.2; bearing a date of Oct. 1, 2010 pp. 1-2.

Irsigler, K; Kritz, H; Hagmuller, G; Franetzki, M; Prestele, K; Thurow, H; Geisen, K; "Long-Term Continuous Intraperitoneal Insulin Infusion With an Implanted Remote-Controlled Insulin Infusion Device"; Diabetes; bearing a date of Dec. 1981; pp. 1072-1075; vol. 30; American Diabetes Association.

Scavini, Marina MD; Schade, David S. MD; "Implantable Insulin Pumps"; Clinical Diabetes; bearing a date of Mar./Apr. 1996; printed on Jun. 28, 2007; pp. 1-10; vol. 14; No. 2; American Diabetes Association; located at http://journal.diabetes.org/clinicaldiabetes/v14n2M-A96/pg30.htm.

UK Intellectual Property Office Examination Report Under Section 18(3); App. No. GB0809489.8; bearing a date of Jul. 25, 2011; pp. 1-2.

Agarwal et al.; "Magnetically-driven temperature-controlled microfluidic actuators"; in Proc. $1^{st}$ Int. Workshop on Networked Sensing Syst., Jun. 22-23, 2004 pp. 1-4; located at http://mnsa.ece.wisc.edu/Publications/C4/C4.pdf; Tokyo, Japan.

UK Intellectual Property Office Examination Report Under Section 18(3); App. No. GB0921925.4; Jun. 9, 2011; pp. 1-5.

UK Intellectual Property Office Examination Report Under Section 18(3); App. No. GB0809498.9; Jan. 7, 2011; 3 pages.

European Patent Office; Extended European Search Report; App. No. EP 06 82 7655; Mar. 11, 2013; pp. 1-10.

Shoji et al.; "Microflow devices and systems"; J. Micromech. Microeng.; bearing a date of 1994; pp. 157-171; vol. 4; IOP Publishing Ltd.

UK Intellectual Property Office Examination Report Under Section 18(3); App. No. GB0809500.2; bearing a date of Jul. 29, 2011; pp. 1.

UK Intellectual Property Office Examination Report Under Section 18(3); App. No. GB0809510.1; bearing a date of Jul. 29, 2011; pp. 1.

UK Intellectual Property Office Examination Report Under Section 18(3); App. No. GB0809491.4; bearing a date of Aug. 4, 2011; pp. 1-2.

Japanese Examination Report; App. No. 2008-540179; Oct. 6, 2011; pp. 1-3; no translation provided.

Hackworth, Martin; "Sound Waves I"; Idaho State University Department of Physics; printed on Sep. 9, 2014; 13 pages; located at http://www2.cose.isu.edu/~hackmart/soundwaveslengphys.pdf.

* cited by examiner

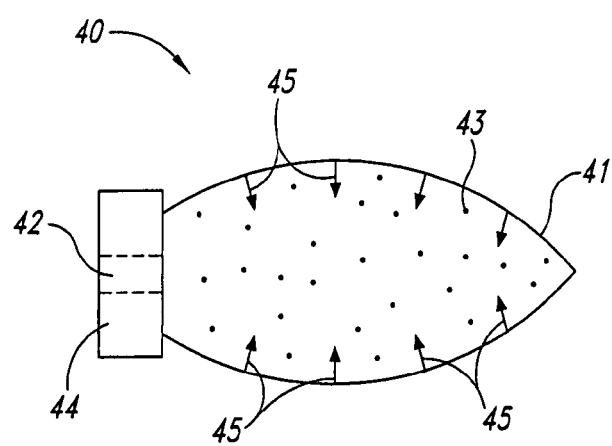
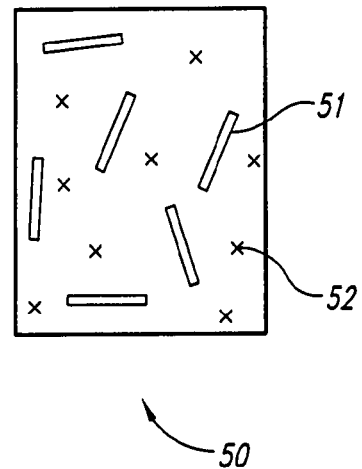
*Fig. 4*     *Fig. 5*
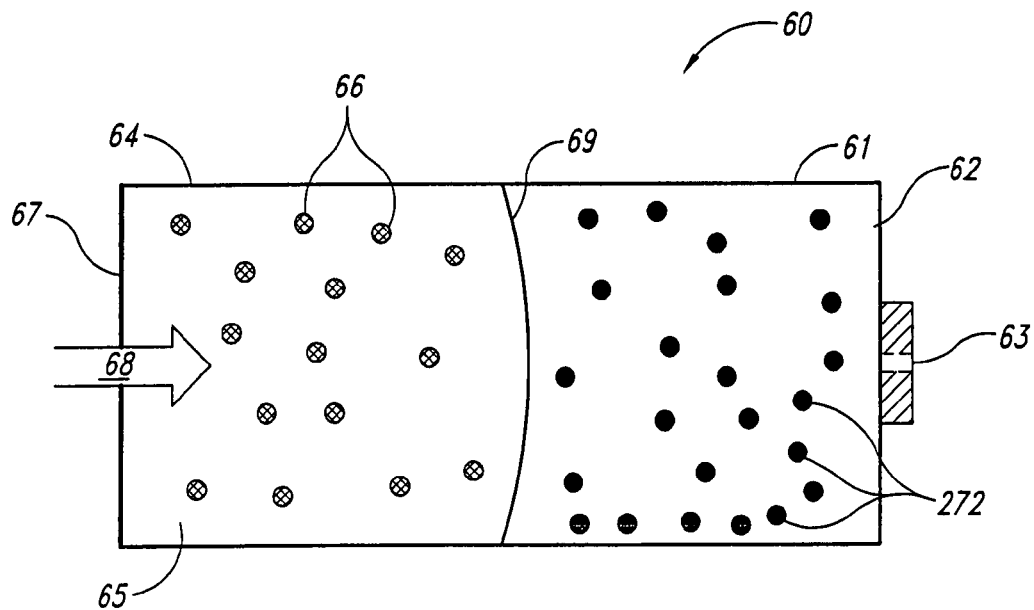
*Fig. 6*

$T_1 < T_2$ $T_1 > T_2$

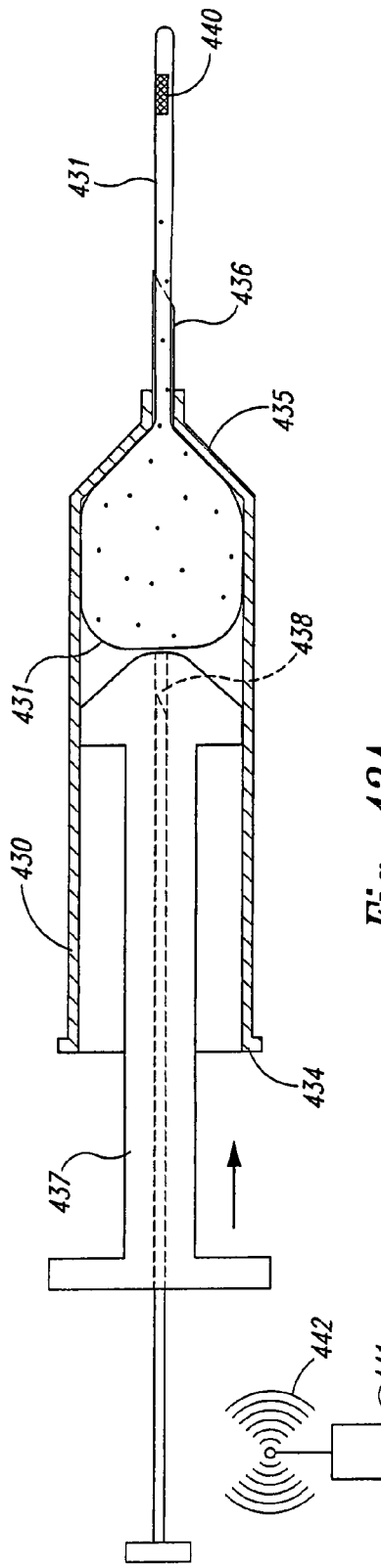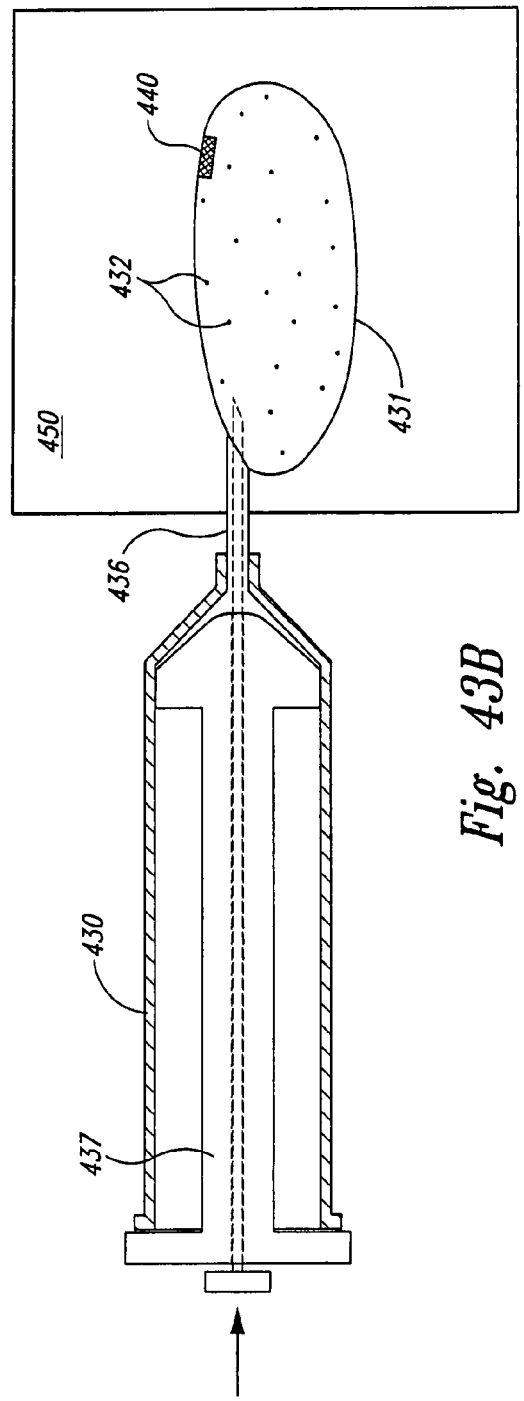
Fig. 43A
Fig. 43B

INJECTABLE CONTROLLED RELEASE FLUID DELIVERY SYSTEM

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of United States Patent Application No. 11/807,200, now abandoned titled INJECTABLE CONTROLLED RELEASE FLUID DELIVERY SYSTEM, naming William H. Gates, III, Roderick A. Hyde, Clarence T. Tegreene, and Lowell L. Wood, Jr. as inventors, filed May 25, 2007, which is co-pending, or is an application of which a co-pending application is entitled to the benefit of the filing date.

For purposes of the USPTO extra-statutory requirements, the present application constitutes a continuation-in-part of U.S. patent application Ser. No. 11/271,145 now U.S. Pat. No. 8,585,684, titled REACTION DEVICE CONTROLLED BY MAGNETIC CONTROL SIGNAL, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/271,146, titled REACTION DEVICE CONTROLLED BY RF CONTROL SIGNAL, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/270,799 now U.S. Pat. No. 8,998,884 titled REMOTE CONTROLLED IN SITU REACTION METHOD, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, an application of which a currently co-pending application is entitled to the benefit of the filing date.

For purposes of the USPTO extra-statutory requirements, the present application constitutes a continuation-in-part of U.S. patent application Ser. No. 11/272,455 now U.S. Pat. No. 7,817,030, titled REMOTE CONTROLLER FOR IN SITU REACTION DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/272,572, titled REMOTE CONTROLLED IN VIVO REACTION METHOD, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the date.

For purposes of the USPTO extra-statutory requirements, the present application constitutes a continuation-in-part of U.S. patent application Ser. No. 11/272,573, titled IN SITU REACTION DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/272,524 now Pat. No. 8,617,141, titled REMOTE CONTROLLED IN SITU REACTION DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, an application of which a currently co-pending application is entitled to the benefit of the filing date.

For purposes of the USPTO extra-statutory requirements, the present application constitutes a continuation-in-part of U.S. patent application Ser. No. 11/302,449, titled OSMOTIC PUMP WITH REMOTELY CONTROLLED OSMOTIC PRESSURE GENERATION, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Dec. 13, 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/335,785 now U.S. Pat. No. 7,942,867, titled REMOTELY CONTROLLED SUBSTANCE DELIVERY DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Jan. 18, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/302,321 now U.S. Pat. 8,273,075, titled OSMOTIC PUMP WITH REMOTELY CONTROLLED OSMOTIC FLOW RATE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Dec. 13, 2005, which is currently co-pending, or is and application of which a currently co-pending application is entitled to the benefit of the filing date.

For purposes of the USPTO extra-statutory requirements, the present application constitutes a continuation-in-part of U.S. patent application Ser. No. 11/302,407 now U.S. Pat. No. 8,998,886, titled REMOTE CONTROL OF OSMOTIC PUMP DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Dec. 13, 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/302,450 now U.S. Pat. No. 7,699,834, titled METHOD AND SYSTEM FOR CONTROL OF OSMOTIC PUMP DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Dec. 13, 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/335,786 now U.S. Pat. No. 8,882,747, titled SUBSTANCE DELIVERY SYSTEM, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Jan. 18, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/335,788 now abandoned, titled REMOTE CONTROL OF SUBSTANCE DELIVERY SYSTEM, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Jan. 18, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/335,911 now abandoned, titled REMOTE CONTROLLER FOR SUBSTANCE DELIVERY SYSTEM, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Jan. 18, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/372,226 now U.S. Pat. No. 8,936,590 titled ACOUSTICALLY CONTROLLED REACTION DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Mar. 9, 2006, which is currently co-pending, or is an application of which a currently co-pending application is entitled to the benefit of the filing date.

For purposes of the USPTO extra-statutory requirements, the present application constitutes a continuation-in-part of United States Patent Application No. 11/372,492 titled ACOUSTICALLY CONTROLLED SUBSTANCE DELIVERY DEVICE, naming Leroy E. Hood, Muriel Y. Ishikawa, Edward K.Y. Jung, Robert Langer, Clarence T. Tegreene, Lowell L. Wood, Jr. and Victoria Y. H. Wood as inventors, filed Mar. 9, 2006 , now U.S. No. 8,992,511 which is co-pending, or is an application of which co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

In vivo drug delivery is now accomplished by a number of technologies including actuator pumps, osmotic pumps, and release from highly-engineered materials. Implantable controlled release devices for drug delivery have been developed. Certain devices rely upon the gradual release of a drug from a polymeric carrier over time, due to degradation of the carrier. Polymer-based drug release devices are being developed that include a drug in a ferropolymer that may be manipulated by an externally applied magnetic field, thus influencing the drug release. MEMS-based drug release devices that include integrated electrical circuitry are also under development, as are MEMS-based systems for performing chemical reactions. Implantable osmotic pump devices have been developed for drug delivery purposes.

SUMMARY

The application relates, in general, to the field of material delivery devices and systems for delivering materials within an animal. In particular, the application relates to intelligently-controlled material delivery systems including devices that are capable of being deployed transcutaneously, percutaneously, or subdermally into a natural or an engineered body cavity of an animal. The device is capable of long-term delivery of material in vivo and may be adapted to receive externally-provided delivery material. That is, the device may be loadable with delivery material once the device is deployed in vivo. The device may be self-powered, may contain a programmable processor or may be activated by external means.

Embodiments of a system including a remotely-controlled material delivery device and associated controller are described. Methods of use and control of the device are also disclosed. According to various embodiments, a material delivery device may be placed in an in vivo environment of an animal in order to eject or release a material into the in vivo environment. Embodiments are described for a delivery device comprising at least one deformable reservoir configured to receive, retain and dispense at least one material, including at least one outlet through which material may exit a deformable reservoir; and at least one controllable output mechanism operably linked to the at least one outlet to control the dispensing of at least a portion of at least one material exiting from the at least one deformable reservoir. The device may also contain a processor or memory, or other self-contained structure for activating the controllable output mechanism. Also described is a system comprising the device and a remote controller configured to generate and transmit a control signal sufficient to the material delivery device. The control signal may itself activate the controllable output mechanism or it may provide instructions to the device for activating the controllable output mechanism. Further embodiments are described including methods for delivering a material into a human or other animal. Further embodiments include the percutaneously-deployable material delivery device including sensors that sense environmental conditions and provide a signal that may be used to activate the at least one controllable output mechanism to control the exit of material from the deformable reservoir. Other embodiments are contemplated wherein the material delivery device is self-powered, that is, comprising a power supply or a power-harvesting device, for example, one that generates power in response to an electromagnetic signal, or in response to local acceleration. Such local acceleration may be associated with movement of the environment within the subject animal. In some embodiments, the body of the subject may be used as a power source for powering the device. Various "energy scavenging" or "energy harvesting" devices are known, or may be developed (see e.g., U.S. Pat. Nos. 6,615,074, 6,655,035 and 6,768,246, and published U.S. Patent applications 20030014091 and 20030165648, each of which is incorporated herein by reference insofar as it may be compatible). For example, devices that capture energy from body movement of the subject (e.g., inertial devices as are used to power self-winding wristwatches) may be used to power the device. Pressure and chemical gradients within the body may also provide energy for powering operation of the device. For example, energy may be captured from the systolic-diastolic cycle or pulsatile blood flow of the subject, or through a micro-turbine placed in the respired airflow of the subject. Energy scavenging devices may scavenge energy from the subject's environment, as well. An embodiment of a material delivery device includes a power-receiving structure that is configured to receive power, or energy, from the environment. The device may be configured to store energy received or to promptly use the energy received to power the device.

Other embodiments are contemplated that utilize a micropump or nanopump to pump the material from the at least one reservoir. The disclosure contemplates that the reservoir may be a flexible elastomeric material that is able to change its shape in at least one dimension upon being filled with material once injected into the subject animal. The reservoir may be a geometrically reconfigurable member that is placed with a lumen of the animal and is loaded with material for delivery to the animal. The approach also contemplates the use of a remote controller positioned either inside or outside of the animal that is capable of transmitting a control signal to activate the controllable output mechanism to cause exit of material from the reservoir. The remote controller may be programmed to provide a control signal based on a sensed condition either within or external to the animal and/or on a set time schedule. The remote controller may be configured to provide programmable instructions to the device. The rate of exit of material from the at least one deformable reservoir may be constant or variable, or made to occur at controllable intervals.

An embodiment relates to the percutaneous deployment of a material delivery device using a deployment mechanism. In some applications, this embodiment may allow simpler and faster deployment with a syringe-like means, instead of surgical deployment. In many cases, deployment of the device may be done entirely under local anesthesia or perhaps with no anesthesia at the time of the primary procedure, leaving only a puncture site rather than an incision. Such percutaneous deployment can be less painful and/or less likely to result in complications such as wound infection or injury to surrounding tissues.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 4 illustrates in schematic form an embodiment of a delivery device utilizing positive pressure to deliver material from the reservoir;

FIG. 5 depicts an electromagnetically responsive control element including a polymer and magnetically or electrically active components;

FIG. 6 shows an example of a delivery device including an osmotic pump;

FIG. 43A is a schematic of a drug delivery kit including a syringe and a drug delivery device;

FIG. 43B is a schematic of the kit in use;

DETAILED DESCRIPTION

Figure 1:
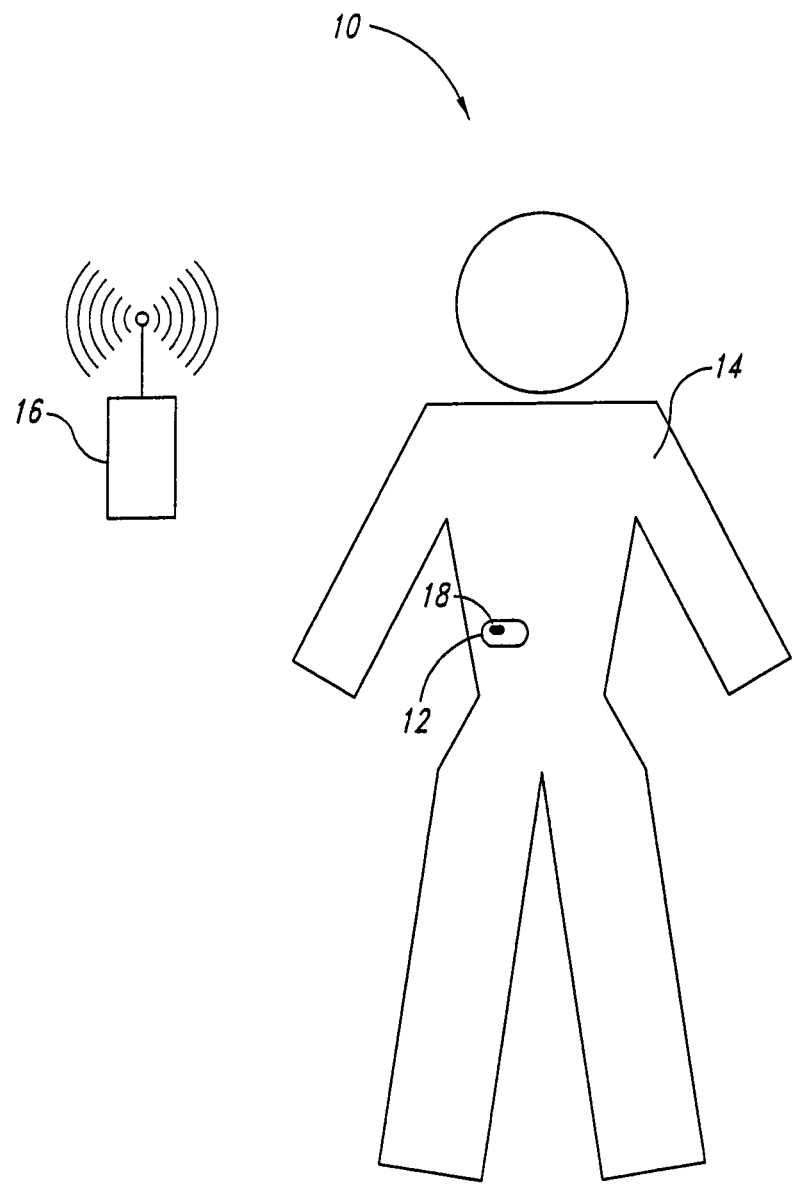
FIG. 1 depicts an embodiment of a delivery system for use in a human subject.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

As used herein the term "percutaneously deployable" and similar terms such as "percutaneously deployed", "percutaneous deployment", "transcutaneously deployable" mean the deployment of a material delivery device through the skin or hide layer of an animal. Percutaneous deployment of the material delivery device may be performed into any in vivo lumen or body cavity, for example, the peritoneal cavity, thoracic cavity, sinus cavity, nasal cavity, or the like, or it may be subdermal, e.g., in an ad hoc cavity. The term "animal" as used herein means vertebrates, such as mammals, birds, reptiles, amphibians, and fishes. Still further, the term "mammal" as used herein means warm-blooded higher vertebrates (as placentals, marsupials, or monotremes) that nourish their young with milk secreted by mammary glands, have the skin usually more or less covered with hair, and includes humans. Other mammals include, and are not limited to, livestock and pets.

Described herein are embodiments that include a material delivery device deployable in an animal, comprising at least one deformable reservoir configured to receive, retain and dispense at least one material, including at least one outlet through which the at least one material may exit the at least one deformable reservoir; and at least one controllable output mechanism operably linked to the at least one outlet to control the dispensing of at least a portion of the at least one material from the at least one deformable reservoir. Further described are embodiments including A material delivery system, comprising at least one material delivery device deployable in an animal, including at least one deformable reservoir configured to receive, retain and dispense at least one material, including at least one outlet through which the at least one material may exit the at least one deformable reservoir, at least one controllable output mechanism operably linked to the at least one outlet to control the dispensing of at least a portion of the at least one material from the at least one deformable reservoir; and at least one remote controller configured to generate and transmit at least one control signal to the at least one material delivery device. Still further are described embodiments that include A material delivery kit, comprising at least one deployment mechanism; at least one material delivery device deployable in an animal, including at least one deformable reservoir configured to receive, retain and controllably release at least one material, including at least one outlet through which the at least one material may be released from the at least one deformable reservoir; and at least one controllable output mechanism operably linked to said at least one outlet and configured to control the release of the at least one material from the at least one deformable reservoir. Further described herein are embodiments that include a method of delivering at least one material to an animal, comprising deploying at least one material delivery device into an in vivo environment of the animal, the at least one material delivery device including at least one deformable reservoir configured to receive, retain and controllably dispense the at least one material, and including at least one outlet, and at least one controllable output mechanism operably linked to the at least one outlet; and delivering a quantity of the at least one material into the at least one deformable reservoir; wherein the at least one controllable output mechanism dispenses the at least one material in response to at least one control signal.

FIG. 1 depicts an example of an embodiment of a material delivery system 10. As used herein, delivery "material" means a substance that is in the form of a solid, a fluid or a material that is fluidizable, or a gas. A delivery material may be any of a wide variety of materials, including single materials, two or more distinct materials, or mixtures of materials. For example, a delivery material may comprise a compound that exhibits a physiological effect, a therapeutic agent, a pharmaceutical material or its pharmaceutically acceptable salt, adduct or derivative, a biological, a chemical compound, a peptide or nucleotide or glycopeptide or lipopeptide, a nutrient or micronutrient, a nutraceutical material, or any combination thereof. A delivery material may be a biologically active material, including a cell, cell component, virus, provirus, or microscopic lifeform. In some embodiments, a delivery material may include at least one nutrient, hormone, growth factor, medication, therapeutic compound, enzyme, genetic material, vaccine, vitamin, neurotransmitter, cytokine, cell-signaling material, pro- or anti-apoptotic agent, imaging agent, labeling agent, diagnostic compound, material or agent, nanomaterial, inhibitor, or blocker. In some embodiments, the delivery material may be a component or precursor of a biologically active material; for example, the delivery material may include at least one precursor or component of a nutrient, hormone, growth factor, medication, therapeutic compound, enzyme, genetic material, vaccine, vitamin, neurotransmitter, cytokine, cell-signaling material, pro- or anti-apoptotic agent, imaging agent, labeling agent, diagnostic compound, nanomaterial, inhibitor, or blocker. Such precursors, may include, for example, prodrugs (see, e.g., "Liver-Targeted Drug Delivery Using HepDirect1 Prodrugs," Erion et al., Journal of Pharmacology and Experimental Therapeutics Fast Forward, JPET 312:554-560, 2005 (stating a first publication date of Aug. 31, 2004) and "LEAPT: Lectin-directed enzyme-activated prodrug therapy", Robinson et al., PNAS Oct. 5, 2004 vol. 101, No. 40, 14527-14532, stating published online before print Sep. 24, 2004 (http://www.pnas.org/cgi/content/full/101/40/14527), both of which are incorporated herein by reference. Beneficial materials may be produced, for example, by conversion of prodrug to drug by enzymatic reaction of material in the bloodstream or a tissue or an organ (CYP450, cholesterol metabolism, e.g., with cholesterol monooxygenase, cholesterol reductase, cholesterol oxidase).

Therapeutic agents that are known to those of skill in the art may be used in the delivery device described herein. Therapeutic agents may include, for example, agents for treating autoimmune disease, osteoporosis, cancer, Type I or Type II diabetes, mental disorders such as depression, bipolar disorder or schizophrenia, and infectious diseases and consequences thereof.

Depending, on the intended application or use environment for the delivery device, the delivery material may include at least one antibiotic, microbicide, antiviral, fungicide, transfection agent, or nanomaterial. In some embodiments, the delivery material may include a tissue-specific marker or targeting molecule, which may be, for example, a tissue-specific endothelial-homing protein. A tissue-specific marker or targeting molecule may assist in targeting of the delivery material to a specific location or tissue within a body of an animal.

The material delivery device described herein may be used to controllably deliver medications aimed at the prevention or treatment of diseases commonly occurring in Third World countries. Such diseases are known to one having ordinary skill in the art and include, but are not limited to, those described herein. Embodiments of the material delivery device may include programming the device, for example, either prior to deployment in vivo, or subsequent to deployment in vivo, to deliver at least one material to the in vivo environment. The programming may include steps for a long-term delivery regimen of material, for example, daily delivery for a period of days, or weeks or months. Delivery may be scheduled, using the device described herein, in a constant manner to permit consistent and maintained blood levels of a material. Some delivery regiments may take into account the pharmacokinetic properties of the material in order to maintain a desired blodd concentration of the material. As described herein, some embodiments of the material delivery device may include sensors that are configured to sense a biological condition or other parameter of the environment. The device may be programmed to respond to the sensed condition or parameter. Some diseases or infections may require delivery of therapeutic material over the course of months in order to prevent a recurrence of the disease or to create an immunity to a delivered vaccine. It will be apparent to one having ordinary skill in the art that the material delivery device described herein allows for myriad variations in delivering materials to an animal, and in particular a human. Any aspect of the function of the material delivery device including, but not limited to, the timing and quantity or concentration of material delivery, may be programmed into the device or may be controlled by a remote controller, as desired by the user. For example, immunization may be achieved using a vaccine delivered by the material delivery device according to a pulsed or widely-spaced time intervals.

Examples of delivery materials include but are not limited to, at least one of efavirenz, lamivudine and zidovudine, tenofovir (Viread®), and emtricitabine (Emtriva®) for delivery singularly or in any combination or sequence for treating HIV-1 infections, or first-line (e.g., isoniazid and rifampicin) or second-line drugs (e.g., fluoroquinolones, thioamides, macrolides) for treating tuberculosis infections. Other embodiments include the delivery of at least one delivery material that is an anti-viral or an anti-microbial agent. Still other embodiments include the delivery of at least two delivery materials wherein at least one delivery material is a vaccine.

Vaccines, whether delivered singly or in combination with another delivery material may be, for example, viral or bacterial vaccines. Examples of diseases for which vaccines can be delivered include, but are not limited to, malaria, HIV, tuberculosis, measles, influenza, hepatitis A, hepatitis B, hepatitis C, hepatitis E, hepatitis G, HPV, schistosomiasis, leischmaniasis, smallpox (variola), pneumonia, diphtheria, and cancer. Treatments for malarial infection are well known to those of skill in the art and may include use of at least one of the following agents chloroquine, sulfadoxine-pyrimethamine (Fansidar®), mefloquine (Lariam®), atovaquone-proguanil (Malarone®), quinine, doxycycline, artemisin derivatives, and/or primaquine. Treatments for tuberculosis are well known to those of skill in the art and may include isoniazid, rifampin, pyrazinamide, rifapentine and/or ethambutol. Vaccines for measles infection are well known to those of skill in the art. Treatments for leischmaniasis infection are well known to those of skill in the art and may include antimony-containing compounds, including meglumine antimonite, sodium stibogluconate, pentamidine, and/or amphotericin B. Treatments for smallpox infection are well known to those of skill in the art and may include anti-infectives and/or anti-viral agents. Treatments for bacterial pneumonia are well known to those of skill in the art and may include at least one of the following agents: macrolides, such as Ery-Tab, Biaxin, Biaxin XL, and Zithromax; tetracyclines, such as doxycycline (Vibramycin, Doryx); fluoroquinolones, such as Levaquin and Avelox; cephalosporins, such as Ceclor, Duricef, Ceftin, and Lorabid; penicillins, such as Amoxil, Biomox, Omnipen, Augmentin, Veetids, and Timentin; vancomycin (Vancocin) and/or ketolides (telithromycin). Treatments for diphtheria infection are well known to those of skill in the art and may include antitoxin. Treatments for hepatitis C infection are well known to those of skill in the art and may include, for example, pegylated interferon alfa-2a, ribavirin and telaprevir, or any combination thereof.

Vaccines for HIV-1 are well known to those of skill in the art and may include a fragment or portion of the HIV-1 envelope protein gp120, in particular the portion of gp120 that is bound by antibody b12. Other delivery materials may include an immune system modulator, or a vaccine adjuvant. A vaccine adjuvant is a component that potentiates the immune responses to an antigen and/or modulates it towards the desired immune responses.

Examples of vaccine adjuvants include mineral salts, such as, e.g., aluminum hydroxide and aluminum or calcium phosphate gels; oil emulsions and surfactant based formulations, such as e.g., MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilised water-in-oil emulsion); particulate adjuvants, such as, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG); microbial derivatives (natural and synthetic), such as, e.g., monophosphoryl lipid A (MPL), Detox (MPL+M. Phlei cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators, such as, e.g., hGM-CSF or hIL-12 (cytokines that can be administered either as protein or plasmid encoded), Immudaptin (C3d tandem array); and inert vehicles, such as gold particles.

Other embodiments include the use of delivery materials that are delivered on a when-needed and/or as-much-as-needed basis, for example, insulin, or a pain medication.

One or more of the material delivery devices described herein may be used to control the therapeutic delivery of controlled substance materials in vivo and/or prevent the abuse or thereof or addiction thereto by the patient. For example, prescription pain medications or other potentially addictive materials may be delivered in quantities and according to a schedule or time-program that avoids or minimizes the likelihood of addiction or abuse. Examples of some of the most widely abused controlled substances include opioids, also known as narcotic analgesics. Used to treat pain, opioids are the most commonly abused prescription drugs. Examples of opioids include morphine, codeine, OxyContin (oxycodone), Vicodin (hydrocodone) and Demerol (meperidine). Other controlled substances include central nervous system depressants that are commonly used to treat anxiety, panic attacks, and sleep disorders. Examples include Nembutal (pentobarbital sodium), Valium (diazepam), and Xanax (alprazolam). Other controlled substances include central nervous system stimulants that are commonly used to treat the sleeping disorder narcolepsy and attention-deficit/hyperactivity disorder. Examples include Ritalin (methylphenidate) and Dexedrine (dextroamphetamine). These drugs, which can be addictive, enhance brain activity and increase alertness and energy. Similar means may be employed to preclude or minimize the likelihood of overdosing, especially relative to the individual or then-prevailing characteristics of a particular subject.

Schedules suitable for use with the material delivery device described and claimed herein may be those that are pre-established, for example, by a physician, or by the patient according to a model or preset guidelines. In addition, a schedule may be established according to a particular measurement, for example, a measurement made by a physiological sensor such as those described herein.

One or more of the material delivery devices described herein may be used to control the therapeutic delivery of anti-depressant or psychotropic agents in vivo and/or prevent the abuse or thereof or addiction thereto by the patient. For example, prescription psychotherapeutic agents or other may be delivered in quantities and according to a schedule that avoids or minimizes the likelihood of addiction or abuse. Often patient compliance with antipsychotic medications is a challenge. The material delivery device described and claimed herein may be used to deliver psychotherapeutic medications to ensure patient compliance. For example, with patients whose future compliance with physician advice regarding medication administration may be of concern, drug compliance can be assured by utilization according to a schedule of the material delivery device described and claimed herein. Drug delivery schedules suitable for use with the material delivery device may be those that are pre-established, for example, by a physician, or by the patient according to a model or preset guidelines. In addition, a drug delivery schedule may be established according to a particular measurement, for example, a measurement made by a physiological sensor such as those described herein. Examples of some of the most widely prescribed psychotherapeutic medicines include escitalopram (brand name: Lexapro®) citalopram (brand name: Celexa®), fluoxetine (brand name: Prozac®), paroxetine (brand name: Paxil®) and setraline (brand name: Zoloft®). Therapeutic agents for treating anxiety disorders such as Generalized Anxiety Disorder, Obsessive-Compulsive Disorder (OCD), Panic Disorder, Post-Traumatic Stress Disorder (PTSD), and Social Phobia (or Social Anxiety Disorder) are examples of those that can be administered using the material delivery device described and claimed herein. Other psychotherapeutic agents for use with the device described and claimed herein include, but are not limited to, Clozaril® (clozapine), Haldol® (haloperidol), Loxitane® (loxapine), Mellaril® (thioridazine), Moban® (molindone), Navane® (thiothixene), Prolixin® (fluphenazine), Risperdal® (risperidone), Serentil® (mesoridazine), Stelazine® (trifluoperazine), Thorazine® (chlorpromazine), Trilafon® (perphenazine), and Zyprexa® (olanzapine).

As described herein, the system may be used to deliver any delivery material singularly or in combination with at least one other delivery material. Combination therapy comprising multiple delivery materials can be designed to deliver the materials sequentially or concomitantly, or singularly but on different time schedules.

The term “delivery fluid” as used herein, refers to delivery materials having any form that exhibits fluid or fluid-like behavior, including liquids, or other solid particles in a liquid carrier. The delivery fluid may be a solution, suspension/gel, fluidized powder, or emulsion.

In the embodiment of FIG. 1, delivery system 10 includes material delivery device 12 located in an environment 14, (which in this particular example is a human body) and remote controller 16. As used herein, the term “remote” means the transmission of information (e.g. data or control signals) or power signals or other interactions between spatially separated devices or apparatuses, such as the remote controller or the material delivery system, without a contiguous connecting element such as a wire or cable linking the remote controller and the delivery system, and does not imply a particular spatial relationship between the remote controller and the delivery device, which may, in various embodiments, be separated by relatively large distances (e.g. miles or kilometers) or a relatively small distances (e.g. inches or millimeters). Material delivery device 12 includes a responsive controllable output mechanism 18 that is responsive to a control signal generated by remote controller 16. The device may function without a remote controller to activate the controllable output mechanism. The device may contain a processor mechanism that is configured to generate and transmit at least one control signal to the controllable output mechanism 18 to control the exit of at least one material from the controllable output mechanism 18. The processor mechanism may include a memory and may be programmed in vivo remotely by remote controller 16 or may be pre-programmed prior to deployment in vivo. Any function described herein as applicable to a remote controller may be programmed into the processor of the device. Programming of such a processor is within the skill of a person in the art. The device may also include a timer, or a counter. The device may also include a mechanism that determines its internal state, and it may include a transmission mechanism for transmitting information regarding its internal state. In addition an embodiment may include an external device, or remote controller, that has the ability to determine the internal state of the material delivery device. The remote controller may include a display means for displaying any desired information regarding at least one material delivery device, including but not limited to, its function, material delivery history and schedule, material status, physiological data of the host, etc. Further embodiments of the material delivery device include aspects where the control signal that activates the controllable output mechanism can be generated and transmitted from a remote controller or from a processor mechanism contained in the device and programmed to generate and transmit a control signal.

Figure 2:
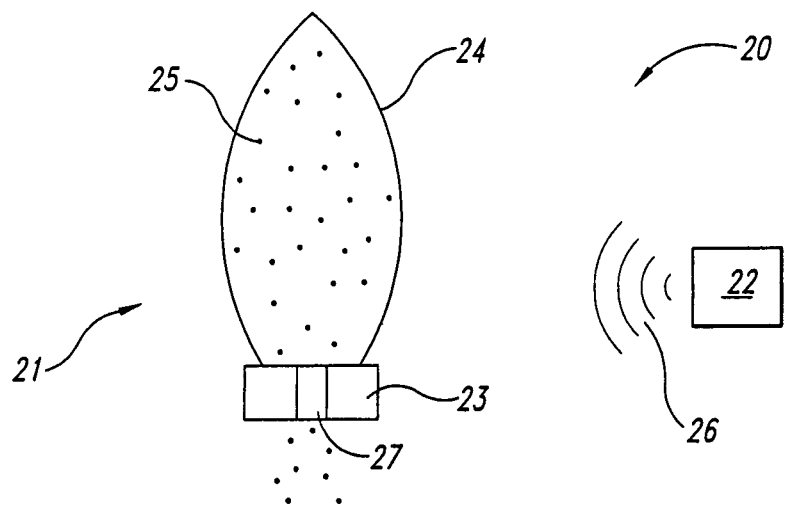
FIG. 2 depicts an embodiment of a delivery system including a remote controller.

FIG. 2 depicts an embodiment of a material delivery system 20 including a material delivery device 21 controlled by remote controller 22. In the embodiment of FIG. 2, material delivery device 21 includes controllable output mechanism 23 and deformable reservoir 24 which contains delivery material 25. Remote controller 22 transmits a control signal 26 to the responsive controllable output mechanism 23 to control the exit of the material 25 from the deformable reservoir 24. The delivery material 25 exits from deformable reservoir 24 via outlet 27. Material delivery device 21 may also include a body structure further described herein.

Figure 3:
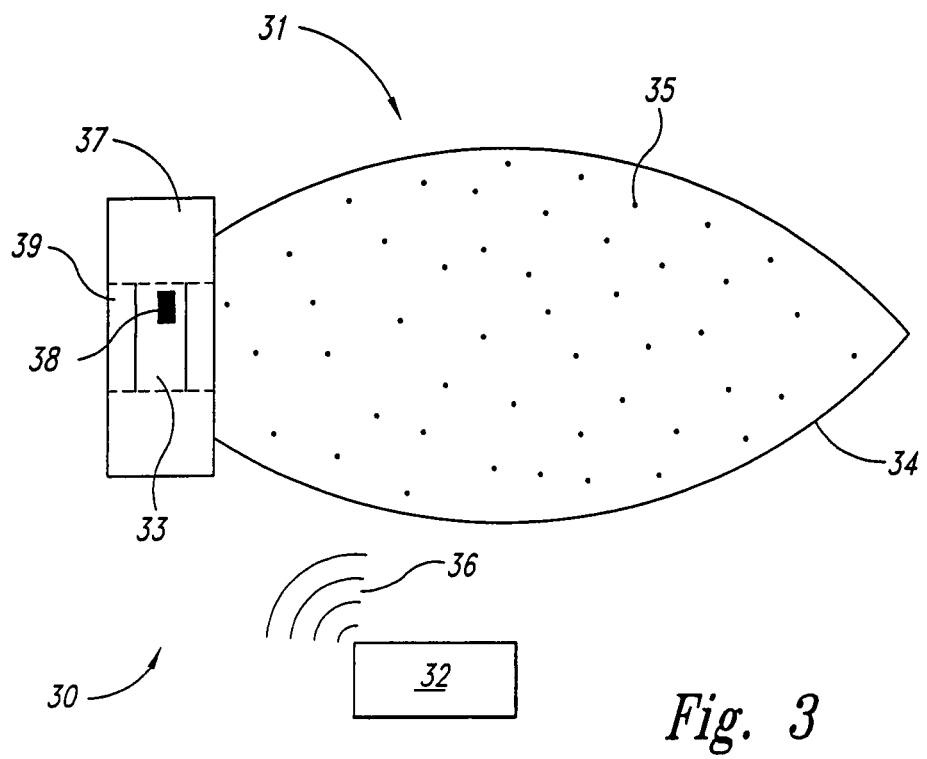
FIG. 3 depicts another embodiment of a delivery system including a remote controller.

FIG. 3 depicts another embodiment of a delivery system 30 including a deliver device 31 controlled by remote controller 32. In the embodiment of FIG. 3, delivery device 31 includes pump 33 and delivery reservoir 34, which contains delivery material 35. Remote controller 32 transmits control signal 36 to the at least one controllable output mechanism 37 to control the rate of exit of the delivery material 35 from the reservoir. Remote controller 32 also transmits control signal 36 to receiving element 38 in pump 33 to control the pumping of delivery material 35 from delivery reservoir 34. Outlet 39 and controllable output mechanism 37 are also included in delivery device 31. In various embodiments, the control signal may be electromagnetic, mechanical/acoustic or ultrasonic.

FIG. 4 illustrates in schematic form a material delivery device 40 comprising a delivery reservoir 41 configured to contain a delivery material, the delivery reservoir having at least one outlet 42 through which the delivery material may exit the delivery reservoir; a delivery material 43 contained within the delivery reservoir 41; and at least one controllable output mechanism 44 adapted for controlling the exit of material from the reservoir into the environment, e.g., a valve. Delivery material may exit delivery reservoir 41 by controlled diffusion, or by being moved out of delivery reservoir 41 by positive pressure applied to delivery reservoir 41 (e.g. by a pump, or pressure exerted by the contraction forces 45 created by the expanded deformable reservoir, or by a pressurizing means associated with the reservoir such as a gas-filled bladder or an osmotic mechanism).

To modulate, or vary, the rate of exit or release of delivery material, the at least one controllable output mechanism used in this and other embodiments is operably linked to the at least one outlet of the at least one delivery reservoir. In some embodiments, the controllable output mechanism may be fixed to, or sealed to, the reservoir by any conventional, non-biodegradable means, such as, for example a biocompatible adhesive. The at least one controllable output mechanism is placed in communication with the at least one outlet such that the exit of the at least one material from the at least one reservoir may be controlled by the controllable output mechanism. The process of operably linking the controllable output mechanism to the outlet of the reservoir may take place prior to disposition of the device within the delivery device, e.g., a hypodermic needle, as further described herein. The term "variably control" as sometimes used herein with respect to the controllable output mechanism means having the ability to determine and set various parameters associated with the exit of material from the at least one reservoir. In one embodiment, to "variably control" may mean to maintain a substantially constant steady rate of emission. In other embodiments, to "variably control" may mean to stop the exit or release of material from the at least one reservoir for an interval of time, while allowing the exit of material from the at least one reservoir during other intervals of time. In still other embodiments, to "variably control" may mean to adjust the rate of exit of material from the at least one reservoir over a period of time. The rate of exit of material may vary depending on sensed conditions (as described herein), or according to a control signal received from an external source.

The at least one controllable output mechanism may have various functional characteristics. In some embodiments, the controllable output mechanism may include or form a heating element (e.g., a resistive element) or a cooling element (which may be, for example, a thermoelectric device). In some embodiments, the controllable output mechanism may be an expanding element. In some embodiments, a controllable output mechanism may include a receiving element such as an antenna or other geometric gain structure to enhance the receiving of an electromagnetic control signal transmitted from a remote control signal generator. As that term is used herein, "electromagnetic control signal" means a control signal that has electric characteristics, magnetic characteristics, or has characteristics of both. The response of the controllable output mechanism to an electromagnetic field may be due to absorption of energy from the electromagnetic signal or due to torque or traction on all or a portion of the controllable output mechanism due to the electromagnetic field. The response will depend upon the intensity, the relative orientation and the frequency of the electromagnetic field and upon the geometry, composition and preparation of the material of the controllable output mechanism. A response may occur on the macro level, on a microscopic level, or on a nanoscopic or molecular level. In some embodiments, the controllable output mechanism may respond to the control signal by changing shape. In some embodiments, the controllable output mechanism may respond to the control signal by changing in at least one dimension. The response of the controllable output mechanism may include one or more of heating, cooling, vibrating, expanding, stretching, unfolding, contracting, deforming, softening, or folding globally or locally. In some embodiments, the controllable output mechanism may be configured to selectively respond to an electromagnetic field having a specific frequency and/or orientation. Frequency selectivity may be conferred by appropriate selection of controllable output mechanism size or shape relative to the frequency of the electromagnetic signal, while directional selectivity may be conferred by the configuration and orientation of the controllable output mechanism.

Controllable output mechanisms used in various embodiments of delivery devices and systems described herein may include one or more electromagnetically active materials. The controllable output mechanism may include a magnetically or electrically active material. Examples of magnetically active materials include, but are not limited to, permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as silicate or sulfide, and antiferromagnetic materials such as canted antiferromagnetic materials which behave similarly to ferromagnetic materials. Examples of electrically active materials include, but are not limited to, ferroelectrics, piezoelectrics, dielectric materials, including permanently 'poled' dielectrics and dielectrics having both positive and negative real permittivities, and metallic materials.

Controllable output mechanisms may include materials that change size or shape when thermal energy is applied. By combining materials as in polymer gels one can use the differing properties of individual components to affect the whole. Thermally-responsive materials include thermally responsive gels (hydrogels) such as thermosensitive N-alkyl acrylamide polymers, Poly(N-isopropylacrylamide) (PNIPAAm), biopolymers, crosslinked elastin-based networks, materials that undergo thermally triggered hydrogelation, memory foam, resin composites, thermochromic materials, proteins, memory shape alloys, plastics, and thermoplastics. Materials that contract or fold in response to heating may include thermally-responsive gels (hydrogels) that undergo thermally triggered hydrogelation (e.g. Polaxamers, uncross-linked PNIPAAm derivatives, chitosan/glycerol formulations, elastin-based polymers), thermosetting resins (e.g. phenolic, melamine, urea and polyester resins), dental composites (e.g. monomethylacrylates), and thermoplastics.

In some embodiments, the controllable output mechanism may include a polymer, ceramic, dielectric, or metal. The controllable output mechanism may include various materials, such as polymers, ceramics, plastics, dielectrics or metals, or combinations thereof. In some embodiments, the controllable output mechanism may include a polymer and a magnetically or electrically active component. In some embodiments, the controllable output mechanism may include a shape memory material such as a shape memory polymer or a shape memory metal, or a composite structure such as a bimetallic structure.

In some embodiments, the controllable output mechanism may include a polymer and an electrically active component (including highly polarizable dielectrics) or a magnetically active component (including ferropolymers and the like). In embodiments in which the controllable output mechanism includes one or more electrically or magnetically active components, the electrically or magnetically active component may respond to an electromagnetic control signal in a first manner (e.g., by heating) and the response of the controllable output mechanism may be produced in response to the electrically or magnetically active component (e.g. expansion or change in shape in response to heating of the electrically or magnetically active component). Controllable output mechanisms may, in some embodiments, be composite structures.

Controllable output mechanisms may, in some embodiments, include microfluidic devices prepared by microfabrication. In addition, a reversible valve based on an "artificial muscle" can be utilized to control the flow of delivery material from the expandable delivery reservoir to the environment. Such valves are described and known to those skilled in the art, see for example, Low, L., Seetharaman, S., He, K., Madou, M. J., 2000, "Microactuators toward microvalves for responsive controlled drug delivery", *Sens. Actuators B* 67, 149-160, which is incorporated herein by reference. The term "artificial muscle" refers to a chemomechanical actuator composed of a blend of a hydrogel and an electronically conducting redox polymer, for example, polyaniline and polypyrrole, or their derivatives. Alternatively, another embodiment includes an electroactive polymeric actuator based on acrylic acid, acrylamide and polypyrrole/carbon black composite. This polymeric actuator acts as an artificial muscle, bending on demand under the application of low voltage with a fast response time. See for example, "Responsive Drug Delivery Systems" Sapna Deo, Patricia Eisenhardt, Elizabeth Moschou, Serban Peteu, Leonidas Bachas, Marc Madou, Sylvia Daunert, *Analytical Chemistry,* 2003, 75 (9) 206A-213A; and Madou, M. J., Florkey, J., 2000, "From batch to continuous manufacturing of microbiomedical devices", *Chem. Rev.* 100, 2679-2692; and U.S. Patent Publication 2004/0182704; each of which is incorporated herein by reference. Induced to swell by an electrical bias, the polymer is controllable, and therefore, the polymer can be swollen and shrunk to close and open a valve using electrical control. In other embodiments, microvalves and micropumps can be utilized that comprise electrically-responsive hydrogel systems for actuation. See for example, Beebe, D. J., Moore, J. S., Bauer, J. M., Yu, Q., Liu, R. H., Devadoss, C., Jo, B., 2000, "Functional hydrogel structures for autonomous flow control inside microfluidic channels", *Nature* 404, 588-590; and U.S. Pat. No. 6,663,821 for "Bistable Microvalve", each of which is incorporated herein by reference. The micropumps and microvalves discussed above can be applied to the drug delivery systems described herein to control the flow of delivery material from the expandable delivery reservoir to the environment.

FIG. 5 depicts an example of a controllable output mechanism 50 including a composite structure formed from a polymer 51 and multiple electrically or magnetically active components in the form of multiple particles 52 distributed through polymer 51. In some embodiments, the electrically or magnetically active components may be heatable by the electromagnetic control signal, and heating of the electrically or magnetically active components may cause the polymer to undergo a change in configuration. An example of a magnetically responsive polymer is described, for example, in Neto, et al, "Optical, Magnetic and Dielectric Properties of Non-Liquid Crystalline Elastomers Doped with Magnetic Colloids"; Brazilian Journal of Physics; bearing a date of March 2005; pp. 184-189; Volume 35, Number 1, which is incorporated herein by reference. Other examples of materials and structures are described in Agarwal et al., "Magnetically-driven temperature-controlled microfluidic actuators"; pp. 1-5; located at: http://www.unl.im.dendai.ac.jp/INSS2004/INSS2004_papers/OralPresentations/C2.pdf or U.S. Pat. No. 6,607,553, both of which are incorporated herein by reference.

An embodiment of a material delivery device may include at least one controllable output mechanism that includes a pump for pumping delivery material, e.g., a fluid, from the delivery reservoir, and in particular when the reservoir is unpressurized. Alternatively, in some cases the delivery material, e.g., a fluid, may simply diffuse out of the delivery device. Various types of pumps may be used, without limitation. Suitable pumps may include, for example, micropump (nanopump), microosmotic, mechanical, displacement, centrifugal, and peristaltic pumps.

FIG. 6 illustrates an embodiment of a delivery device that includes an osmotic pump. Delivery device 60 includes delivery reservoir 61, which contains delivery material 272 and may have a controllable output mechanism 63 including an outlet. Controllable output mechanism 63 is operably linked to delivery reservoir 61 to control the flow of the delivery material from the reservoir. Osmotic pump 64 includes osmotic chamber 65 containing osmotic pressure generating material 66. Semi-permeable membrane 67 is permeable to osmotic fluid 68 but not to osmotic pressure generating material 66. Osmotic fluid 68 thus flows into osmotic chamber 65. This causes movable impermeable barrier 69 (which may be a rigid movable barrier or a flexible membrane) to move into delivery reservoir 61, thus pumping delivery material 272 out of the outlet included in controllable output mechanism 63. Activation of controllable output mechanism 63 may cause delivery material to exit from the reservoir.

Various different osmotic pressure-generating materials may be used in delivery systems as described herein. For example, the osmotic pressure-generating material may include ionic and non-ionic water-attracting or water absorbing materials, non-volatile water-soluble species, salts, sugars, polysaccharides, polymers, hydrogels, osmoopolymers, hydrophilic polymers, and absorbent polymers, among others. Water-attracting materials may include non-volatile, water-soluble species such as magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, various monosaccharides, oligosaccharides and polysaccharides, such as sucrose, glucose, lactose, fructose, desxtran, and mixtures thereof. Water absorbing materials include osmoopolymers, for example hydrophilic polymers that swell upon contact with water. Examples of water-absorbing materials include poly(hydroxyl alkyl methacrylates) MW 30,000-5,000,000, polyvinylpyrrolidone MW 10,000-360,000, anionic and cationic hydrogels, polyelectrolyte complexes, poly(vinyl alcohol) having low acetate residual, optionally cross linked with glyoxal, formaldehyde, or glutaraldehyde and having a degree of polymerization of 200 to 30,000, mixtures of e.g., methylcellulose, cross linked agar and carboxymethylcellulose; or hydroxypropyl methylcellulose and sodium carboxymethylcellulose; polymers of N-vinyllactams, polyoxyethylene polyoxypropylene gels, polyoxybutylene-polyoxyethylene block copolymer gels, carob gum, polyacrylic gels, polyester gels, polyuria gels, polyether gels, polyamide gels, polypeptide gels, polyamino acid gels, polycellulosic gels, carbopol acidic carboxy polymers MW 250,000-4,000,000, cyanamer polyacrylamides, cross-linked indene-maleic anhydride polymers, starch graft copolymers, acrylate polymer polysaccharides. Other water attracting and/or water absorbing materials include absorbent polymers such as poly(acrylic acid) potassium salt, poly(acrylic acid) sodium salt, poly(acrylic acid-co-acrylamide) potassium salt, poly(acrylic acid) sodium salt-graft-poly(ethylene oxid), poly(2-hydroxethyl methacrylate) and/or poly(2-hydropropyl methacrylate) and poly(isobutylene-co-maleic acid). A variety of osmotic pressure-generating materials and/or water-absorbing materials are described in U.S. Patent Publications 2004/0106914 and U.S. 2004/0015154, both of which are incorporated herein by reference in their entirety.

The osmotic pressure-generating ability of the osmotic pressure-generating material may depend on the solubility of the osmotic pressure-generating material in the osmotic fluid, and/or upon the concentration of the osmotic pressure-generating material in the osmotic fluid, and varying either concentration or solubility may modify the osmotic-pressure generating ability of the osmotic pressure-generating material. Concentration of the osmotic pressure-generating material in the osmotic fluid may be modifiable by a change in solubility of the osmotic pressure-generating material in response to an electromagnetic field control signal or by a change in the osmotic fluid in response to an electromagnetic field control signal.

Figure 7A:
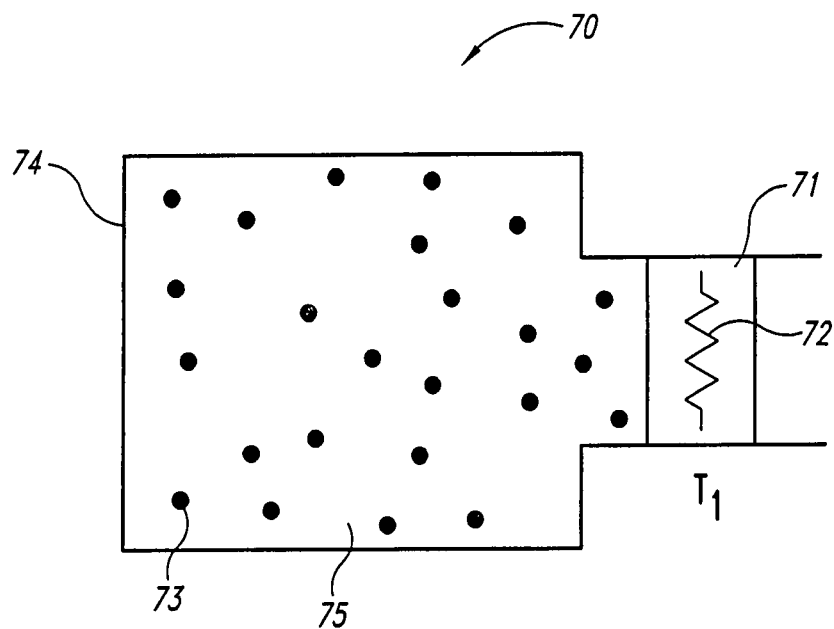
FIGS. 7A and 7B illustrate an embodiment where the conformation or shape of a controllable output mechanism changes in response to a control signal.
Figure 7B:
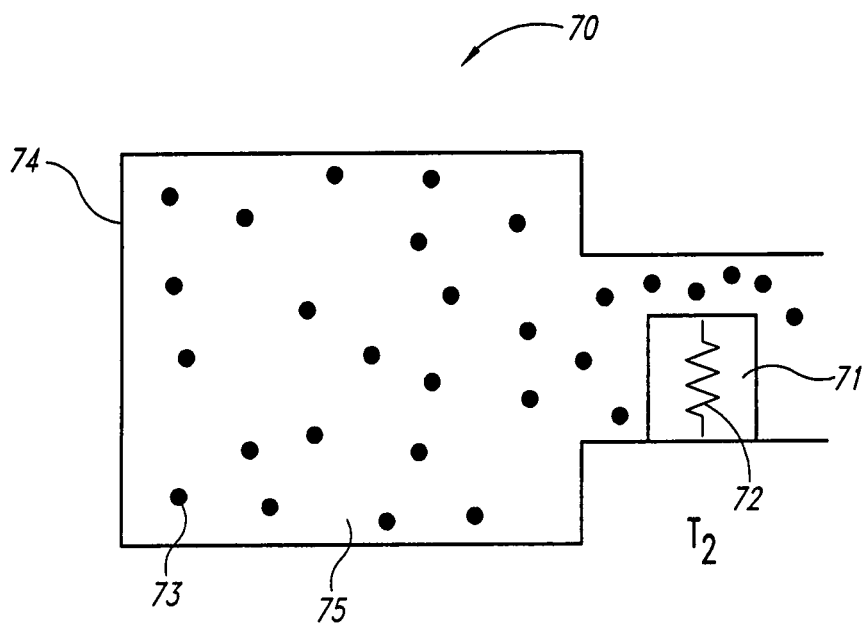

FIGS. 7A and 7B depict an embodiment of a delivery device 70 in which the at least one controllable output mechanism 71 includes an electromagnetic field responsive control element 72 that may respond to the control signal by producing heat. Delivery material 73 is contained within delivery reservoir 74 in delivery medium 75. Controllable output mechanism 71 has an initial temperature $T_1$. Following heating of controllable output mechanism 71 in response to an electromagnetic control signal, controllable output mechanism 71 has a subsequent temperature $T_2$, as shown in FIG. 7B ($T_1 < T_2$). The change in temperature of controllable output mechanism 71 may modify the shape, conformation or geometry of the controllable output mechanism causing the delivery material 73 to exit the delivery reservoir 74. The electromagnetic field responsive control element 72 may include a ferrous, ferric, or ferromagnetic material, or other material with a significant electromagnetic "loss tangent" or resistivity. As in previously described embodiment, delivery device may also include a pump and an outlet.

Figure 8A:
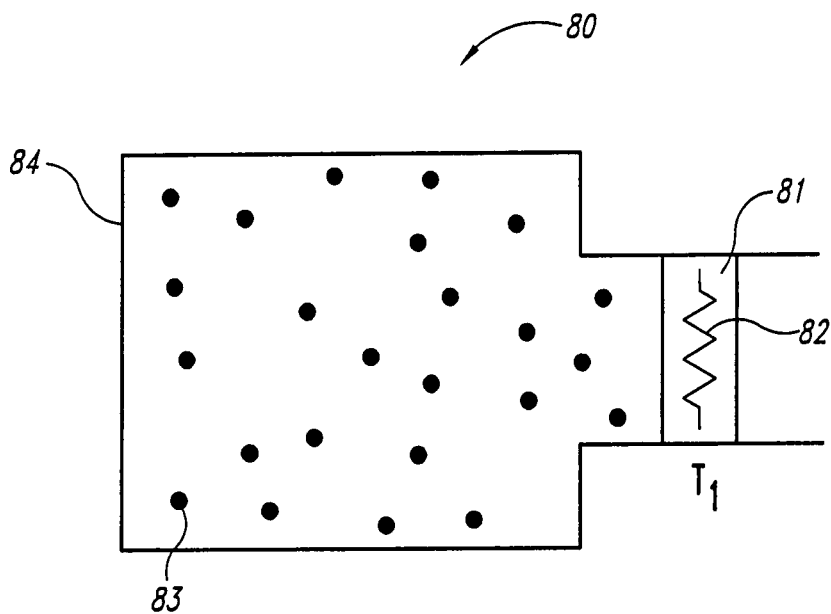
FIGS. 8A and 8B illustrate an embodiment where the conformation or shape of a controllable output mechanism changes in response to a control signal.
Figure 8B:
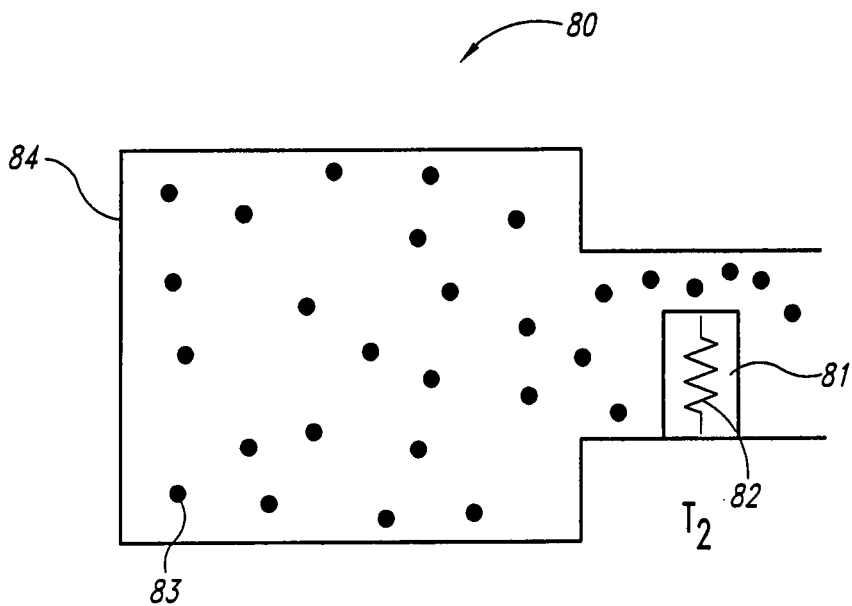

FIGS. 8A and 8B depict another embodiment of a delivery device 80, in which the at least one controllable output mechanism 81 may include an electromagnetic field responsive control element 82. The electromagnetic field responsive control element 82, in response to an electromagnetic control signal, may cool in temperature (from $T_1$ to $T_2$, where $T_1 > T_2$) and may cause the controllable output mechanism to modify its shape or geometry creating an outlet and causing the delivery material 83 to exit the reservoir 84. The electromagnetic field responsive control element 82 may include a thermoelectric element, for example. Methods and/or mechanisms of producing cooling may include, but are not limited to, thermoelectric (Peltier Effect) and liquid-gas-vaporization (Joule-Thomson) devices, or devices which employ "phase-changing" materials or systems involving significant enthalpies of transition.

Figure 9A:
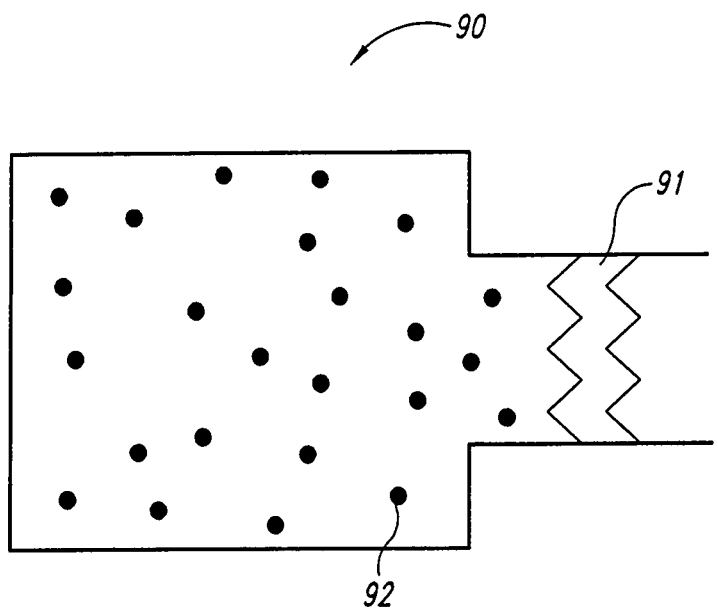
FIGS. 9A and 9B illustrate an embodiment where the shape or geometry of a controllable output mechanism changes in response to a control signal.
Figure 9B:
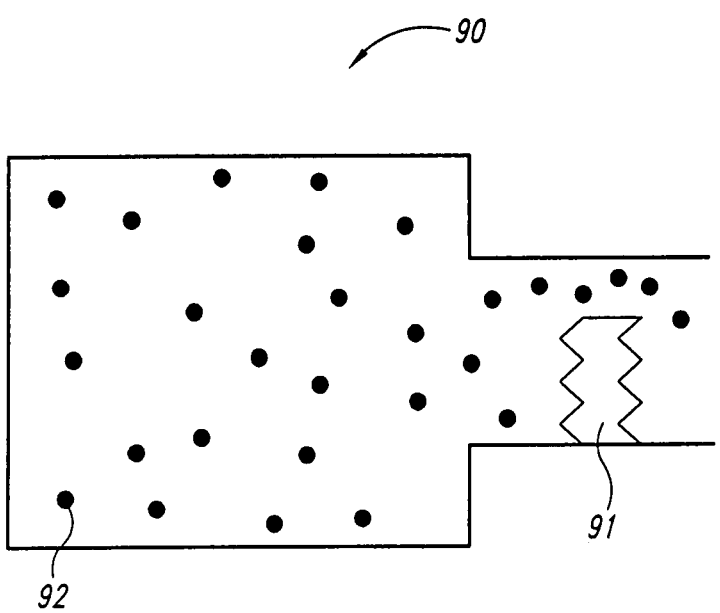

In some embodiments of the delivery device, the at least one controllable output mechanism may be a shape-changing structure that changes in at least one dimension in response to an electromagnetic control signal. FIGS. 9A and 9B depict delivery device 90 holding delivery material 92 and that includes a controllable output mechanism 91 that is a shape-changing structure. Other embodiments that utilize shape-changing materials are also contemplated. A shape-changing structure may include a polymeric material, a ferropolymer, a hydrogel, a bimetallic structure, or a shape memory material. In some embodiments, the shape-changing structure may be an expanding or contracting structure, wherein the change in at least one dimension includes an expansion or contraction in at least one dimension.

Figures 10A, 10B:
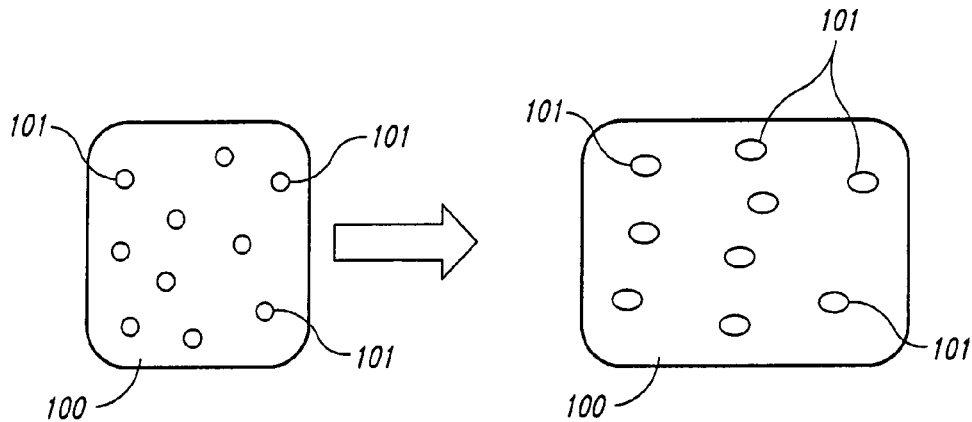
FIGS. 10A and 10B illustrate an embodiment where the controllable output mechanism changes shape in response to a control signal.

FIGS. 10A and 10B depict a controllable output mechanism 100 that expands in response to an electromagnetic control signal, with a corresponding increase in size of pores 101 in FIG. 10B relative to the size of pores 101 in FIG. 10A.

In this and other embodiments, the delivery device may include at least one biocompatible sensor for detecting at least one parameter from the at least one delivery reservoir. For example, the sensor may detect a quantity or concentration of delivery fluid in the delivery reservoir. In other embodiments, the delivery device may include at least one biocompatible sensor for detecting at least one parameter of the environment. For example the sensor may detect the presence of, or a concentration or activity of a chemical or biological molecule or cell within at least a portion of an environment surrounding the delivery device. Examples of sensors are described in, U.S. Pat. No. 6,935,165, and U.S. Patent Publications 2004/0007051 and 2005/0208469, each of which are incorporated herein by reference. Further examples of sensors are described in "Easy-to-Make Nanosensors: Tiny electronics-based detectors could provide, simple tests for cancer or bioterror agents." by Kevin Bullis, located at http://www.technologyreview.com/Nanotech/18127/which is incorporated herein by reference. Other examples of sensors are described by Gruner, G., "Carbon Nanotube Transistors for Biosensing Applications"; *Anal. Bioanal. Chem.* (2006) 384: 322-335, which is incorporated herein by reference. Carbon nanotube transistors are readily adapted for large scale manufacture as described by Gabriel, J C., *Mat. Res. Soc. Symp. Proc.*, (2003) Vol. 776,Q.12.7.1-12.7.7, which is incorporated herein by reference.

Figure 11:
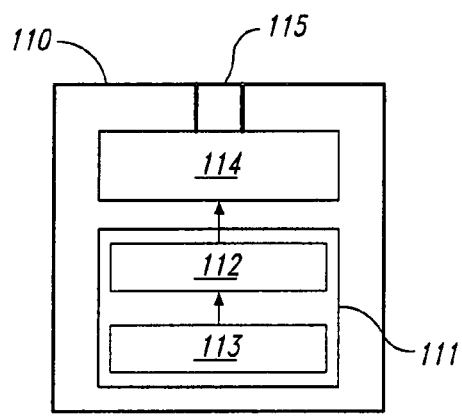
FIG. 11 depicts an example of an embodiment including a power-receiving structure.

FIG. 11 depicts in schematic form an embodiment of a delivery device 110 including a controllable output mechanism 111 that includes an active portion 112 and a power-receiving structure 113. Delivery device also includes delivery reservoir 114 and outlet 115. Power-receiving structure 113 may be any structure that has a size, shape, and material that is suitable for receiving and transducing electromagnetic energy of a particular frequency or frequency band. The power-receiving structure may include an antenna. The power-receiving structure may include a resonant structure. The resonant structure may be a resonant circuit, resonant electromagnetic structure, a molecular bond, or a mechanically resonant structure. In some embodiments, power-receiving structure 113 may be highly frequency-selective, while in other embodiments it may react usefully over a wide frequency band, or over multiple frequency bands. Power-receiving structure 113 may be formed of various metallic or electrically or magnetically active materials. Active portion 112 may include various materials that respond mechanically, thermally or chemically to electromagnetic energy received and transduced by power-receiving structure 113 to influence the effective concentration of primary material in delivery reservoir. Power-receiving structure 113 may include a mechanism that converts mechanical energy (e.g., kinetic) into electrical energy. Energy extraction from vibrations is based on the movement of a "spring-mounted" mass relative to its support frame. Mechanical acceleration is produced by vibrations that in turn cause the mass component to move and oscillate (thereby creating kinetic energy). This relative displacement causes opposing frictional and damping forces to be exerted against the mass, thereby reducing and eventually extinguishing the oscillations. The damping forces literally absorb the kinetic energy of the initial vibration. This energy can be converted into electrical energy via an electric field (electrostatic) or a magnetic field (electromagnetic). While this may be the physical construct, analogs such as MEMS resonators, resonant piezoelectric structures, or similar may operate via similar physical phenomena. Additionally, non-resonant mechanical energy extraction can be implemented in a number of manners, including winding mechanisms such as those found in self-winding wristwatches, ratcheting mechanisms, or other approaches to converting input energy into either dynamic energy, potential energy, heat or other useful forms.

Figure 12:
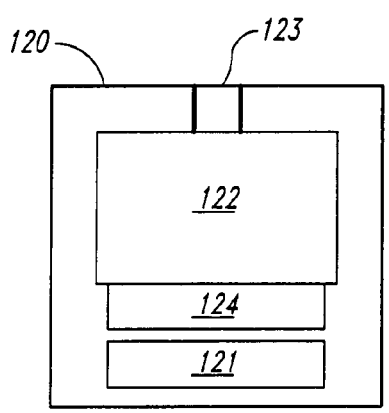
FIG. 12 depicts an example of an embodiment including a RFID structure.

FIG. 12 depicts an embodiment of a delivery device 120 including an RFID 121. Delivery device 120 includes delivery reservoir 122, outlet 123 and controllable output mechanism 124. RFID 121 may store a unique identification code that allows delivery device 120 to be identified by a remote controller (not shown) that includes RFID detection circuitry. This provides for selective control of particular delivery devices, for example. Similar means may be employed to validate the identity of the external controller to the control circuitry of the at least one delivery device.

Delivery devices as described herein may be configured for use in a variety of in vivo environments. A delivery device of the type disclosed herein may include a biocompatible body structure adapted for positioning in a body of an animal, and for receiving the material delivery device as depicted in FIG. 1. The body structure may be deployed in advance of the deployment of the material delivery device, followed by deployment of the material delivery device therein; or the body structure may be deployed in conjunction with the deployment of the material delivery device. A body structure may include biocompatible materials and may be of any shape that is capable of receiving the material delivery device. The body structure may be flexible or rigid and may be of any shape to provide a barrier between the material delivery device and surrounding tissue. Following optional removal of the material delivery device from the in vivo environment, as further described herein, the body structure may receive a new material delivery device, or may be degraded by the insertion of a specific biocompatible degrading means (e.g., a fluid-carried degrading material) into the body structure, or it may biodegrade naturally after a time-interval.

The material delivery device may be used in a body of a human or other animal and thus would typically have suitable biocompatibility characteristics. Further, the delivery device may include features that allow it to be placed or positioned in a desired location in the environment, or targeted to a desired location in the environment. Such features may include size and shape features, tethers or gripping structures to prevent movement of the body structure in the environment (in the case that the device is placed in the desired location) or targeting features (surface chemistry, shape, etc.) that may direct the device toward or cause it to be localized in a desired location. The body structure may include a tissue-specific marker or targeting molecule. For example, the tissue specific marker or targeting molecule may be a tissue specific endothelial protein. The delivery device as may be used for placement in the body of an animal may be constructed using methods known to those in skill of the art of microfabrication, rendering the device suitable for transcutaneous emplacement via a hypodermic needle.

In some embodiments, the delivery device may be a MEMS (micro-electromechanical system) or NEMS (nano-electromechanical system) device or other microfabricated electromechanical device. The term "MEMS" as used herein can refer to either MEMS devices, a NEMS devices, or both. The MEMS or NEMS device may be constructed from at least one metal, polymer, ceramic, glass, semiconductor material, nanotube material, or other known material conventionally used. In some embodiments, the device may be a battery-free device, powered by power beaming, inductive coupling, or an environmental power source. In still other embodiments, the device may include a battery or other on-board power source. In some embodiments, the delivery device may include an electromagnetic control signal generator, which may be located substantially in, on or adjacent to the at least one delivery reservoir. In other embodiments, the electromagnetic control signal generator may be located at a location remote from the delivery reservoir.

As described herein, a material delivery system may include a remote controller. A remote controller may be any device that is capable of selectively controlling the operation or activation of the material delivery device while the device is deployed in vivo. A remote controller may have an electromagnetic signal generator capable of producing an electromagnetic signal sufficient to activate a controllable output mechanism of a delivery device located in an animal to control the delivery of delivery material from a delivery reservoir of the delivery device; and an electromagnetic signal transmitter capable of wirelessly transmitting the electromagnetic signal to the controllable output mechanism. Various types and frequencies of electromagnetic control signals may be used in delivery systems as described herein. For example, in some embodiments, the delivery system may include a remote controller configured to generate a static or quasi-static electrical field control signal or a static or quasi-static magnetic field control sufficient to activate the controllable output mechanism to control release of the effective mass or concentration of primary material in a desired manner. In other embodiments, the remote controller may be configured to generate a radio-frequency, microwave, infrared, millimeter wave, optical, or ultraviolet electromagnetic field control signal sufficient to activate the controllable output mechanism to control the effective concentration of primary material in a desired manner. In another embodiment, the remote controller may be configured to display information to the user, via a readout or through transmission of the data or information to another device that can then print the information or data or can display the information or data.

Figure 13:
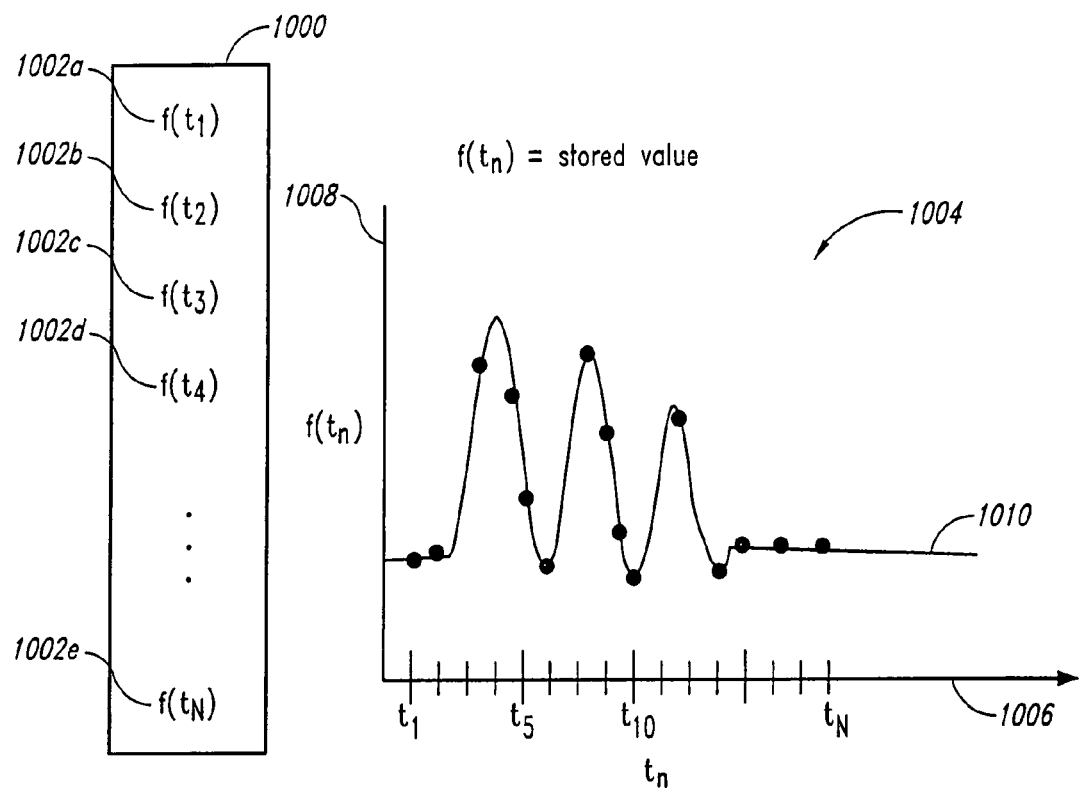
FIG. 13 illustrates a control signal generated from stored pattern data.

The control signal may be produced based at least in part upon a predetermined activation pattern. As shown in FIG. 13, a predetermined activation pattern may include a set of stored data 1002a, 1002b, 1002c, 1002d, . . . 1002e, having values $f(t1)$, $f(t2)$, $f(t3)$, $f(t4)$, . . . $f(t_N)$, stored in a memory mechanism 1000, or memory location, 1000. The activation pattern upon which the electromagnetic signal is based is depicted in plot 1004 in FIG. 13. In plot 1004, time $t_n$ is indicated on axis 1006 and signal amplitude $f(t_n)$, which is a function of $t_n$, is indicated on axis 1008. The value of the electromagnetic signal over time is represented by trace 1010. The predetermined activation pattern represented by data 1002a, 1002b, 1002c, 1002d, . . . 1002e may be based upon calculation, measurements, or any other method that may be used for producing an activation pattern suitable for activating a controllable output mechanism. Memory mechanism 1000 may be a memory location in a remote controller or located in the material delivery device. As an example, a simple remote controller may include a stored activation pattern in memory and include electrical circuitry configured to generate an electromagnetic control signal according to the pattern for a preset duration or at preset intervals, without further input of either feedback information or user data. In a more complex embodiment, a predetermined activation pattern may be generated in response to certain feedback or user input conditions.

Figure 14:
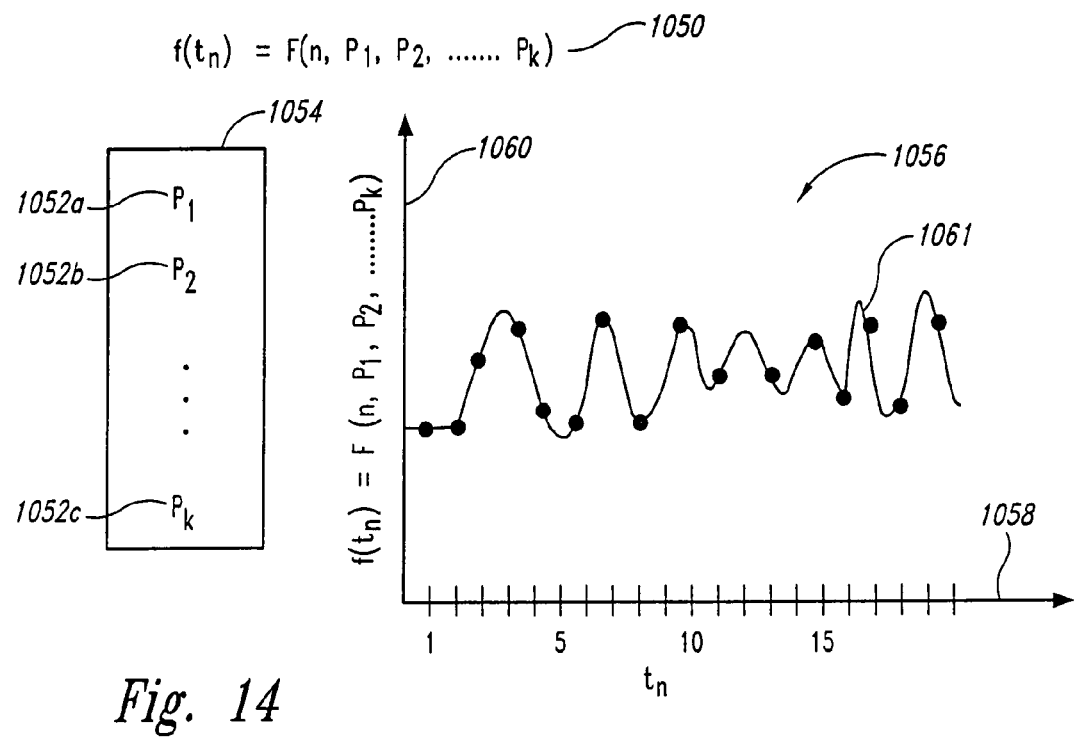
FIG. 14 illustrates a control signal calculated from a model based on stored parameters.

In some embodiments, a signal may be produced based upon a model-based calculation. As shown in FIG. 14, an activation pattern $f(t_n)$ may be a function not only of time $(t_n)$ but also of model parameters $P_1$, $P_2$, . . . $P_k$, as indicated by equation 1050. Data 1052a, 1052b, . . . 1052c having values $P_1$, $P_2$, . . . $P_k$ may be stored in memory 1054. A control signal may be computed from the stored model parameters and time information. For example, as indicated in plot 1056, time is indicated on axis 1058 and the strength or amplitude of the electromagnetic control signal is indicated on axis 1060, so that trace 1061 represents $f(t_n)$. Memory 1054 may be a memory location in a remote controller. The remote controller may generate a control signal based upon the stored function and corresponding parameters. In some embodiments, the electromagnetic control signal may also be a function of one or more feedback signals (from the delivery device or the environment, for example) or of some user input of data or instructions.

Figure 15:
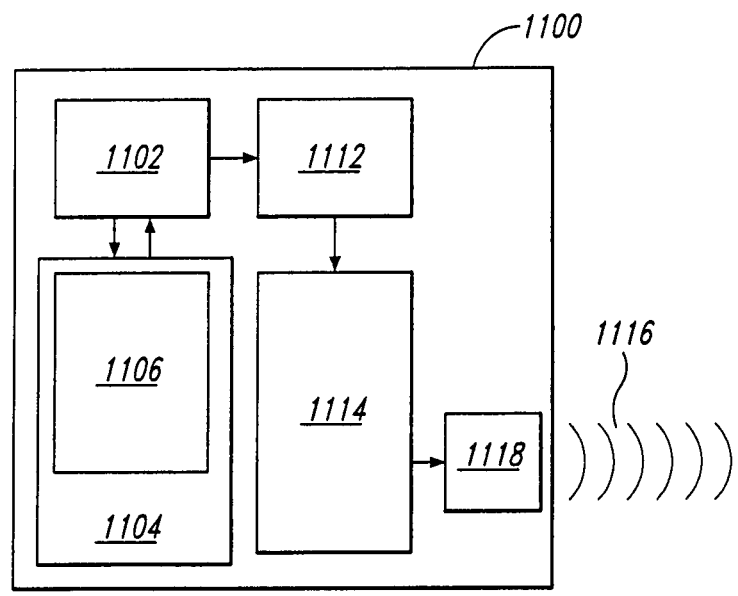
FIG. 15 is a schematic diagram of a remote controller.

FIG. 15 depicts a remote controller 1100 having a memory 1104 capable of storing pre-determined data values or parameters used in model-based calculation, as described herein. Remote controller 1100 may also include electrical circuitry 1102, signal generator 1112, and signal transmitter 1114 for transmitting control signal 1116. Memory 1104 may include memory location 1106 for containing a stored activation pattern or model parameters; portions of memory 1104 may also be used for storing operating system, program code, etc. for use by electrical circuitry 1102. The remote controller 1100 may also include a beam director 1118, such as an antenna, optical element, mirror, transducer, or other structure that may impact control of electromagnetic signaling. Remote controller 1100 may be configured to produce a control signal having various characteristics, depending upon the intended application of the system. Design specifics of electrical circuitry, signal generator, and signal transmitter will depend upon the type of electromagnetic control signal. The design of circuitry and related structures for generation and transmission of signals (e.g., electromagnetic) can be implemented using tools and techniques known to those of skill in the electronic arts. See, for example, Electrodynamics of Continuous Media, 2nd Edition, by L. D. Landau, E. M. Lifshitz and L. P. Pitaevskii, Elsevier Butterworth-Heinemann, Oxford, especially but not exclusively pp. 1-13 and 199-222, which is incorporated herein by reference, for discussion of theory underlying the generation and propagation of electrical, magnetic, and electromagnetic signals.

Remote controller 1100 may be configured to produce a control signal having various characteristics, depending upon the intended application of the system. In some embodiments, a specific remote controller may be configured to produce only a specific type of signal (e.g., of a specific frequency or frequency band) while in other embodiments, a specific remote controller may be adjustable to produce a signal having variable frequency content. Signals may include components which contribute a DC bias or offset in some cases, as well as AC frequency components. Generation of radio frequency electromagnetic signals is described, for example, in the The ARRL Handbook for Radio Communications 2006, R. Dean Straw, Editor, published by ARRL, Newington, Conn., which is incorporated herein by reference. Electromagnetic signal generator 1112 may be capable of producing an electromagnetic control signal sufficient to activate an controllable output mechanism of a delivery device located in an environment to control the flow of a delivery fluid from the delivery reservoir to the external environment, and an electromagnetic signal transmitter capable of wirelessly transmitting the electromagnetic control signal to the controllable output mechanism of a delivery device in an environment. Signal transmitter 1114 may include a sending device which may be, for example, an antenna or waveguide suitable for use with an electromagnetic signal. Static and quasi-static electrical fields may be produced, for example, by charged metallic surfaces, while static and quasi-static magnetic fields may be produced, for example, by passing current through one or more wires or coils, or through the use of one or more permanent magnets, as known to those of skill in the art. As used herein, the terms "transmit", "transmitter", and "transmission" are not limited to only transmitting in the sense of radiowave transmission and reception of electromagnetic signals, but are also applied to wireless coupling and/or conveyance of magnetic signals from one or more initial locations to one or more remote locations.

The remote controller may be modified as appropriate for its intended use. For example, it may be configured to be wearable on the body of a human (or other animal) in which a delivery device has been deployed, for example on a belt, bracelet or pendant, or taped or otherwise adhered to the body of the human. Alternatively, it may be configured to be placed in the surroundings of the animal, e.g., as a table-top device for use in a home or clinical setting.

In various embodiments, the delivery device may include a remote controller configured to generate a static or quasi-static electrical field control signal, a static or quasi-static magnetic field control signal, a radio-frequency electromagnetic control signal, a microwave electromagnetic control signal, an infrared electromagnetic control signal, a millimeter wave electromagnetic control signal, an optical electromagnetic control signal, or an ultraviolet electromagnetic control signal sufficient to activate the controllable output mechanism to control the total amount or the rate of exit of the delivery material from the delivery reservoir.

Various types of electromagnetic control signals may be used to activate the controllable output mechanism. The controllable output mechanism may be responsive to a static or quasi-static electrical field or a static or quasi-static magnetic field. It may be responsive to various types of non-ionizing electromagnetic radiation, or in some cases, ionizing electromagnetic radiation. Electromagnetic field control signals that may be used in various embodiments include radio-frequency electromagnetic radiation, microwave electromagnetic radiation, infrared electromagnetic radiation, millimeter wave electromagnetic radiation, optical electromagnetic radiation, or ultraviolet electromagnetic radiation.

The signal generator may include electrical circuitry and/or a microprocessor. In some embodiments, the electromagnetic signal may be produced at least in part according to a pre-determined activation pattern. The circuitry and/or microprocessor may be included in the material delivery device or in the remote controller. The remote controller or the material delivery device may include a memory capable of storing the pre-determined activation pattern. In some embodiments, the electromagnetic signal may be produced based on a model-based calculation; the remote controller may include a memory capable of storing model parameters used in the model-based calculation.

In some embodiments, the signal generator may produce an electromagnetic signal having one or both of a defined magnetic field strength or defined electric field strength. In general, the term field strength, as applied to either magnetic or electric fields, may refer to field amplitude, squared-amplitude, or time-averaged squared-amplitude. The electromagnetic signal may have signal characteristics sufficient to produce a change in dimension of the at least one controllable output mechanism, a change in temperature of the at least one controllable output mechanism, a change in conformation of the at least one controllable output mechanism, or a change in orientation or position of the at least one controllable output mechanism. In some embodiments, the electromagnetic signal generator may include an electromagnet or electrically-polarizable element, or at least one permanent magnet or electric. The electromagnetic signal may be produced at least in part according to a pre-programmed pattern. The electromagnetic signal may have signal characteristics sufficient to produce a change in dimension in the at least one controllable output mechanism, the change in dimension causing a delivery material to exit the at least one delivery reservoir of the delivery device. It may have signal characteristics sufficient to produce a change in temperature of the at least one controllable output mechanism, the change in temperature causing the delivery material to exit the delivery reservoir of the delivery device. In some embodiments, it may have signal characteristics sufficient to produce a change in one or more of shape, volume, surface area or configuration of the at least one controllable output mechanism, the change in dimension in one or more of shape, volume, surface area or configuration of the at least one controllable output mechanism causing the delivery material to exit the delivery reservoir of the delivery device. The electromagnetic signal may have signal characteristics sufficient to produce a change in shape in a controllable output mechanism including a shape memory material, a bimetallic structure, or a polymeric material causing the delivery material to exit the delivery reservoir of the delivery device. The electromagnetic signal may have a defined magnetic field strength or spatial orientation, or a defined electric field strength or spatial orientation.

In some embodiments, the remote controller or processor may be configured to generate and transmit an electromagnetic control signal having at least one of frequency and orientation that are selectively receivable by the at least one controllable output mechanism. In some embodiments, the remote controller may include at least one of hardware, software, or firmware configured to perform encryption of electromagnetic control signal to produce an encrypted electromagnetic control signal.

Figure 16:
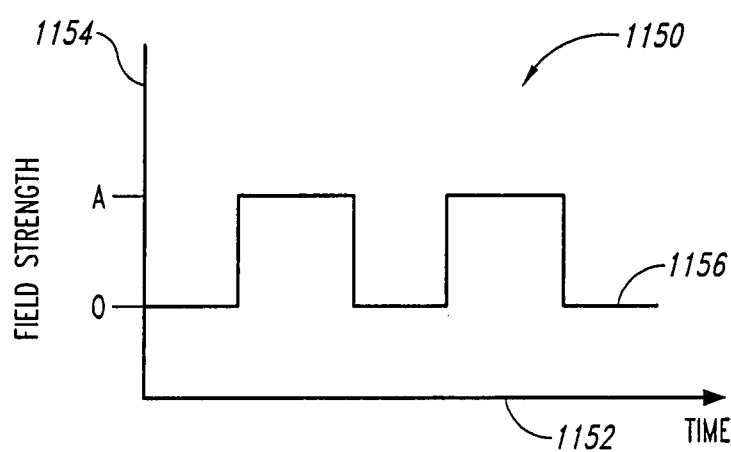
FIG. 16 depicts an example of an electromagnetic waveform.

FIG. 16 depicts an example of an electromagnetic waveform of a type that may be used to activate the at least one controllable output mechanism. In plot 1150, time is plotted on axis 1152, and electromagnetic field strength is plotted on axis 1154. Trace 1156 has the form of a square wave, switching between zero amplitude and a non-zero amplitude, A.

Figure 17:
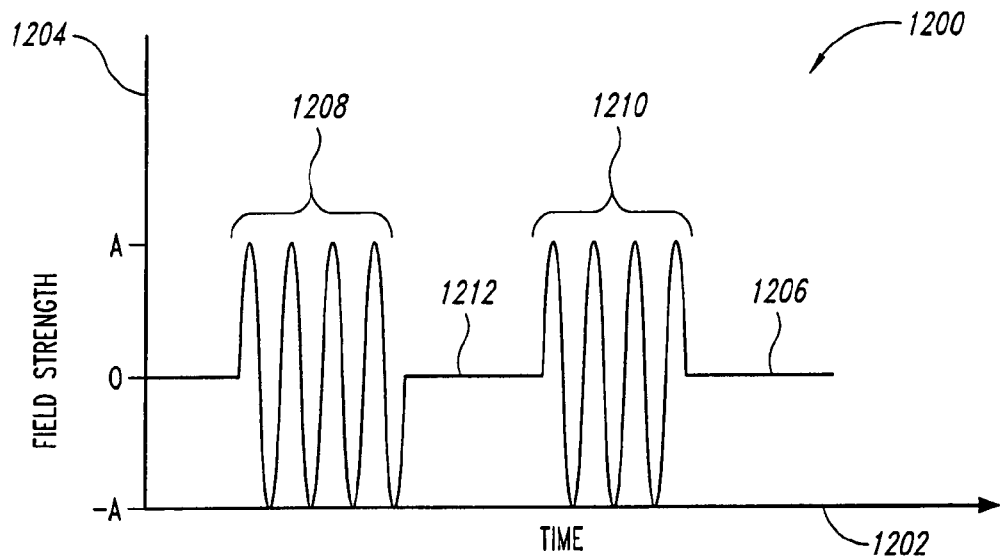
FIG. 17 depicts an example of an electromagnetic waveform.

FIG. 17 depicts another example of an electromagnetic waveform. In plot 1200, time is plotted on axis 1202, and electromagnetic field strength is plotted on axis 1204. Trace 1206 includes bursts 1208 and 1210, during which the field strength varies between A and −A, at a selected frequency, and interval 1212, during which field strength is zero.

Figure 18:
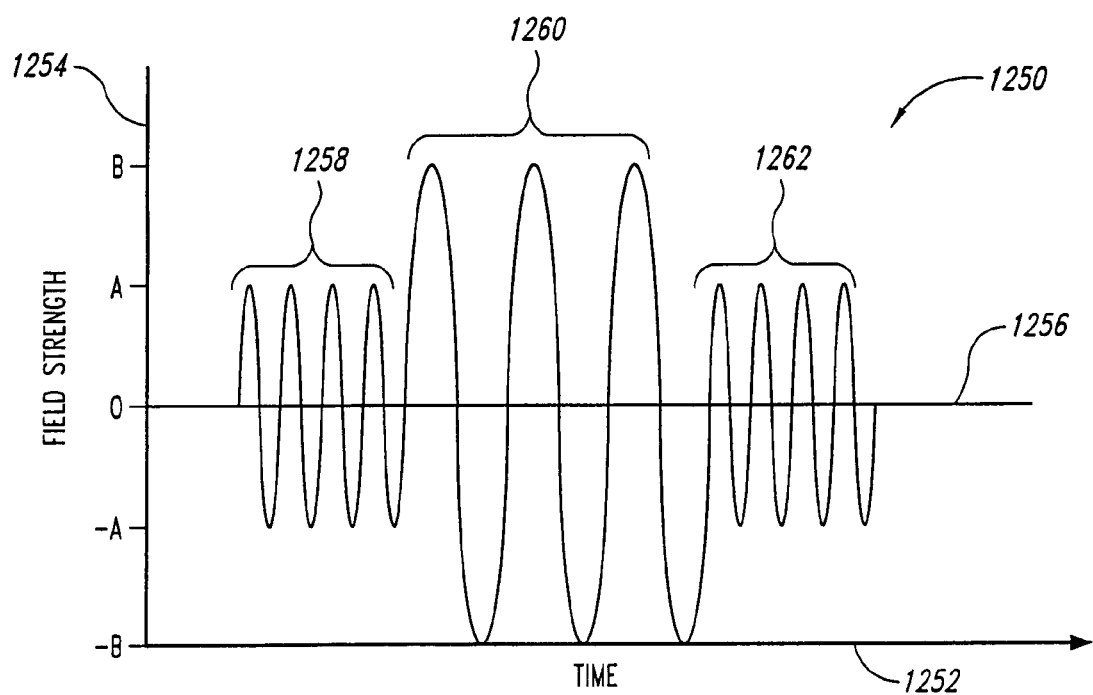
FIG. 18 depicts an example of an electromagnetic waveform.

FIG. 18 depicts another example of an electromagnetic waveform. In plot 1250, time is plotted on axis 1252, and electromagnetic field strength is plotted on axis 1254. Trace 1256 includes bursts 1258, and 1262, during which the field strength varies between A and −A at a first frequency, and burst 1260, during which the field strength varies between B and −B at a second (lower) frequency. Different frequencies may be selectively received by certain individuals or classes of controllable output mechanisms within a device or system including multiple controllable output mechanisms. An electromagnetic control signal may be characterized by one or more frequencies, phases, amplitudes, or polarizations. An electromagnetic control signal may have a characteristic temporal profile and direction, and characteristic spatial dependencies.

The magnetic or electric field control signal produced by the processor included in the material delivery device or the remote controller may have one or both of a defined magnetic field strength or defined electric field strength. At low frequencies the electrical and magnetic components of an electromagnetic field are separable when the field enters a medium. Therefore, in static and quasi-static field application, the electromagnetic field control signal may be considered as an electrical field or a magnetic field. A quasi-static field is one that varies slowly, i.e., with a wavelength that is long with respect to the physical scale of interest or a frequency that is low compared to the characteristic response frequency of the object or medium; therefore, the frequency beyond which a field will no longer be considered 'quasi-static' is dependent upon the dimensions or electrodynamic properties of the medium or structure(s) influenced by the field.

Figure 19:
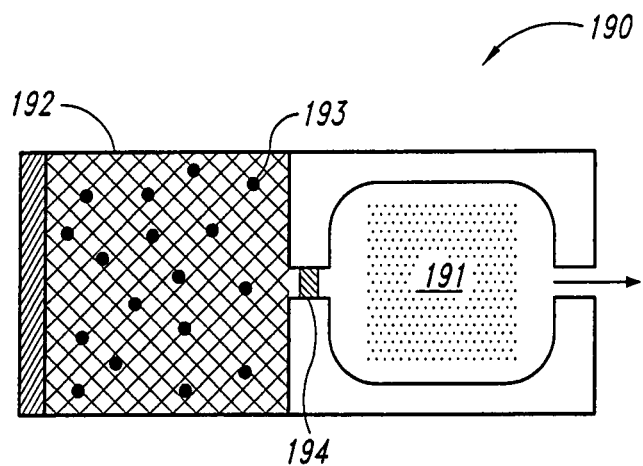
FIG. 19 illustrates an embodiment of a delivery device including a downstream fluid handling structure.

As depicted in various embodiments, the at least one material delivery reservoir may include at least one outlet through which the delivery material moves into an environment, for example by pumping or diffusion. In other embodiments, as depicted in FIG. 19, a delivery device 190 may include a downstream material handling structure 191 in communication with the delivery reservoir 192 and configured to receive material 193 ejected from the delivery reservoir 192 in response to a control signal. The downstream material handling structure 191 may include a chamber, as depicted in FIG. 19. Delivery device 190 may also include a pump (e.g., an osmotic pump) and at least one controllable output mechanism 194.

Figure 20:
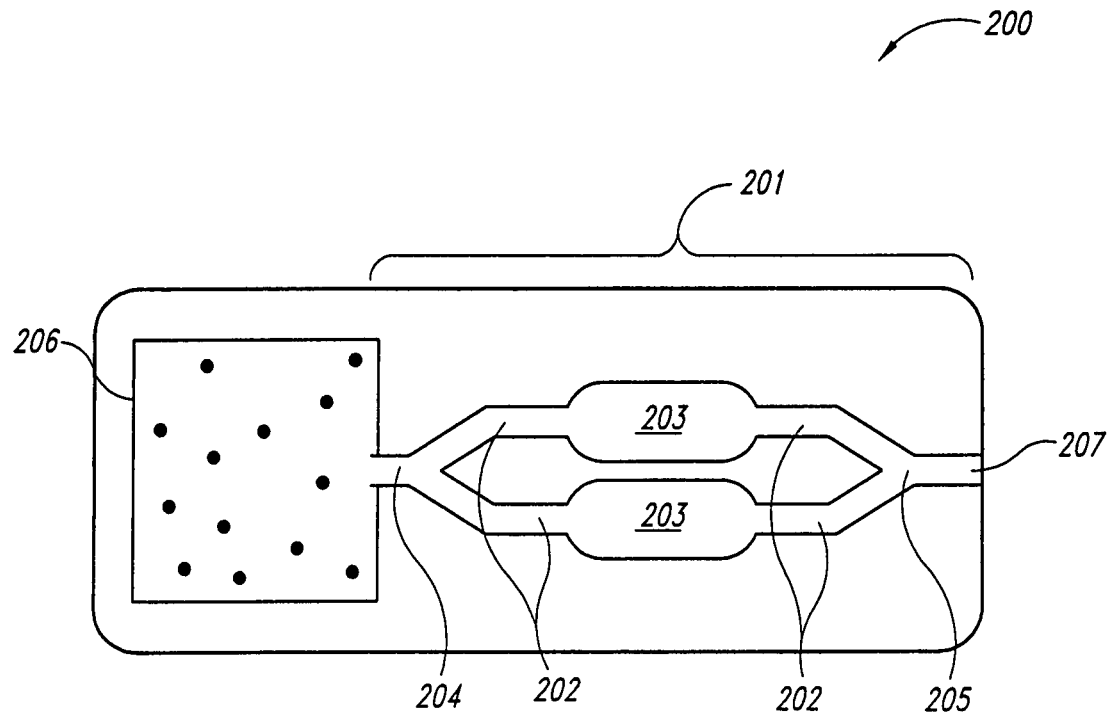
FIG. 20 illustrates another embodiment of a delivery device including a downstream fluid handling structure.

In other embodiments, e.g. delivery device 200 shown in FIG. 20, a downstream material handling structure 201 may include one or more channels 202, chambers 203, splitters 204, mixers 205, or other material handling structures, or various combinations thereof. Delivery device 200 also includes delivery reservoir 206 and outlet 207. With respect to materials that are fluids, or fluidizable, typical examples of fluid handling structures suitable for use in selected embodiments are described in U.S. Pat. Nos. 6,146,103 and 6,802,489, and in Krauβ et al., "Fluid pumped by magnetic stress"; bearing a date of Jul. 1, 2004; pp. 1-3; located at: http://arxiv.org/PS_cache/physics/pdf/0405/0405025.pdf, each of which are incorporated herein by reference. Fluid handling structures may include, but are not limited to, channels, chambers, valves, mixers, splitters, accumulators, pulse-flow generators, and surge-suppressors, among others.

Delivery material may be loaded into deformable material-containing reservoir structures having various shapes and configurations. As used herein, the term "deformable" means that the reservoir has the ability to change its shape in at least one dimension. Deformable reservoirs may be, for example, volumetrically expandable, radially-expandable, or remain volumetrically constant but be geometrically reconfigurable. In some embodiments, the deformable reservoir may be an expanding or contracting structure, wherein the change in at least one dimension includes an expansion or contraction in at least one dimension. Another embodiment is a deformable reservoir pleated along its longitudinal axis and azimuthally wrapped and sleeved, similar to an umbrella designed for compact storage or transport, in order to realize a minimal diameter for deployment (e.g., injection) when unfilled. A non-limiting example of a volumetrically expandable reservoir is a balloon-like structure. A non-limiting example of a longitudinally-reconfigurable reservoir is a microcatheter that is able to flex and negotiate a lumen of an animal. Examples of microcatheters are familiar to those of skill in the art. As described in embodiments herein, the deformable reservoir may have at least one outlet through which a material may exit the delivery reservoir to the external environment or to a downstream location. In another embodiment, the deformable reservoir may include chemically or biologically inert inner or outer surfaces. Such inert surfaces, in particular the outer surface, may minimize chemical or biological interaction between the device itself and the in vivo environment. Inert materials suitable for the deformable reservoir are known in the art.

The deformable reservoir may include at least one inlet structure, mechanism or port for receiving material delivered from outside the environment to facilitate filling of the reservoir while remaining deployed in an animal. The inlet mechanism may be provided by a self-sealing material included in the body of the reservoir so that no hole is permanently made therein. The inlet mechanism may be configured to permit the entry of material into the deformable reservoir but prevent the material from exiting the deformable reservoir through the same mechanism. The inlet mechanism of the deformable reservoir may be a one-way valve or other mechanism that is capable of receiving a vehicle for delivering material to the reservoir, e.g., a syringe needle. Such inlet mechanism may be passive or active. An active inlet mechanism may be configured to accept external delivery of material on demand, and hence be controllable, and may be configured using the materials described herein for the controllable output mechanism. Such at least one controllable inlet mechanism may be activated using a control signal that is different from the at least one control signal used to activate and control the at least one controllable output mechanism. The inlet mechanism may also include means for decontaminating the vehicle that is delivering additional material. Such decontamination methods and mechanisms are known to those of skill in the art and can utilize transmission of UV light, and/or a chemical decontaminant.

As noted previously, delivery devices as described herein may include various types of micropumps or nanopumps suitable for injection. A micropump or nanopump suitable for use in a material delivery device may include a positive displacement micropump, a centrifugal pump, or a peristaltic pump. The choice of pump and method of construction thereof may depend upon the intended use of the material delivery device, the delivery site, the dimensions of the material delivery device, among other factors, as will be apparent to those of skill in the art. In some embodiments, the downstream location may be an environment in an animal. In some embodiments, the downstream location may be a downstream material handling structure, and in some embodiments, the downstream location may include a downstream environmental interface. An environmental interface may function to facilitate the distribution of a delivery material into an environment.

Figure 21:
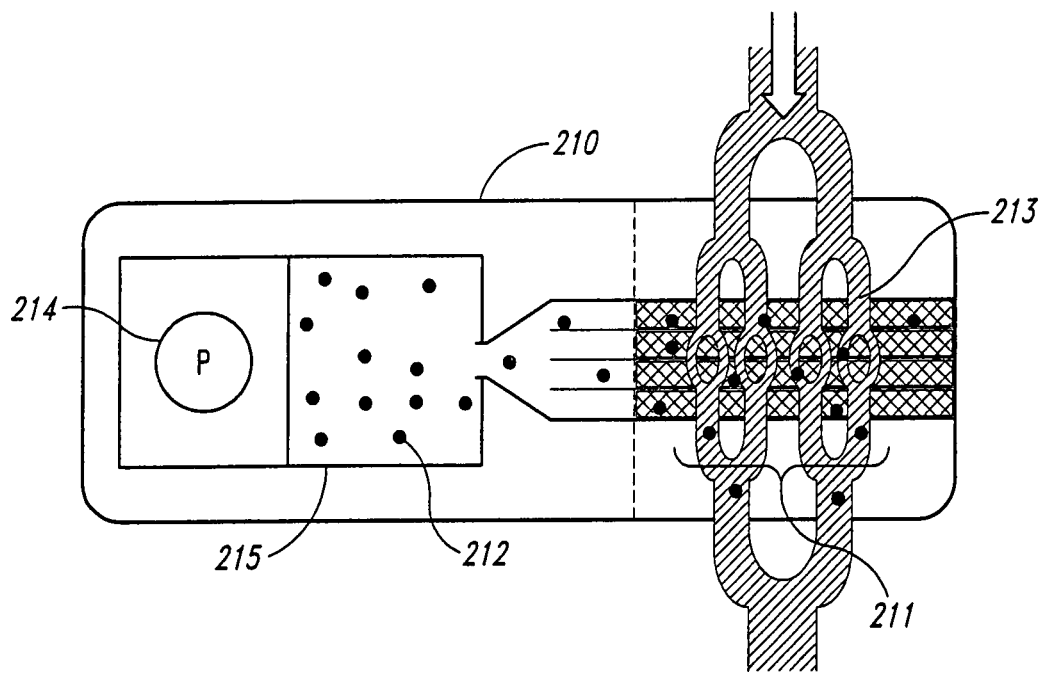
FIG. 21 illustrates an embodiment of a delivery device including an environmental interface.

FIG. 21 depicts an example of a material delivery device 210 including an environmental interface 211. In the embodiment of FIG. 21, the environmental interface 211 provides for the delivery of material 212 into blood flowing through capillaries 213. Material delivery device 210 includes pump 214 and a material-containing structure 215 (here depicted as a delivery reservoir) containing delivery material 212.

Figure 22:
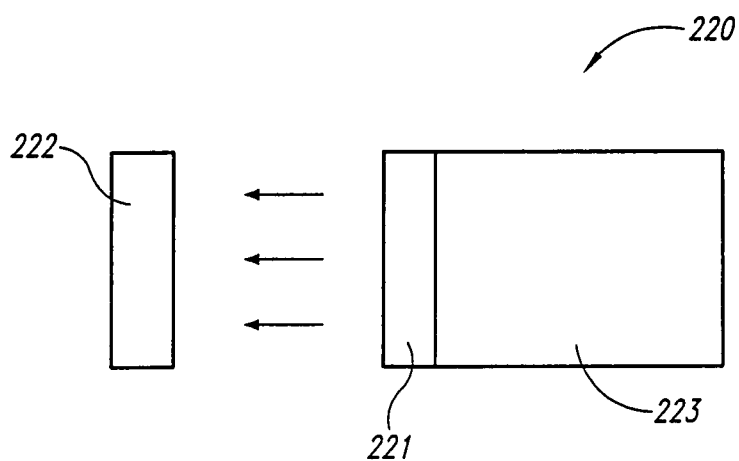
FIG. 22 illustrates a material delivery device including an extraction mechanism.

In other embodiments, a material delivery device 223 as schematically depicted in FIG. 22, may include an extraction mechanism 221 for removal of the entire device 220 from the in vivo environment. A removal tool may include a syringe including a hollow tube capable of receiving the material delivery device. As described above, a body structure may be deployed around the material delivery device, which body structure may facilitate the removal of a material delivery device. The material delivery device 223 may include an extraction mechanism 221 that facilitates the coupling of the material delivery device 223 to the extraction tool 222. The extraction mechanism 221 may include a magnetic portion on the material delivery device 223 that is attracted to and mates with a magnetic end of an extraction tool 222. In certain circumstances, removal of the material delivery device from the in vivo environment may be desired prior to the emptying of the at least one deformable reservoir. In such case, it may be necessary to remove all or a portion of the delivery material from the delivery reservoir prior to or in the course of the extraction of the device from the environment. Removal of the material from the reservoir can be accomplished by various methods and includes use of a syringe-like device or needle that can access the reservoir contents via the controllable inlet mechanism, or the controllable outlet mechanism.

A further embodiment includes a material delivery kit comprising at least one deployment mechanism; at least one deployable material delivery device deployable in an animal, the at least one deployable material delivery device being disposed in said deployment mechanism, including: at least one deformable reservoir configured to receive, retain and controllably release at least one material, including at least one outlet through which the at least one material may be released from the at least one, deformable reservoir; and at least one controllable output mechanism operably linked to said at least one outlet and configured to control the release of the at least one material from the at least one deformable reservoir. The deployment mechanism may include a syringe or a syringe-like device, or any other device known to one of skill in the art, that is configured to deploy the material delivery device into the in vivo environment. The material delivery kit may further include a remote controller configured to generate and transmit at least one control signal sufficient to activate the controllable output mechanism. The kit may further include, in an embodiment, at least one delivery material as described herein. The at least one delivery material may be sealed in a vial or be disposed within the deployment mechanism itself.

A further embodiment includes a method of delivering a material to an animal including deploying a material delivery device as described herein into an in vivo environment of an animal. The material delivery device including at least one deformable reservoir configured to receive and retain at least one delivery material, and including at least one outlet; at least one controllable output mechanism operably linked to the at least one outlet; and delivering a quantity of at least one material into the at least one deformable reservoir following deployment of the device into the in vivo environment; and transmitting an electromagnetic control signal to the in vivo environment containing the material delivery device, the electromagnetic control signal having signal characteristics receivable by the material delivery device and sufficient to activate the at least one controllable output mechanism to cause the exit of at least a portion of the at least one material from the at least one reservoir.

An embodiment may include a method of delivering a therapeutic agent to an animal including deploying a material delivery device into an in vivo environment of the animal; the material delivery device including at least one deformable reservoir configured to receive and hold delivery material, and including at least one outlet; at least one controllable output mechanism operably linked to the at least one outlet; delivering a quantity of at least one delivery material to the at least one deformable reservoir following deployment of the at least one reservoir in vivo; sealing the at least one deformable reservoir containing the at least one delivery material; and transmitting an electromagnetic control signal to the in vivo environment containing the material delivery device, the electromagnetic control signal having signal characteristics receivable by the material delivery device and sufficient to activate the at least one controllable output mechanism to cause the exit of a portion of the at least one material from the at least one deformable reservoir.

Figure 23:
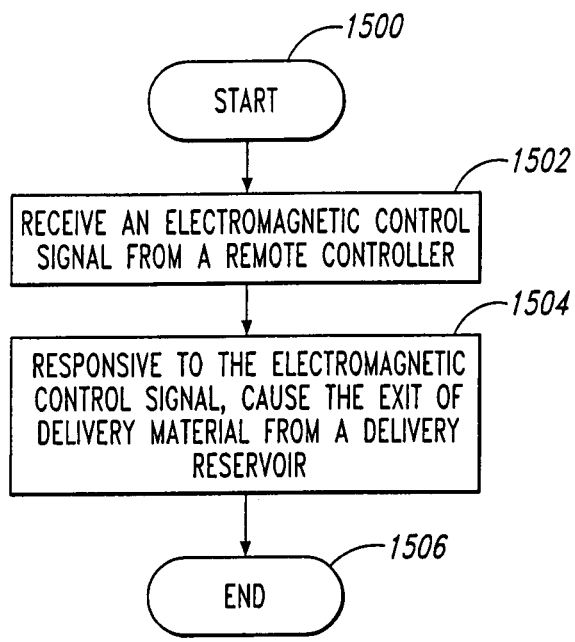
FIG. 23 is a flow diagram of a method of delivering a material.

FIG. 23 schematically depicts a method of delivery of a material through the use of a delivery device as described herein. The basic method 1500-1506 includes receiving a control signal from a remote controller at step 1502; and responsive to the electromagnetic control signal, causing the exit of delivery material from a delivery reservoir at step 1504.

Figure 24:
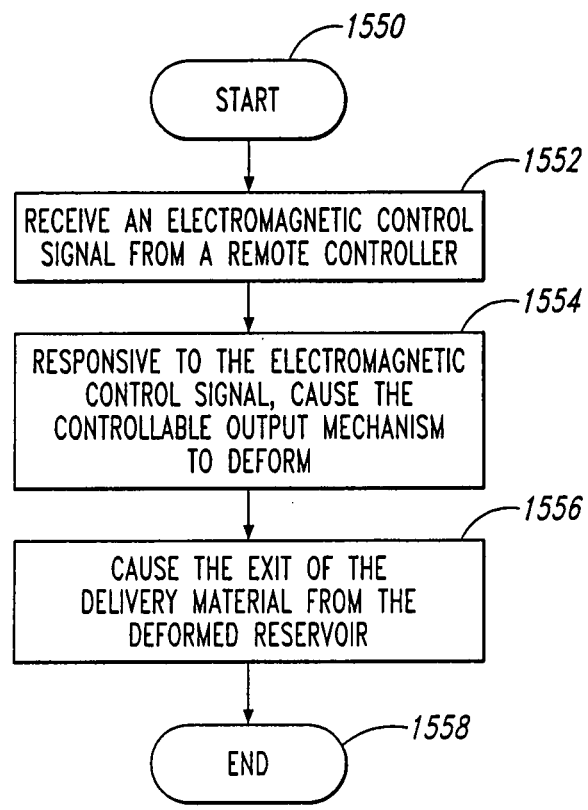
FIG. 24 is a flow diagram of a further method of delivering a fluid.

As schematically depicted in FIG. 24, an expanded version of the method 1550-1558 may include receiving an electromagnetic control signal from a remote controller at step 1552; and responsive to the electromagnetic control signal, causing the controllable output mechanism to deform (1554); and thereby cause the exit of material from a deformable delivery reservoir at step 1556.

A method as described herein may include receiving the control signal with a responsive (e.g., electromagnetically-responsive) material, which may include, for example, hydrogel, a permanently magnetizable material, a ferromagnetic material, a ferrimagnetic material, a ferrous material, a ferric material, a dielectric or ferroelectric or piezoelectric material, a diamagnetic material, a paramagnetic material, a metal, and an antiferromagnetic material. The method may include a step of dispensing the delivery material into an external environment, which may include, for example, the body of an animal, and in particular, the body of a human. Alternatively, the method may include dispensing the delivery material into a downstream environmental interface or a downstream material-handling structure, which may include a channel, a chamber, a mixer, a separator, or combination thereof.

Figure 25:
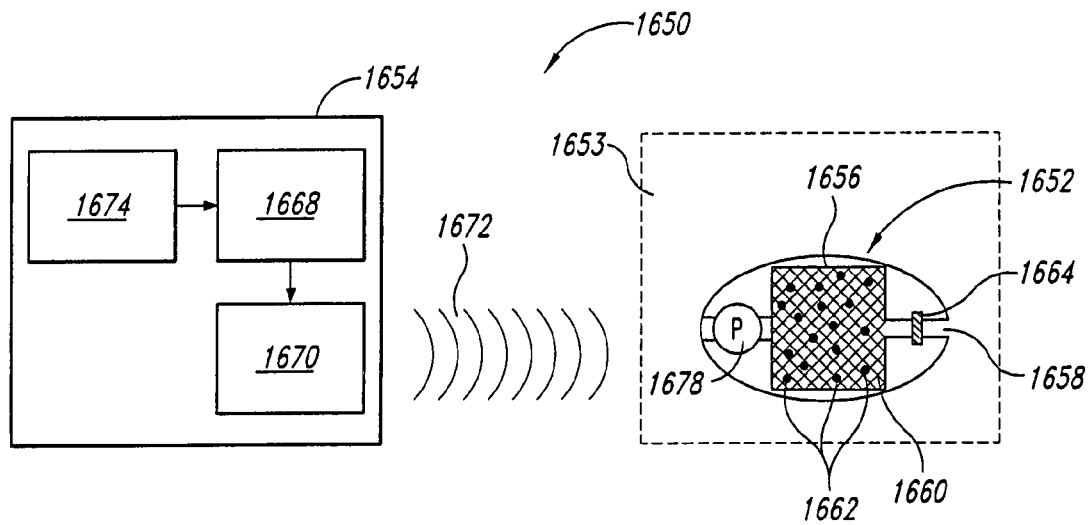
FIG. 25 is a schematic diagram of an embodiment of a system including a remote controller and a delivery device.

FIG. 25 depicts a schematic of a material delivery system 1650 that includes a material delivery device 1652 and a remote controller 1654. In this embodiment, material delivery device 1652 includes pump 1678, deformable reservoir 1656, containing delivery material 1662, having at least one outlet 1658 through which material may exit the deformable reservoir structure 1656; a delivery material in media 1660 contained within the deformable reservoir 1656; and at least one controllable output mechanism 1664 adapted or configured for controlling the exit of material from the reservoir in response to an incident electromagnetic control signal 1672 or in response to a sensed condition of a sensor. Remote controller 1654 includes an electromagnetic signal generator 1668 capable of producing an electromagnetic control signal 1672 sufficient to activate the controllable output mechanism 1664 of the material delivery device 1652 located in an environment 1653; and an electromagnetic signal transmitter 1670 capable of wirelessly transmitting the electromagnetic control signal 1672 to the controllable output mechanism 1664 of the delivery device in the environment to cause the delivery of the material to the environment. The remote controller may include electrical circuitry 1674, which may include at least one of hardware, firmware, or software configured to control generation of the electromagnetic control signal. The remote controller 1654 may include an electromagnetic signal generator 1668 configured to generate a static or quasi-static electrical field control signal, a static or quasi-static magnetic field control signal, a radio-frequency electromagnetic control signal sufficient, a microwave electromagnetic control, an infrared electromagnetic control signal, a millimeter wave electromagnetic control signal, an optical electromagnetic control signal (which may include ultraviolet and/or infrared wavelengths) sufficient to activate the controllable output mechanism to control the exit of the material from the material-containing structure. The remote controller may include an electromagnetic signal generator configured to generate a rotating electromagnetic control signal.

The at least one controllable output mechanism 1664 may include a magnetically or electrically active material including at least one hydrogel, permanently magnetizable material, ferromagnetic material, ferrimagnetic material, ferrous material, ferric material, dielectric material, ferroelectric material, piezoelectric material, diamagnetic material, paramagnetic material, metallic material, antiferromagnetic material or a combination of the foregoing materials. In some embodiments, the controllable output mechanism may include a polymer, ceramic, dielectric, metal, shape memory material, or a combination of a polymer and a magnetically or electrically active component.

Figure 26:
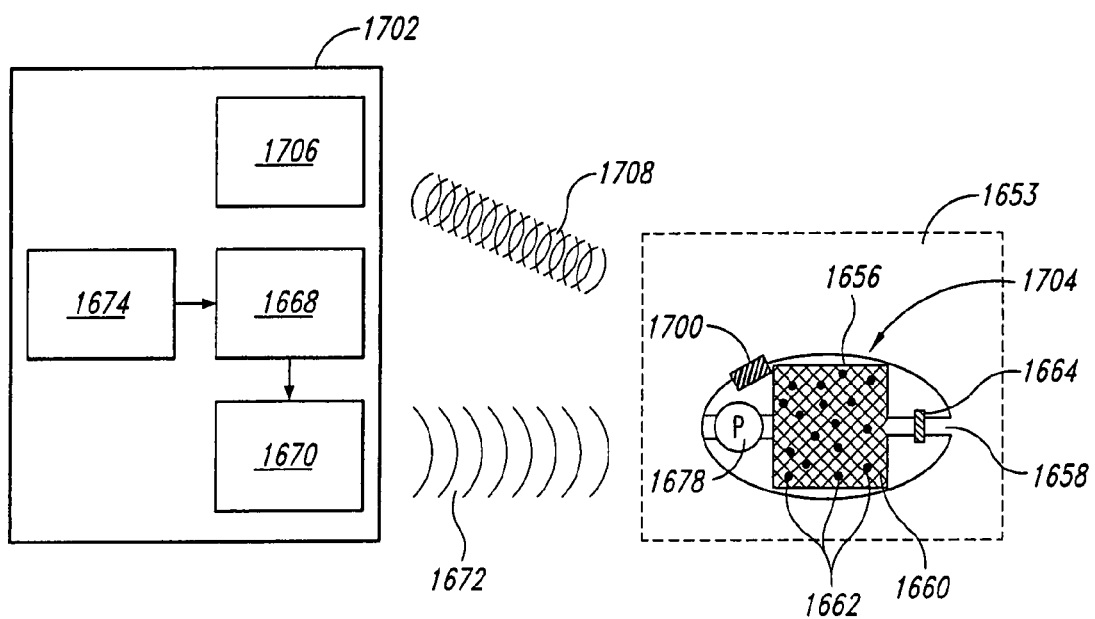
FIG. 26 is a diagram of an embodiment of a delivery system including a delivery device with an RFID.

In another embodiment schematically illustrated in FIG. 26 that is a variation of embodiment of FIG. 25, the material delivery device 1704 may also include RFID 1700. Remote controller 1702 may include RF interrogation signal generator 1706 for generating an RF interrogation signal 1708, which may be tuned to the RFID. Remote controller 1702 includes electromagnetic signal generator 1668, electromagnetic signal transmitter 1670, electrical circuitry 1674, which function generally as described in connection with FIG. 25. The remote controller may also include an interrogation signal transmitter for transmitting the transmittable RFID interrogation signal; an interrogation signal receiver for receiving a returned RFID interrogation signal from an RFID in a delivery device; and RFID detection circuitry configured to detect the presence of a selected RFID from a returned RFID interrogation signal. Upon detection of the presence of the selected RFID, to remote controller 1702 may generate and transmit a control signal configured for receipt by the delivery device including the selected RFID.

Figure 27:
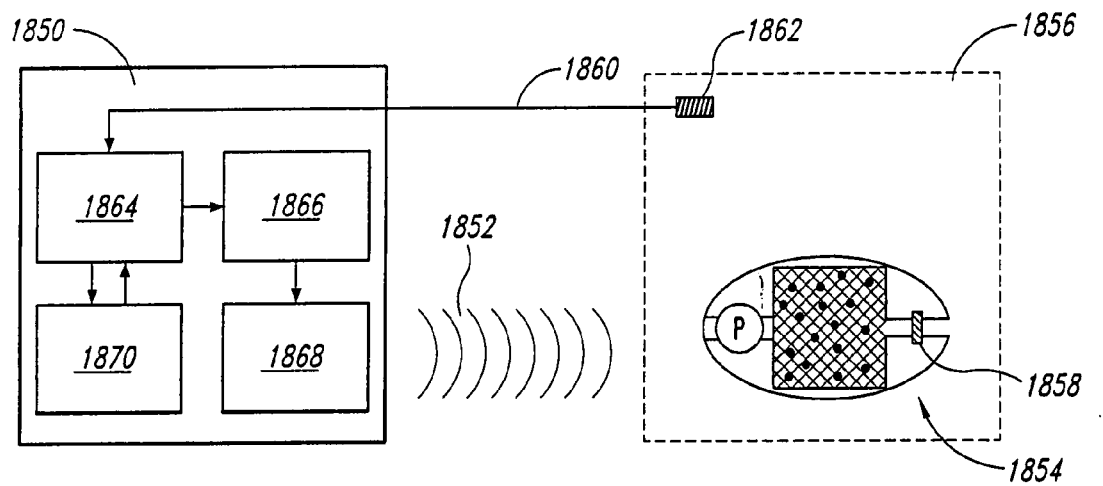
FIG. 27 is a schematic diagram of an embodiment of a system including a remote controller, a delivery device, and a sensor.

FIG. 27 schematically illustrates a delivery system including a remote controller 1850 that produces electromagnetic control signal 1852 that is transmitted to delivery device 1854 in an in vivo environment 1856. Electromagnetic control signal 1852 is received by, or indirectly activates, at least one controllable output mechanism 1858 in delivery device 1854. Remote controller 1850 may include a signal input 1851 adapted for receiving at least one signal 1860 sensed from an environment 1856 by at least one sensor 1862, wherein the electromagnetic signal 1852 is produced based at least in part upon the at least one signal 1860 sensed from the environment. For example, the signal 1860 may correspond to the presence or absence of a particular molecule or material, the temperature of the environment, or some other sensed condition or signal. Remote controller 1850 may include electrical circuitry 1864, signal generator 1866, signal transmitter 1868, and memory 1870. Signal, such as for example a feedback signal, from sensor 1862 may be transmitted wirelessly. Remote controller may include a signal input adapted for receiving a feedback signal corresponding to one or more parameters sensed from the environment, wherein the electromagnetic control signal is produced based at least in part upon the feedback signal sensed from the environment. For example, the feedback signal may correspond to the activity of the at least one controllable output mechanism, or the presence, concentration or chemical activity of a chemical or biological material in the environment.

Figure 28:
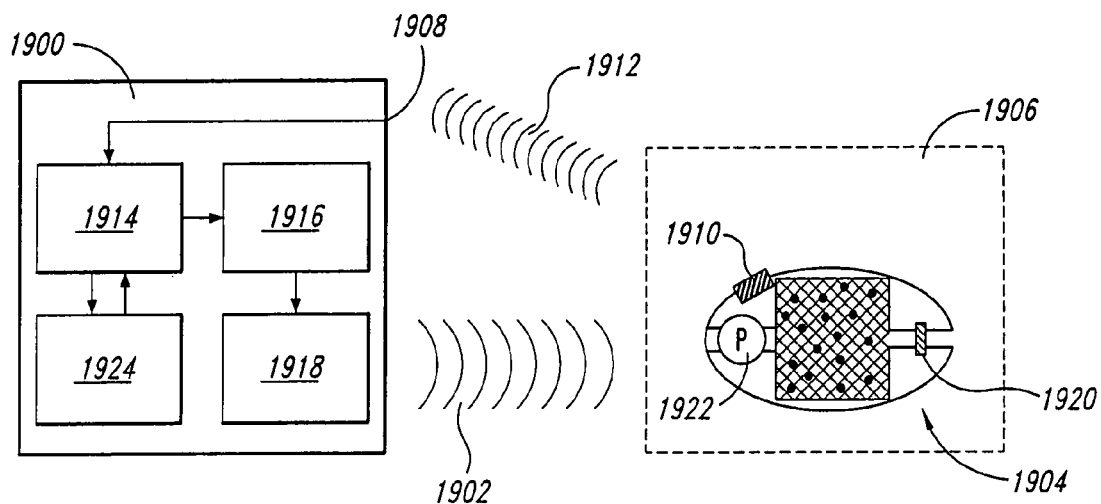
FIG. 28 is a schematic diagram of an embodiment of a system including a remote controller and a delivery device including a sensor.

FIG. 28 schematically illustrates another embodiment of a delivery system, including remote controller 1900, which transmits electromagnetic control signal 1902 to delivery device 1904 in environment 1906. Remote controller 1900 may include a signal input 1908 adapted for receiving a signal 1912 from at least one sensor 1910 in delivery device 1904. Electromagnetic control signal 1902 may be produced based at least in part upon the signal 1912 corresponding to one or more parameters sensed from the delivery device. In some embodiments, the signal from the delivery device may correspond to the presence or absence of a particular molecule or material, the concentration or chemical activity of a chemical within or around the delivery device, a temperature within or around the delivery device, the pumping or material-delivery rate of the delivery device, or some other parameter sensed from the delivery device. In others, the signal may correspond to the pumping rate of the delivery device, produced, for example, by pump 1922. In some embodiments, sensor 1910 may be configured for detecting at least one parameter from at least a portion of an environment surrounding the delivery device. The electromagnetic control signal 1902 may be determined based at least in part upon the signal 1912. Examples of sensors are described in U.S. Pat. No. 6,935,165, and U.S. Patent Publication 2004/0007051, and 2005/0208469, each of which are incorporated herein by reference. Further examples of sensors are described in "Easy-to-Make Nanosensors: Tiny electronics-based detectors could provide simple tests for cancer or bioterror agents." by Kevin Bullis, located at http://www.technologyreview.com/Nanotech/18127/which is incorporated herein by reference. Other examples of sensors are described by Gruner, G., "Carbon Nanotube Transistors for Biosensing Applications"; *Anal. Bioanal. Chem.* (2006) 384: 322-335, which is incorporated herein by reference. Carbon nanotube transistors are readily adapted for large scale manufacture as described by Gabriel, J C., *Mat. Res. Soc. Symp. Proc.*, (2003) Vol. 776, Q.12.7.1-12.7.7, which is incorporated herein by reference. Delivery device 1904 includes controllable output mechanism 1920. Signal 1912 may be transmitted wirelessly back to remote controller 1900. Remote controller 1900 may include processor 1914, signal generator 1916, signal transmitter 1918, and memory 1924.

Figure 29:
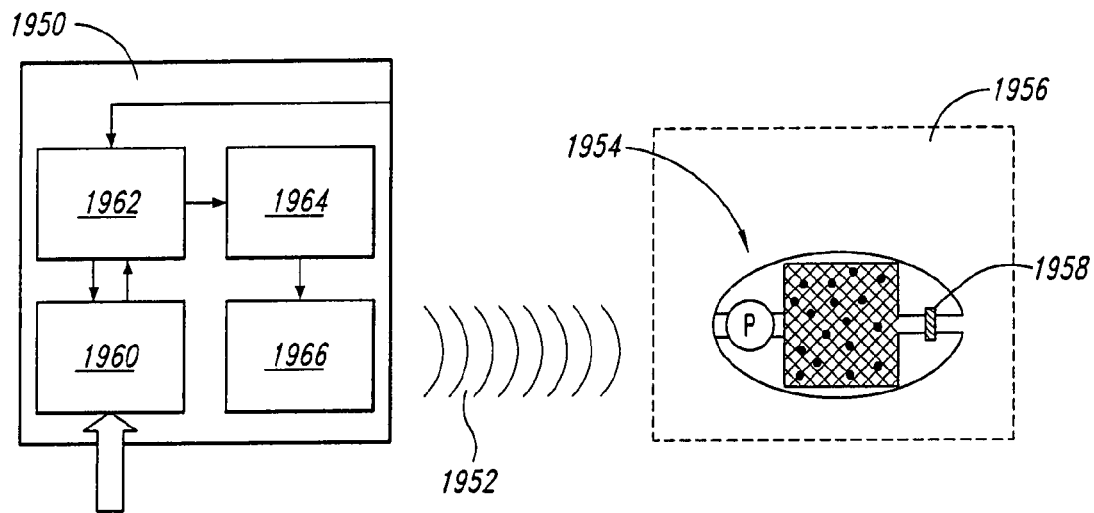
FIG. 29 is a schematic diagram of another embodiment of a system including a remote controller and a delivery device.

As schematically illustrated in FIG. 29, in some embodiments, the remote controller may be configured to receive user input of control parameters. Remote controller 1950 includes input 1960 for receiving input of information or instructions from a user such as, for example, commands, variables, durations, amplitudes, frequencies, waveforms, data storage or retrieval instructions, body data, etc. As in the other embodiments, remote controller 1950 transmits electromagnetic control signal 1952 to material delivery device 1954 in environment 1956, where it activates controllable output mechanism 1958. Input 1960 may include one or more input devices such as a keyboard, keypad, microphone, mouse, etc. for direct input of information from a user, or input 1960 may be any of various types of analog or digital data inputs or ports, including data read devices such as disk drives, memory device readers, and so forth in order to receive information or data in digital or electronic form. Data or instructions entered via input 1960 may be used by electrical circuitry 1962 to modify the operation of remote controller 1950 to modulate generation of an electromagnetic control signal 1952 by signal generator 1964 and transmission of the electromagnetic control signal 1952 by transmitter 1966. In some embodiments, the remote controller may be configured with a memory mechanism or memory location to record a user's input regarding the user's physical state. For example, the user may input the time and date and nature of his/her condition. For example, the remote controller may be configured to receive inputs alphanumeric inputs such as whether the user feels well or poorly, has a headache or fever, is suffering loss of sleep or appetite, is dizzy, nauseated, irritable, etc. Such recorded information may be useful to a treating physician and for example, may allow the physician to compare the user inputs with the recorded information from the delivery device with respect to time and quantity of material delivery to adjust the programmed schedule and/or quantity of material delivery. In some embodiments, the remote controller may be configured with a learning functionality that is responsive to the user inputs. The remote controller may be programmed to respond to certain predetermined user inputs in any number of ways designated by a physician, for example, with a programmed adjustment of material dosage and schedule.

Figure 30:
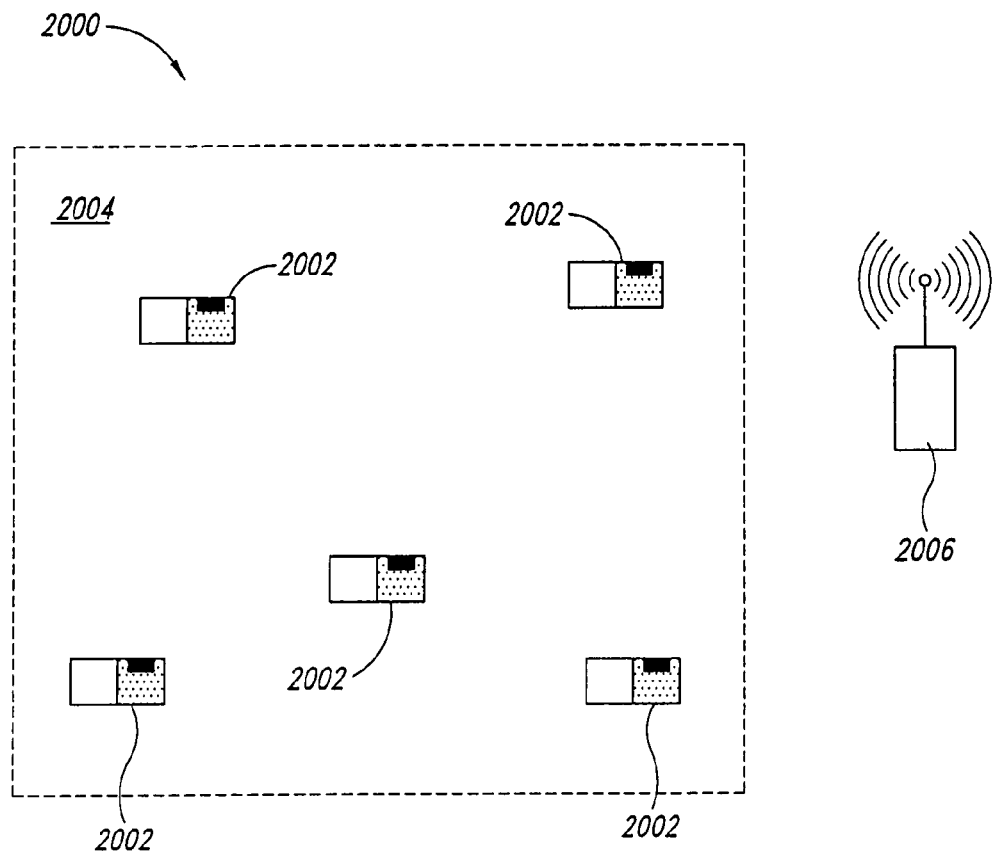
FIG. 30 is an embodiment of a system including a remote controller and a plurality of delivery devices in an environment.

FIG. 30 schematically illustrates a delivery system that includes a plurality of delivery devices, where two or more of the plurality of delivery devices are controlled by the remote controller. A delivery device may include a plurality of selectively activatable output mechanisms, each associated with a material handling element, which may thus be controlled to perform multiple material-handling steps in a particular sequence. It is also contemplated that a delivery system may include a plurality of delivery devices which may be of the same or different types. As shown in FIG. 30, a delivery system 2000 may include a plurality of identical delivery devices 2002 distributed throughout an in vivo environment 2004 in order to perform or control material delivery at a plurality of locations within the environment, and controlled by a remote controller 2006. Alternatively, a delivery system may include a plurality of different delivery devices at different locations within an environment, each performing or controlling material delivery suited for the particular location. The embodiments described herein are not limited to devices or systems or methods including any specific number or configuration of controllable output mechanisms within a delivery device, or specific number or configuration of delivery devices or remote controllers within a delivery system. Depending upon the particular application of a system, controllable output mechanisms and/or delivery devices may be controlled in a particular pattern to producing a desired distribution of a delivery material in an animal. Control of such systems may be performed with the use of suitable hardware, firmware, software, or through one or a plurality of remote controllers.

The remote controller used in the system depicted in FIG. 30 may include an electromagnetic signal generator capable of producing an electromagnetic control signal sufficient to activate at least one controllable output mechanisms in a plurality of delivery devices located in an animal to control the rate of ejection of delivery material from within at least one deformable reservoir of each of the devices. In a related embodiment, the remote controller may include a plurality of signal inputs adapted for receiving signals from the plurality of delivery devices, the plurality of signal inputs coupled to a microprocessor configured to generate the electromagnetic control signal based upon the plurality of signals.

Selective activation or control of controllable output mechanisms may be achieved by configuring controllable output mechanisms to be activated by control signals having particular signal characteristics, which may include, for example with regard to an electromagnetic control signal, particular frequency, phase, amplitude, temporal profile, polarization, and/or directional characteristics, and spatial variations thereof. For example, different controllable output mechanisms may be responsive to different frequency components of a control signal, thereby allowing selective activation of the different controllable output mechanisms. The remote controller or a microprocessor mechanism included in the material delivery device may be configured to produce a rotating electromagnetic signal, the rotating electromagnetic signal capable of activating the two or more delivery devices independently as a function of the orientation of the rotating electromagnetic signal.

Figure 31:
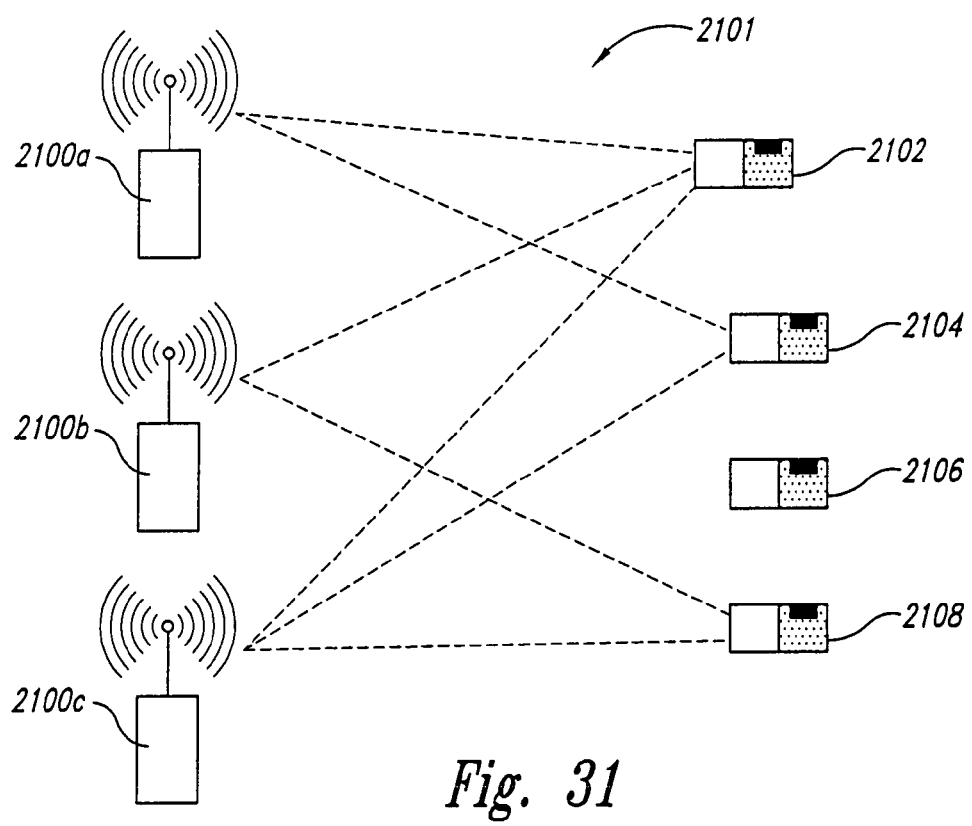
FIG. 31 is a schematic of an embodiment of a delivery system.

As schematically depicted in FIG. 31, in some embodiments, a delivery system 2101 or may include a plurality of delivery devices 2102, 2104, 2106, and 2108, and a plurality of remote controllers 2100a, 2100b, 2100c. As shown in FIG. 31, each delivery device may be controlled by one or more control signals produced in a distributed fashion by two or more of the plurality of remote controllers 2100a-2100c.

Figure 32:
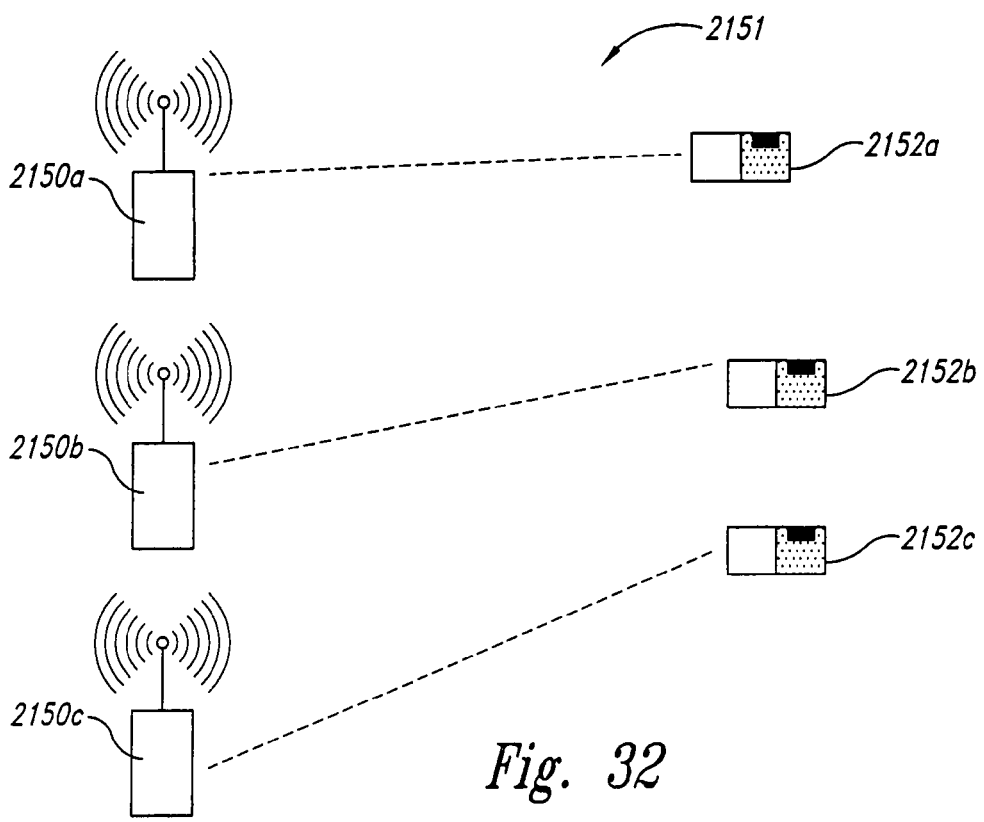
FIG. 32 is a schematic of a further embodiment of a delivery system.

As schematically depicted in FIG. 32, in some embodiments a delivery system 2151 may include a plurality of delivery devices 2152a, 2152b, and 2152c and a plurality of remote controllers 2150a, 2150b, and 2150c, each delivery device may be controlled by a separate remote controller, for example delivery device 2152a controlled by remote controller 2150a, delivery device 2152b controlled by remote controller 2150b, and delivery device 2152c controlled by remote controller 2150c.

Figure 33:
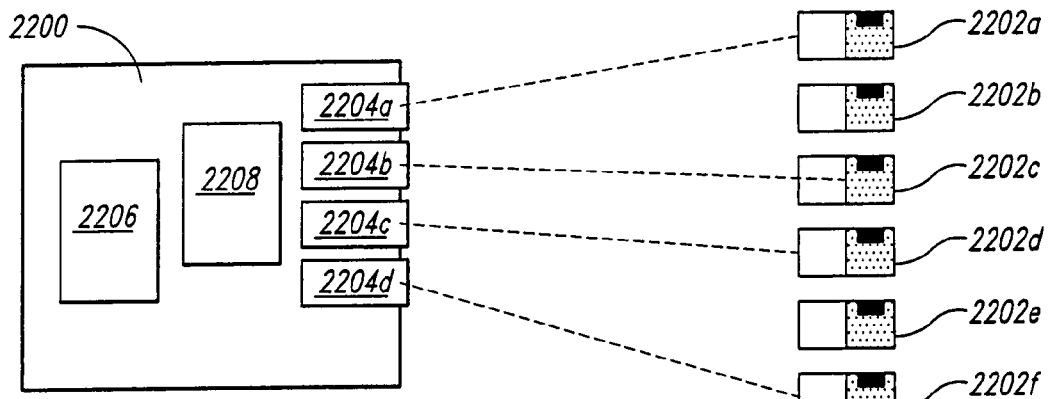
FIG. 33 is a schematic of a further embodiment of a delivery system.

In other embodiments, as schematically depicted in FIG. 33, a remote controller 2200 may include a plurality of transmission channels 2204a, 2204b, 2204c, and 2204d, for example (more or fewer channels may be used, without limitation). Remote controller 2200 may also include channel allocation hardware or software 2206 configured to allocate usage of the plurality of transmission channels 2204a-2204d for the transmission of the electromagnetic control signal from signal transmitter 2208 to selected delivery devices of the plurality of delivery devices 2202a-2202f.

Figure 34:
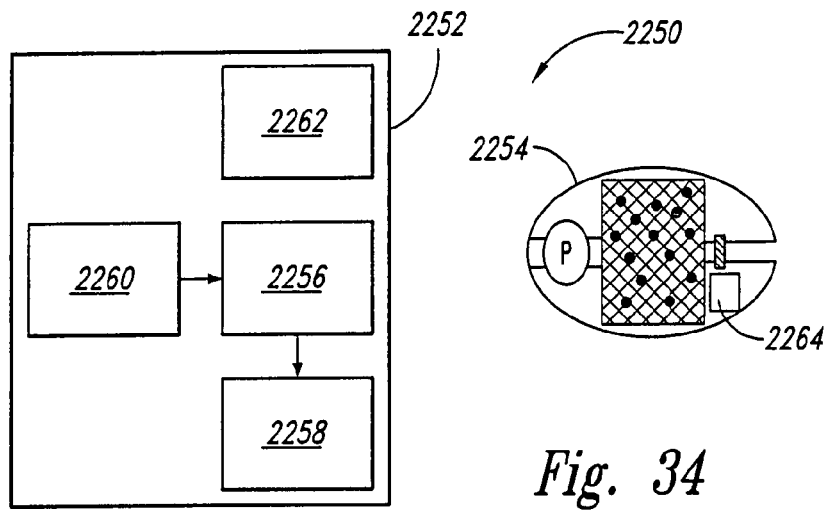
FIG. 34 depicts an embodiment of a delivery system including encryption.

In another embodiment of a delivery system 2250 schematically illustrated in FIG. 34, the remote controller 2252 may include encryption hardware or software 2262 configured to encrypt one or more control signal components, wherein the encrypted one or more control signal components are receivable by a delivery device 2254 including a corresponding decryption component 2264 which may include hardware, firmware or software configured for performing a decryption protocol coordination with remote controller 2252. Remote controller 2252 may include signal generator 2256, signal transmitter 2258, and electrical circuitry 2260, as described generally elsewhere.

Figure 35:
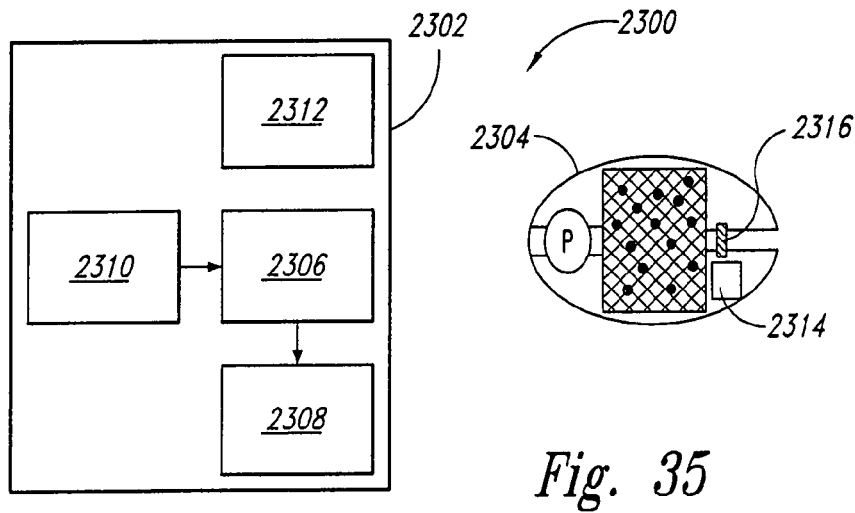
FIG. 35 depicts an embodiment of a delivery system that utilizes an authentication procedure.

In another embodiment of a delivery system 2300 schematically illustrated in FIG. 35, the remote controller 2302 may include authentication hardware or software 2312 configured to perform an authentication procedure with a delivery device 2304, wherein the remote controller 2302 is configured to produce activation of the controllable output mechanism 2316 of an authenticated delivery device but not the controllable output mechanism of a non-authenticated delivery device. Again, remote controller 2302 may include signal generator 2306, signal transmitter 2308, and electrical circuitry 2310, as described generally elsewhere, and authentication component 2314, which may include hardware, firmware or software configured for performing an authentication protocol with remote controller 2302.

In various embodiments of the remote controller described herein, the generated electromagnetic control signal may have a defined magnetic field strength, or alternatively, or in addition, a defined electric field strength. Depending upon the intended application, the electromagnetic control signal may have signal characteristics sufficient to produce a change in dimension of the controllable output mechanism, a change in temperature of at least a portion of the controllable output mechanism, a change in conformation or configuration of the controllable output mechanism, or a change in orientation or position of the controllable output mechanism. The remote controller may include an electromagnetic signal generator that includes an electromagnetically- or electrically- or magnetically-polarizable element, or one or more permanent magnets or electric.

Figure 36:
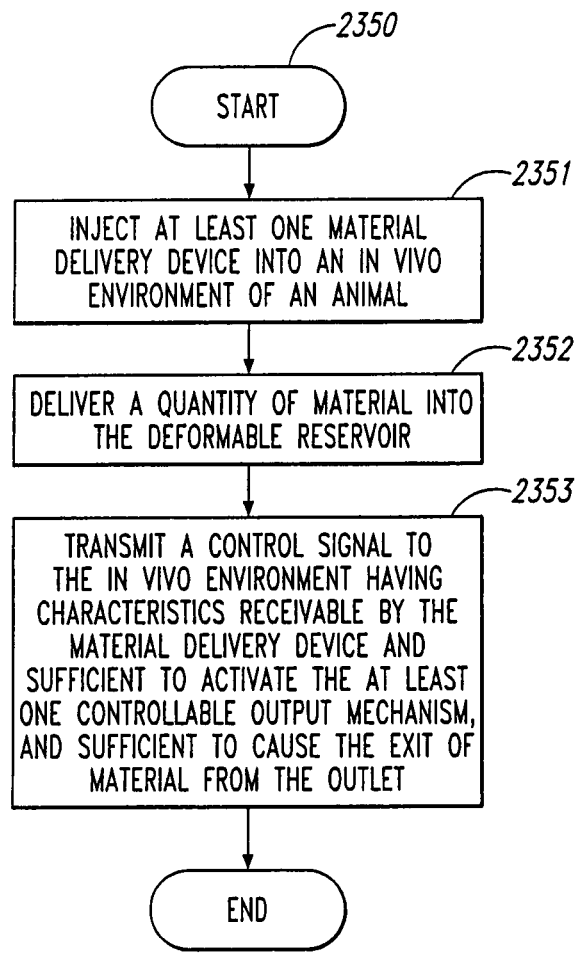
FIG. 36 is a flow diagram of a method of delivering a material.

FIG. 36 schematically depicts the steps of a method 2350 of delivering a material to an animal, comprising deploying at least one material delivery device into an in vivo environment of an animal (2351), the material delivery device including at least one controllable output mechanism and at least one deformable reservoir capable of receiving and holding delivery material, and including at least one outlet, delivering a quantity of at least one material into the deformable reservoir (2352); and transmitting a control signal to the in vivo environment containing the material delivery device, the control signal having signal characteristics receivable by the material delivery device sufficient to activate the at least one controllable output mechanism and sufficient to cause the exit of a portion of the at least one material from the at least one outlet (2353), at step 2352. The methods described herein including a control signal may be accomplished using a remote controller to generate and transmit the control signal or by using a microprocessor (also described herein as a processor) and a memory that are included in the material delivery device itself.

Figure 37:
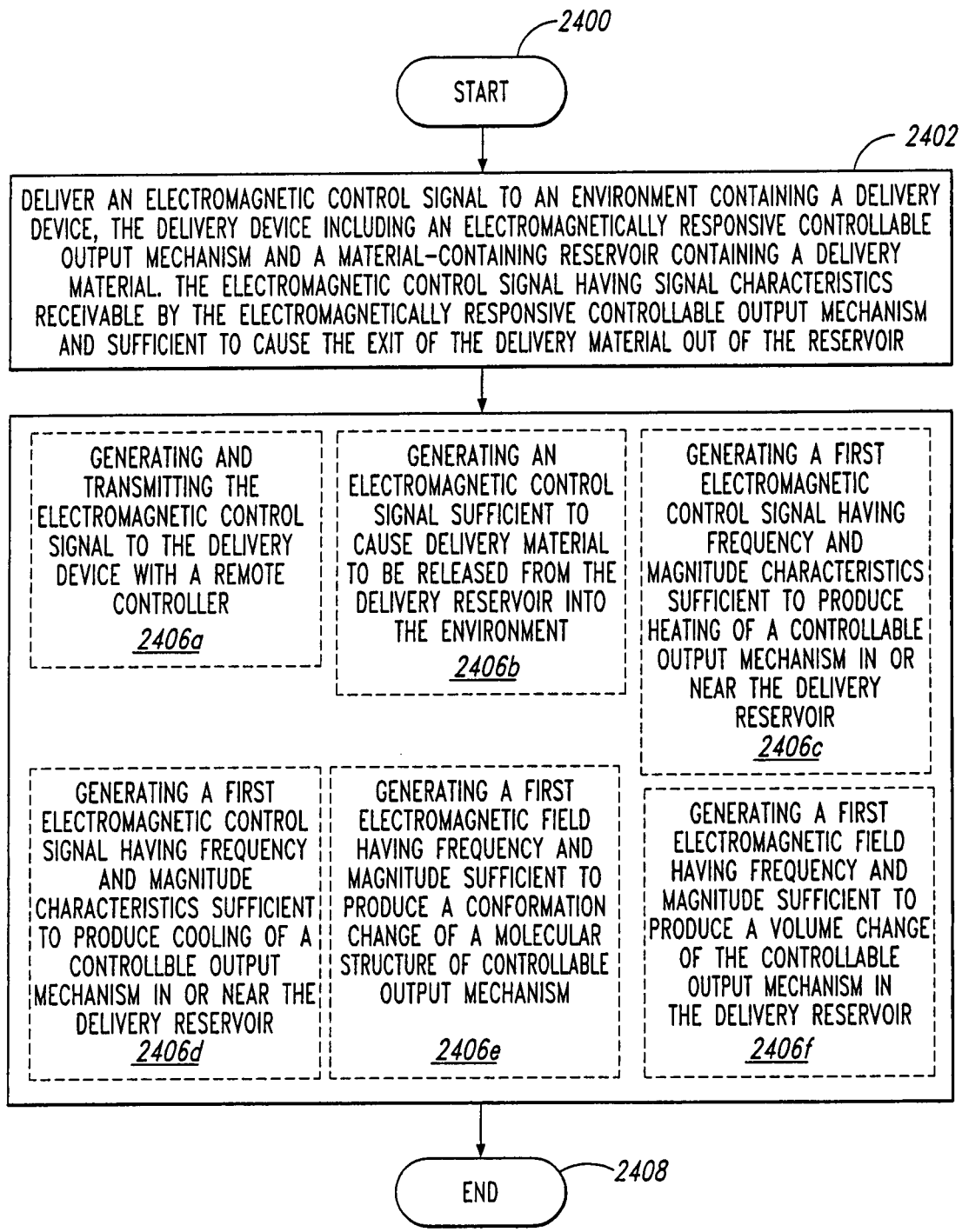
FIG. 37 is a flow diagram of a method of delivering a material.

FIG. 37 schematically depicts further variations of the method of FIG. 36. For example, the method 2400 may include delivering an electromagnetic control signal to an environment containing a delivery device, the delivery device including an electromagnetically responsive controllable output mechanism and a material-containing reservoir containing a delivery material, and the electromagnetic control signal having signal characteristics receivable by the electromagnetically responsive controllable output mechanism and sufficient to cause the exit of a portion of the delivery material out of the reservoir. Further steps may include generating and transmitting an electromagnetic control signal to the delivery device with a remote controller, as shown at 2406a. Alternatively, the method may include generating a first electromagnetic control signal sufficient to cause a portion of the at least one delivery material to exit from the deformable reservoir into the in vivo environment, as shown at 2406b. Or, the method may include generating a first electromagnetic control signal having frequency and magnitude sufficient to produce heating of at least one controllable output mechanisms, as shown at 2406c. Alternatively, the method may include generating a first electromagnetic control signal having frequency and magnitude sufficient to produce cooling of at least one controllable output mechanisms, as shown at 2406d, generating a first electromagnetic field having frequency and magnitude sufficient to produce a conformation change of a molecular structure, as shown at 2406e, or generating a first electromagnetic field having frequency and magnitude sufficient to produce a volume change of a material a molecular structure, as shown at 2406f.

Figure 38:
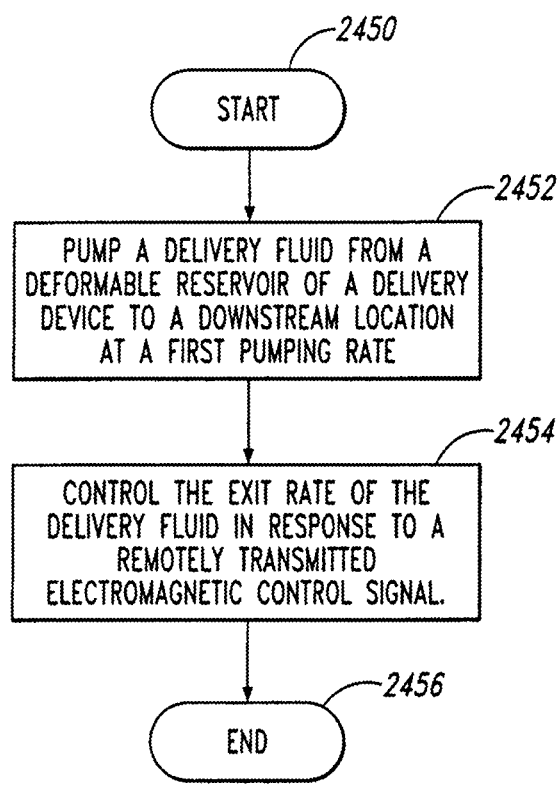
FIG. 38 is a flow diagram of a portion of a method of delivering a material.

FIG. 38 schematically depicts a method 2450-2456 of delivering a material (which in this Figure is depicted as a fluid, by way of example) including pumping a delivery fluid from a reservoir of a delivery device to a downstream location at a first pumping rate at step 2452; and controlling the rate of exit of the material in response to a remotely transmitted electromagnetic control signal at step 2454. In some embodiments, the first pumping rate may be a constant pumping rate. In some embodiments, the method may include varying the rate of delivery of the material to the downstream location in response to the remotely transmitted electromagnetic control signal. In other embodiments, the first pumping rate may be a time-varying pumping rate. The first pumping rate is modifiable in response to a remotely transmitted electromagnetic control signal, for example. The method may include controlling the exit of the fluid through activation of a controllable output mechanism in the delivery device by the remotely transmitted electromagnetic control signal to activate the controllable output mechanism, for example by heating of the controllable output mechanism, or cooling of the controllable output mechanism. In some variants of the method, activation of the controllable output mechanism may include a change in at least one dimension of the controllable output mechanism, a change in orientation of the controllable output mechanism, or a change in conformation of the controllable output mechanism.

Figure 39:
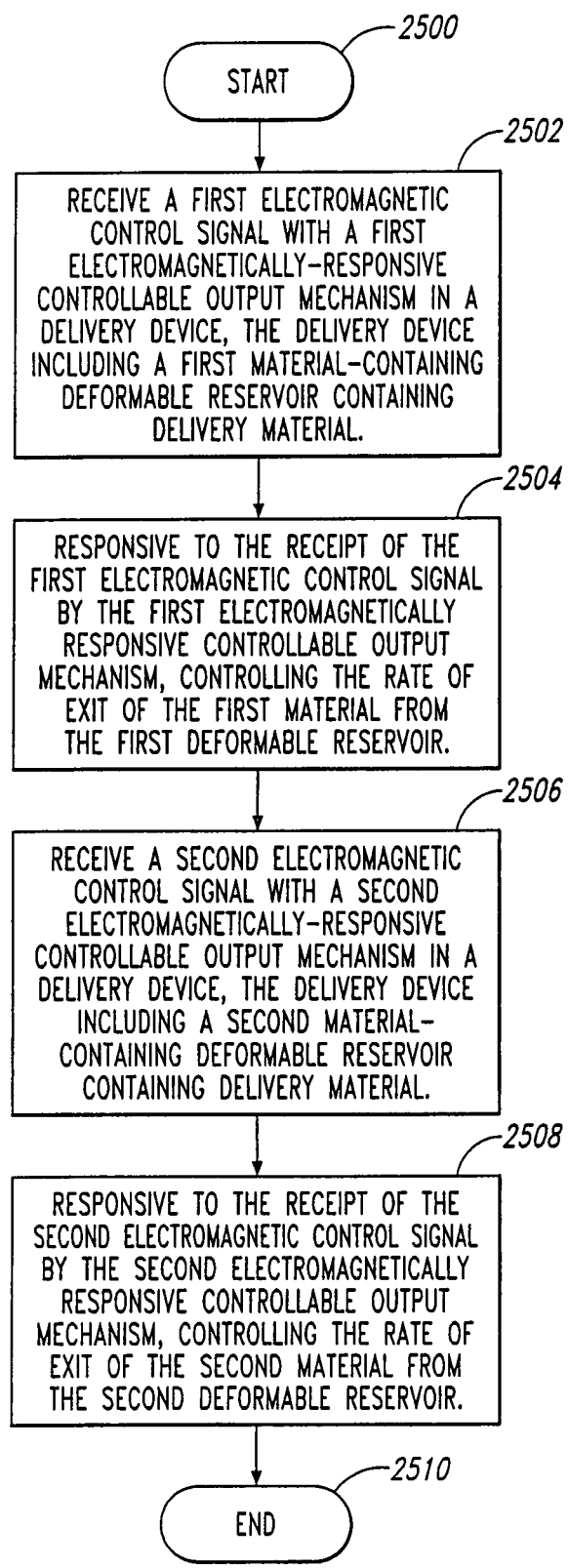
FIG. 39 is a flow diagram of another method of delivering a material.

In the method 2500-2510 of FIG. 39, in some embodiments where the material delivery device includes at least two deformable reservoirs each including at least one outlet and at least one controllable output mechanism, the at least two deformable reservoirs may contain the same or different materials. The method (2502, 2504) may include controlling the rate of exit of a first delivery material to an optional downstream location in response to receipt of a first control signal (in this Figure, a first control signal is electromagnetic, by way of example) by a first controllable output mechanism (2506, 2508), and controlling the rate of exit of a second, or additional, delivery material to an optional downstream location in response to receipt of a second, or additional, control signal (in this Figure, a second control signal is electromagnetic, by way of example) by a second, or additional, controllable output mechanism. In some embodiments, the at least two electromagnetic control signals may be the same electromagnetic control signal. In other embodiments, the at least two electromagnetic control signals may be different. In some embodiments, the at least two electromagnetic control signals may include control signals that are the same and other(s) that are different. In some embodiments, the at least two controllable output mechanisms may be all the same controllable output mechanism, while in other embodiments, the at least two controllable output mechanisms may be each different controllable output mechanisms or some of the at least two controllable output mechanism are the same while some are different. "Different" controllable output mechanisms may be controllable output mechanisms of different types, or distinct controllable output mechanisms that are of the same type. In other embodiments, the at least two delivery materials may be different or the same. In still other embodiments, the at least two delivery materials may form a therapeutic "cocktail" for preventing or treating a certain disease or condition. The at least two delivery materials may be delivered under regimens that are sequential, concomitant or on different schedules. The at least two delivery materials may be reactants that react in vivo or in a chamber prior to being dispensed in vivo.

Figure 40:
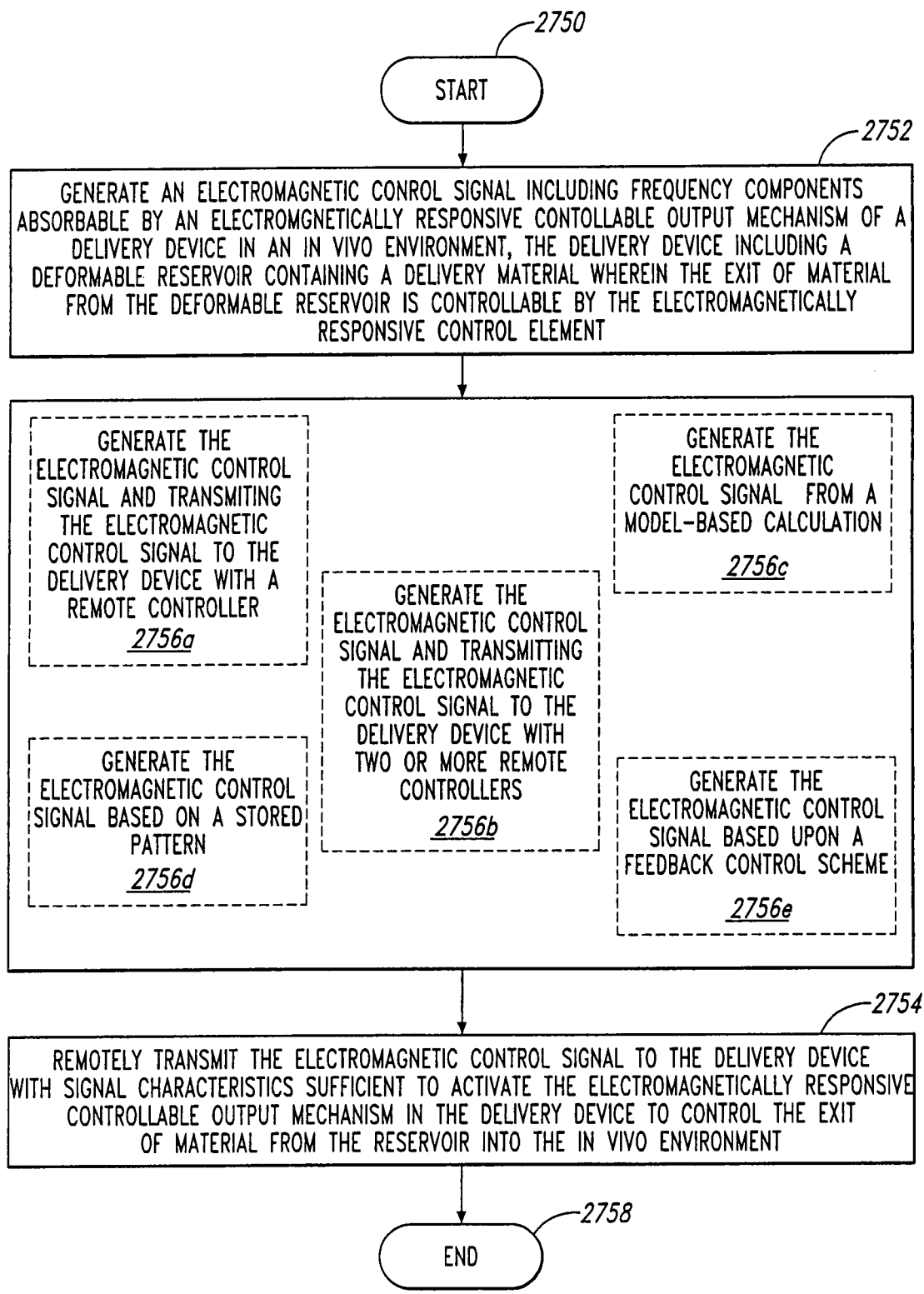
FIG. 40 is a flow diagram of another method of delivering a material.

FIG. 40 schematically illustrates a method 2750-2758 with a number of alternative steps relating to generation of the electromagnetic control signal 2752. Step 2756a includes generating the electromagnetic control signal and transmitting the electromagnetic control signal to the delivery device with a remote controller. Step 2756b includes generating the electromagnetic control signal and transmitting the electromagnetic control signal to the delivery device with two or more remote controllers. Step 2756c includes generating the electromagnetic control signal from a model-based calculation. Step 2756d includes generating the electromagnetic control signal based on a stored pattern. As another alternative, step 2756e includes generating the electromagnetic control signal based upon a feedback control scheme. A feedback control scheme may be, for example, a variable feedback control scheme. Step 2754 includes remotely transmitting the electromagnetic control signal to the delivery device with signal characteristics sufficient to activate the electromagnetically responsive controllable output mechanism in the delivery device to control the exit of a portion of material from the reservoir into the in vivo environment.

Figure 41:
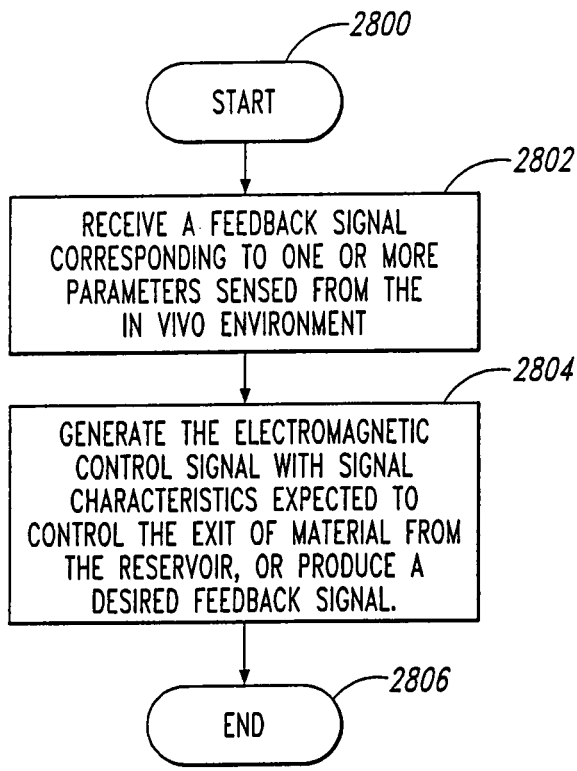
FIG. 41 is an expansion of the method of FIG. 40.
Figure 42:
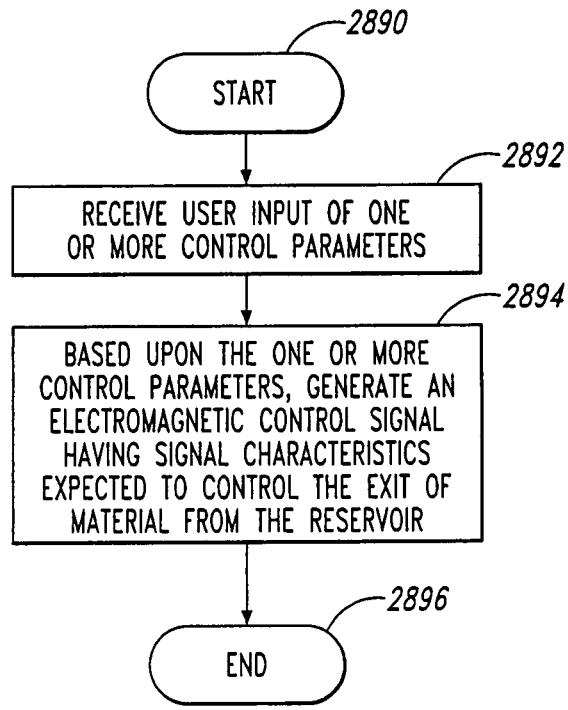
FIG. 42 is a flow diagram of additional steps for controlling a delivery device.

A further expansion the method shown in FIG. 40 may include the additional steps schematically depicted in FIG. 41 (steps 2800-2806), namely receiving a signal corresponding to one or more parameters sensed from the in vivo environment at 2802; and based upon the signal, generating the electromagnetic control signal with signal characteristics expected to produce a desired signal, at 2804. In some embodiments, receiving the signal from the in vivo environment may include receiving signals from at least one sensor in the environment, while in other embodiments it may include receiving the signal from the environment including receiving signals from two or more sensors in the environment. Receiving the signal from the environment may include, for example, receiving a measure of the temperature, or concentration or presence or absence of a chemical or biological material within at least a portion of the environment.

In another variation of the method shown herein may include the additional steps of receiving a feedback signal from the delivery device; and based upon the feedback signal, generating an electromagnetic control signal having signal characteristics that are expected to control the exit of a portion of material from the reservoir, or to produce a desired signal. Receiving a signal from the material delivery device may include receiving signals from at least one sensor in the material delivery device, or alternatively, receiving a signal from the delivery device may include receiving signals from two or more sensors in the delivery device. For example, receiving the signal from the delivery device may include receiving a signal representing the activity of the controllable output mechanism, the temperature, quantity, quality or degradation status, or concentration of a delivery material within or around the delivery device. In other embodiments, receiving the signal from the delivery device may include receiving a signal representing whether the deformable reservoir needs to be refilled.

Another variation of the method depicted herein, schematically shown in FIG. 42 (steps 2890-2896), may include the additional steps of receiving user input of one or more control parameters at 2892; and based upon the one or more control parameters, generating an electromagnetic control signal having signal characteristics expected to cause the exit of a portion of the material from the reservoir, as 2894.

Further additions to the method include steps of activating the controllable output mechanism to produce heating or cooling, or activating the controllable output mechanism to produce a change in configuration of the controllable output mechanism. Steps of generating an electromagnetic control signal and remotely transmitting the electromagnetic control signal to the delivery device may be performed according to instructions provided in the form of software, hardware or firmware. In some method embodiments, the steps of generating an electromagnetic control signal and remotely transmitting the electromagnetic control signal to the delivery device may be performed according to instructions distributed among a plurality of controllers or transmitters.

Further embodiments for controlling the controllable output mechanism include the addition of a on/off mechanically-actuated switch. The switch may be actuated by any means and may include, but not be limited to a pressure-sensing switch, that may be actuated by the user. The user may desire to turn on or off the material delivery device as needed.

Generating the electromagnetic control signal includes generating a static or quasi-static magnetic field, static or quasi-static electrical field, radio-frequency electromagnetic signal, microwave electromagnetic signal, millimeter wave electromagnetic signal, optical electromagnetic signal, an infrared electromagnetic signal, or an ultraviolet electromagnetic signal. Generating the electromagnetic control signal may be performed under hardware, firmware or software control, or via action of a circuit FIG. 43A schematically illustrates an embodiment relating to a kit as described herein. The kit comprises a deployment mechanism, which in FIG. 43A is a syringe-like device 430 containing a material delivery device with a deformable reservoir 431 as described herein, and may include a material for delivery to an in vivo environment of an animal. The syringe or deployment mechanism may comprise a barrel having a proximal end 434 and a distal end 435, a cannula 436 in communication with the distal end, and a plunger 437 disposed through the proximal end and slideable in relation to the barrel. The syringe or plunger may include at least one cavity 438 (in the Figure, the plunger is depicted by way of example) for retaining at least one material for delivery to the at least one deformable reservoir 431. According to an embodiment, a material delivery device may be disposed in the cannula 436 including at least one deformable reservoir 431 configured to receive and hold a material following injection into an animal, the deformable reservoir including at least one outlet through which material may exit the at least one deformable reservoir; at least one controllable output mechanism 440 operably linked to said at least one outlet and capable of being activated to control the exit of material from the at least one deformable reservoir. The kit may also include a remote controller 441 capable of generating a control signal 442 sufficient to activate the at least one controllable output mechanism 440. Alternatively, the remote controller may be configured to generate instructions that program the processor (e.g., hardware, firmware or software) of the material delivery device, thereby programming the function of the device. The at least one cavity 438 of the plunger may also be pre-filled with the at least one delivery material or may be configured for receiving the at least one delivery material at the time of use.

The in vivo deployment of the material delivery device as described herein can be accomplished by various ways and means, including a deployment mechanism. Referring to FIG. 43B, an embodiment provides for the insertion of material delivery device including deformable reservoir 431 within the cannula 436 (e.g., a hypodermic needle) of the syringe, and the delivery material 432 within a cavity of the barrel or within a cavity 438 of the plunger 437. To deploy the material delivery device including controllable output mechanism 440, the cannula 436 is inserted into the in vivo environment 450, such as transcutaneously into the peritoneal cavity. The plunger 437 is slideably moved through the barrel of the syringe where it pushes the material delivery device to exit the cannula 436 into the in vivo environment 450. Following placement of at least a portion of the deformable reservoir 431 in the in vivo environment 450, the material 432 may be delivered from the syringe to the inner cavity of the deployed deformable reservoir 431 where it resides in the reservoir. The reservoir deforms in vivo to accept the delivery material and following delivery of a predetermined quantity of material inside the deformable reservoir, the deformable reservoir is sealed to maintain its delivery material contents. The delivery device is separated from the cannula 436 and the cannula 436 may then be withdrawn from the in vivo environment 450. The method and devices described herein also may be accomplished using an automated device. For example, to provide consistent application of pressure to deploy the material delivery device and the delivery material, a device may be employed that uses a mechanical mechanism to drive a plunger or other piston-like element that forces the delivery device into the in vivo environment followed by the delivery of the material into the deformable reservoir. Automated mechanical mechanisms may avoid the possibility of deploying the device or material too swiftly or too slowly.

Figure 44A:
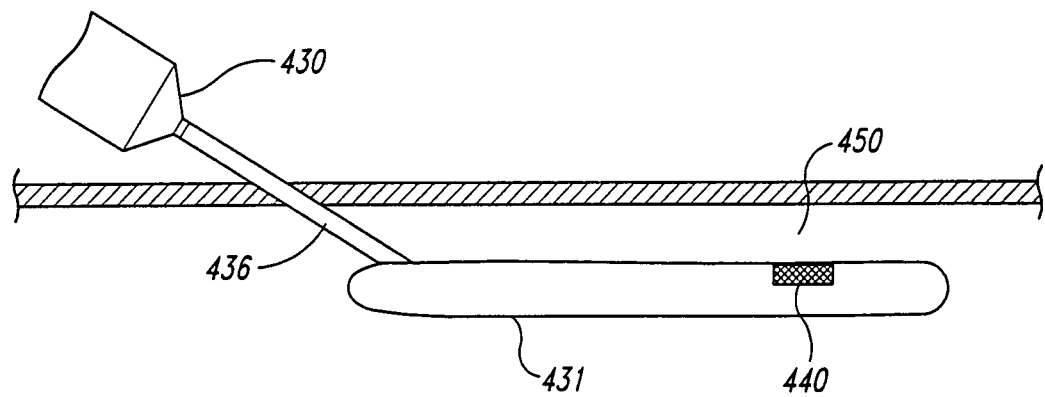
FIG. 44A is a schematic of the material delivery device following injection into an in vivo environment.
Figure 44B:
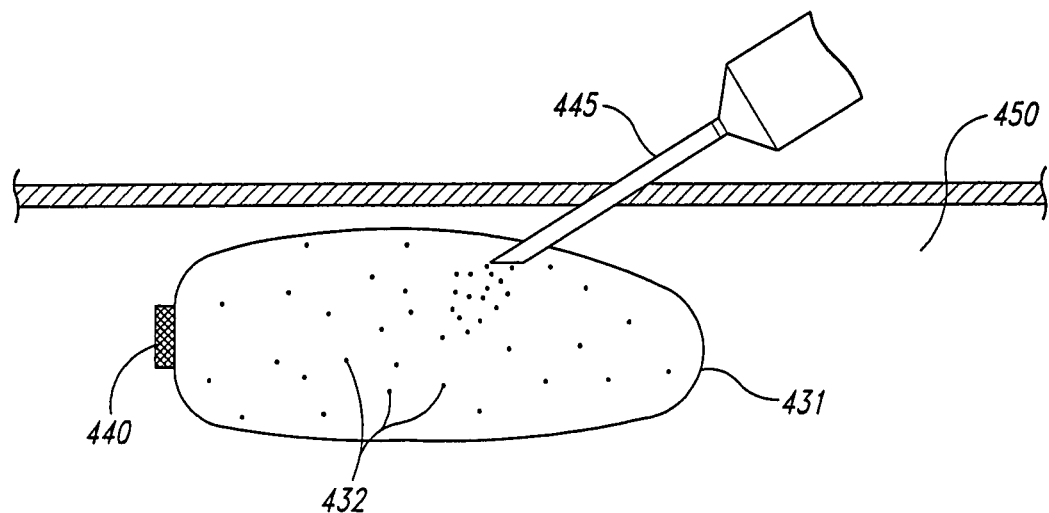
FIG. 44B is a schematic of the material delivery device receiving material from an external source.

FIG. 44A schematically illustrates an embodiment wherein the delivery device is deployed in the in vivo environment 450 prior to receiving the delivery material via syringe (in this Figure) or other means. FIG. 44B schematically depicts an alternate embodiment wherein the delivery device has been deployed in vivo 450 and the material 432 is thereafter percutaneously delivered to the device via a needle 445, e.g., in order to refill the reservoir 431.

An illustrative two-stage injection device that may be used for the deployment of a delivery device including a deformable reservoir and a material is described in U.S. Pat. No. 4,834,704, which is incorporated herein by reference. The devices, methods, or approaches of U.S. Pat. No. 4,834,704 can be adapted to include a controllable output mechanism operably linked to the at least one outlet. While the two-stage device is presented for illustrative purposes, other known devices and methods may also be adapted to provide such functionality.

Software may be used in performing a variety of the methods as described herein. Such software includes software for controlling delivery of a material from a delivery device, including instructions for generating an electromagnetic control signal including frequency components absorbable by at least one controllable output mechanism of a delivery device in an environment, the delivery device including a deformable reservoir capable of receiving and containing a delivery material, and having at least one outlet, wherein the delivery of the material is controllable by the at least one controllable output mechanism; and instructions for controlling the transmission of the electromagnetic control signal to the delivery device with signal characteristics sufficient to activate the at least one controllable output mechanism in the delivery device to control the delivery of material in the delivery device.

The software may include instructions for generating the electromagnetic control signal and include instructions for calculating the electromagnetic control signal based on a model. The instructions for generating the electromagnetic control signal may include instructions for generating the electromagnetic control signal based on a pattern stored in a data storage location, or instructions for generating the electromagnetic control signal based upon a feedback control algorithm. For example, the instructions for generating the electromagnetic control signal may include instructions for generating the electromagnetic control signal based upon a variable feedback control algorithm. The software may include instructions for receiving a feedback signal corresponding to one or more parameters sensed from the environment; and instructions for generating the electromagnetic control signal based at least in part upon the received feedback signal, the electromagnetic control signal having signal characteristics expected to produce a desired feedback signal. Some embodiments of the software may include instructions for receiving a feedback signal from the delivery device; and instructions for generating the electromagnetic control signal based at least in part on the received feedback signal, the electromagnetic control signal having frequency composition and amplitude expected to produce a desired feedback signal.

In some embodiments, the software may include instructions for receiving user input of one or more control parameters; and instructions for generating the electromagnetic control signal based at least in part upon the one or more control parameters. In some embodiments, the software may include instructions for performing encryption of the electromagnetic control signal. Instruction may be included for performing an authentication procedure between a remote controller transmitting the electromagnetic control signal and a delivery device including the controllable output mechanism intended to be activated by the electromagnetic control signal. At least a portion of the instructions generating the electromagnetic control signal and the instruction for controlling the transmission of the electromagnetic control signal are executable in distributed fashion on a plurality of microprocessors. Some embodiments of the software may include channel allocation instructions configured to control the allocation of control signal transmission channels for transmission of a plurality of control signals to a corresponding plurality of delivery devices.

With regard to the hardware and/or software used in the control of devices and systems according to the embodiments described herein, and particularly to the sensing, analysis, and control aspects of such systems, those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency or implementation convenience tradeoffs. Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and related processes or methods via the use of block diagrams, flowcharts, and/or examples. Insofar as such block diagrams, flowcharts, and/or examples contain one or more functions and/or operations, it will be implicitly understood by those with skill in the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the capabilities of one of skill in the art in light of this disclosure. In addition, those skilled in the art will appreciate that certain mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., links carrying packetized data).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices for detection or sensing, signal processing, and device control in the fashion set forth herein, and thereafter use standard engineering practices to integrate such described devices and/or processes into fluid handling and/or delivery systems as exemplified herein. That is, at least a portion of the devices and/or processes described herein can be integrated into a fluid handling and/or delivery system via a reasonable amount of experimentation.

Those having skill in the art will recognize that systems as described herein may include one or more of a memory such as volatile and non-volatile memory, processors such as microprocessors and digital signal processors, computational-supporting or -associated entities such as operating systems, user interfaces, drivers, sensors, actuators, applications programs, one or more interaction devices, such as data ports, control systems including feedback loops and control implementing actuators (e.g., devices for sensing osmolality, pH, pressure, temperature, or chemical concentration, signal generators for generating electromagnetic control signals). A system may be implemented utilizing any suitable available components, combined with standard engineering practices.

The foregoing-described aspects depict different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", "operably linked" or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

Although the methods, devices, systems and approaches herein have been described with reference to certain preferred embodiments, other embodiments are possible. As illustrated by the foregoing examples, various choices of remote controller, system configuration and fluid handling/delivery device may be within the scope of the invention. As has been discussed, the choice of system configuration may depend on the intended application of the system, the environment in which the system is used, cost, personal preference or other factors. System design, manufacture, and control processes may be modified to take into account choices of use environment and intended application, and such modifications, as known to those of skill in the arts of device design and construction, may fall within the scope of the invention. Therefore, the full spirit or scope of the invention is defined by the appended claims and is not to be limited to the specific embodiments described herein.

While various aspects and embodiments have been disclosed herein, other aspects and embodiments will be apparent to those skilled in the art. It is intended that the various aspects and embodiments disclosed herein are for purposes of illustration and are not intended to be limiting, with the true scope and spirit being indicated by the following claims.

What is claimed is:

1. A method of delivering at least one material to an animal, comprising:
   percutaneously injecting at least one material delivery device into an in vivo environment of the animal using a percutaneous injection mechanism, the percutaneous injection mechanism having a hollow body enclosing the at least one material delivery device, the at least one material delivery device including at least one collapsible reservoir having a biologically inert collapsible outer surface, the collapsible reservoir configured to receive, retain and controllably dispense the at least one material, a processor configured to cause emission of an electromagnetic control signal, and at least one controllable output mechanism coupled to the at least one collapsible reservoir, wherein the at least one controllable output mechanism defines or is located within at least one outlet through which the at least one material may be released;
   delivering a quantity of the at least one material into the at least one collapsible reservoir having a biologically inert collapsible outer surface;
   wherein the at least one controllable output mechanism includes a thermally-responsive material that absorbs an electromagnetic control signal and changes its shape to dispense the at least one material in response to at least one electromagnetic control signal; and
   delivering at least a portion of the quantity of the at least one material to the animal through the at least outlet responsive to the thermally-responsive material absorbing the electromagnetic control signal.

2. The method of claim 1, wherein the at least one collapsible reservoir having a biologically inert collapsible outer surface further comprises at least one inlet mechanism for receiving external delivery of a material.

3. The method of claim 1, wherein the at least one material delivery device includes RFID circuitry.

4. The method of claim 1, wherein the animal is a human.

5. The method of claim 1, wherein the at least one material delivery device further comprises at least one sensor, at least one timer, or at least one counter.

6. The method of claim 5, wherein the at least one sensor is located on the at least one material delivery device.

7. The method of claim 6, wherein the at least one sensor is configured to detect a quantity of the at least one material in the at least one collapsible reservoir having a biologically inert collapsible outer surface.

8. The method of claim 1, wherein the at least one material delivery device further comprises at least one electronic memory location for recording information.

9. The method of claim 1, wherein the at least one electromagnetic control signal is provided by at least one remote controller.

10. The method of claim 9, wherein the at least one remote controller comprises at least one of hardware, firmware, or software configured to control transmission of the at least one electromagnetic control signal.

11. The method of claim 1, wherein the at least one material comprises at least one therapeutic agent.

12. The method of claim 11, wherein the at least one therapeutic agent comprises a therapeutically immunogenic amount of at least one vaccine.

13. The method of claim 11, wherein the at least one therapeutic agent includes a therapeutically effective amount of at least one anti-infective agent.

14. The method of claim 13, wherein the at least one anti-infective agent includes at least one anti-viral agent.

15. The method of claim 13, wherein the at least one anti-infective agent includes at least one anti-microbial agent.

16. The method of claim 11, wherein the at least one therapeutic agent includes a therapeutically effective amount of at least one agent to treat malaria.

17. The method of claim 11, wherein the at least one therapeutic agent includes a therapeutically effective amount of at least one agent to treat tuberculosis.

18. The method of claim 11, wherein the at least one therapeutic agent includes a therapeutically effective amount of at least one agent to treat leschmaniasis.

19. The method of claim 11, wherein the at least one therapeutic agent includes a therapeutically effective amount of at least one agent to treat cholera.

20. The method of claim 1, wherein the at least one material is a fluid.

21. The method of claim 1, wherein the animal is a mammal.

22. A method of delivering at least one material to an animal, comprising:
   percutaneously injecting at least one material delivery device into an in vivo environment of the animal using a percutaneous injection mechanism, the percutaneous injection mechanism having a hollow body enclosing the at least one material delivery device, the at least one material delivery device including at least one collapsible reservoir having a biologically inert collapsible outer surface, the collapsible reservoir configured to receive, retain and controllably dispense the at least one material, a processor configured to cause emission of a magnetic control signal, and at least one controllable output mechanism coupled to the at least one collapsible reservoir, wherein the at least one controllable output mechanism defines or is located within at least one outlet through which the at least one material may be released; and
   delivering a quantity of the at least one material into the at least one collapsible reservoir having a biologically inert collapsible outer surface;
   wherein the at least one controllable output mechanism includes a magnetically-active material that absorbs a magnetic control signal and changes its shape to dispense the at least one material in response to at least one magnetic control signal; and delivering at least a portion of the quantity of the at least one material to the animal through the at least outlet responsive to the magnetically-active material receiving the magnetic control signal.

23. A method of delivering at least one material to an animal, comprising:

percutaneously injecting at least one material delivery device into an in vivo environment of the animal using a percutaneous injection mechanism, the percutaneous injection mechanism having a hollow body enclosing the at least one material delivery device, the at least one material delivery device including at least one collapsible reservoir having a biologically inert collapsible outer surface, the collapsible reservoir configured to receive, retain and controllably dispense the at least one material, and including at least one outlet, and at least one controllable output mechanism operably linked to the at least one outlet; and delivering a quantity of the at least one material into the at least one collapsible reservoir having a biologically inert collapsible outer surface;

wherein the at least one controllable output mechanism includes a shape-changing structure selected from the group consisting of a ferropolymer, a bimetallic structure and a shape memory material and dispenses the at least one material in response to at least one electromagnetic control signal.

* * * * *